(12) United States Patent
Tanabe et al.

(10) Patent No.: US 10,333,078 B2
(45) Date of Patent: Jun. 25, 2019

(54) FLUORESCENT ORGANIC LIGHT EMITTING ELEMENTS HAVING HIGH EFFICIENCY

(71) Applicant: BASF SE, Ludwigshafen (DE)

(72) Inventors: Junichi Tanabe, Dublin (IE); Christian Lennartz, Dublin (IE)

(73) Assignee: UDC IRELAND LIMITED, Dublin (IE)

( * ) Notice: Subject to any disclaimer, the term of this patent is extended or adjusted under 35 U.S.C. 154(b) by 0 days.

(21) Appl. No.: 15/512,699

(22) PCT Filed: Sep. 25, 2015

(86) PCT No.: PCT/EP2015/072053
§ 371 (c)(1),
(2) Date: Mar. 20, 2017

(87) PCT Pub. No.: WO2016/046350
PCT Pub. Date: Mar. 31, 2016

(65) Prior Publication Data
US 2017/0309828 A1 Oct. 26, 2017

(30) Foreign Application Priority Data
Sep. 26, 2014 (EP) .................................... 14186587

(51) Int. Cl.
*C07D 241/46* (2006.01)
*C07D 249/08* (2006.01)
*C07D 265/38* (2006.01)
*C07D 271/06* (2006.01)
*C07D 279/18* (2006.01)
*C09K 11/06* (2006.01)
*H05B 33/14* (2006.01)
*H01L 51/00* (2006.01)
*C07D 401/14* (2006.01)
*C07D 413/14* (2006.01)
*C07D 401/10* (2006.01)
*C07D 403/10* (2006.01)
*C07D 403/14* (2006.01)
*C07D 413/04* (2006.01)
*C07D 413/10* (2006.01)
*C07D 417/14* (2006.01)
*C07D 487/04* (2006.01)
*C07F 7/08* (2006.01)
*C09K 11/02* (2006.01)
*H01L 51/50* (2006.01)

(52) U.S. Cl.
CPC ........ *H01L 51/0067* (2013.01); *C07D 249/08* (2013.01); *C07D 271/06* (2013.01); *C07D 401/10* (2013.01); *C07D 401/14* (2013.01); *C07D 403/10* (2013.01); *C07D 403/14* (2013.01); *C07D 413/04* (2013.01); *C07D 413/10* (2013.01); *C07D 413/14* (2013.01); *C07D 417/14* (2013.01); *C07D 487/04* (2013.01); *C07F 7/0816* (2013.01); *C09K 11/025* (2013.01); *C09K 11/06* (2013.01); *H01L 51/0071* (2013.01); *C09K 2211/104* (2013.01); *C09K 2211/1011* (2013.01); *C09K 2211/1018* (2013.01); *C09K 2211/1029* (2013.01); *C09K 2211/1033* (2013.01); *C09K 2211/1037* (2013.01); *C09K 2211/1044* (2013.01); *C09K 2211/1051* (2013.01); *C09K 2211/1059* (2013.01); *C09K 2211/1096* (2013.01); *H01L 51/5012* (2013.01); *H01L 2251/552* (2013.01); *Y02E 10/549* (2013.01)

(58) Field of Classification Search
CPC .. C07D 241/46; C07D 249/08; C07D 265/38; C07D 271/06; C07D 279/18; C09K 11/06; H05B 33/14; H01L 51/5032; H01L 51/5064; H01L 51/5296; H01L 51/0032
USPC ....... 544/35, 102, 344; 548/128, 131, 262.2; 257/40, E51.019; 428/917; 313/501
See application file for complete search history.

(56) References Cited

U.S. PATENT DOCUMENTS

| | | | |
|---|---|---|---|
| 2010/0240902 A1 | 9/2010 | Nomura | |
| 2010/0243959 A1 | 9/2010 | Nomura | |
| 2012/0038264 A1 | 2/2012 | Liu | |
| 2017/0244049 A1* | 8/2017 | Aspuru-Guzik | .... H01L 51/0072 |

FOREIGN PATENT DOCUMENTS

| | | |
|---|---|---|
| CN | 101171239 A | 4/2008 |
| CN | 101602746 A | 12/2009 |

(Continued)

OTHER PUBLICATIONS

Atzrodt et al. Angew. Chem. Int. Ed. 2007, 46, 7744-7765.*

(Continued)

*Primary Examiner* — Venkataraman Balasubramanian
(74) *Attorney, Agent, or Firm* — Riverside Law LLP

(57) ABSTRACT

An organic light-emitting element which emits delayed fluorescence comprising specifically substituted 1,2,4-triazole derivatives, 1,2,4-oxadiazole derivatives or 1,2,4-thiadiazole derivatives in the light-emitting layer, a light-emitting layer comprising the specifically substituted 1,2,4-triazole derivatives, 1,2,4-oxadiazole derivatives or 1,2,4-thiadiazole derivatives, specific specifically substituted 1,2,4-triazole derivatives, 1,2,4-oxadiazole derivatives and 1,2,4-thiadiazole derivatives and an organic light emitting element comprising the specific 1,2,4-azole derivatives as well as a light emitting layer comprising the specific 1,2,4-azole derivatives; the use of the specifically substituted 1,2,4-triazole derivatives, 1,2,4-oxadiazole derivatives and 1,2,4-thiadiazole derivatives for electrophotographic photoreceptors, photoelectric converters, sensors, dye lasers, solar cell devices and organic light emitting elements, and the use of the specifically substituted 1,2,4-triazole derivatives, 1,2,4-oxadiazole derivatives and 1,2,4-thiadiazole derivatives for generating delayed fluorescence emission.

23 Claims, No Drawings

(56) References Cited

FOREIGN PATENT DOCUMENTS

| | | |
|---|---|---|
| CN | 103588770 A | 2/2014 |
| EP | 1097981 | 5/2001 |
| EP | 1786050 | 5/2007 |
| EP | 1970371 | 9/2008 |
| JP | H10340786 | 12/1998 |
| KR | 101160670 | 6/2011 |
| KR | 20110085784 | 7/2011 |
| KR | 20130007390 A | 1/2013 |
| TW | 201434832 | 9/2014 |
| WO | 02060910 A1 | 8/2002 |
| WO | 2006114377 | 11/2006 |
| WO | 2014126076 A1 | 8/2014 |

OTHER PUBLICATIONS

PubChem Compound- CID 3805347, create date Sep. 11, 2005.*
Endo, 2009, "Thermally Activated Delayed Fluorescence from Sn4þ —Porphyrin Complexes and Their Application to Organic Light-Emitting Diodes—A Novel Mechanism," for Electroluminescence Adv. Mater. 21:4802.
Endo, 2011, "Efficient up-conversion of triplet excitons into a singlet state and its application for organic light emitting diodes," App. Phys. Lett. 98:083302.
Nakagawa, 2012, "Electroluminescence based on thermally activated delayed fluorescence generated by a spirobifluorene donor-acceptor structure," Chem. Comm. 48:9580.
Li et al., 2014, "Synthesis of new bipolar host materials based on 1,2,4-oxadiazole for blue phosphorescent OLEDs," Dyes and Pigments 101:142-148.
Jin et al., 2014, "Construction of High Tg Bipolar Host Materials with Balanced Electron-Hole Mobility Based on 1,2,4-Thiadiazole for Phosphorescent Organic Light-Emitting Diodes," Chem. Mater. 26:2388-2395.

\* cited by examiner

FLUORESCENT ORGANIC LIGHT EMITTING ELEMENTS HAVING HIGH EFFICIENCY

CROSS-REFERENCE TO RELATED APPLICATIONS

This application is the U.S. National Stage Application filed under 35 U.S.C. § 371 of International Patent Application No. PCT/EP2015/072053, filed Sep. 25, 2015, which is entitled to priority under 35 U.S.C. § 119(e) to European Patent Application 14186587.3, filed Sep. 26, 2014, all of which applications are hereby incorporated by reference in their entireties.

The present invention relates to an organic light-emitting element which emits delayed fluorescence comprising specifically substituted 1,2,4-triazole derivatives, 1,2,4-oxadiazole derivatives or 1,2,4-thiadiazole derivatives in the light-emitting layer, a light-emitting layer comprising the specifically substituted 1,2,4-triazole derivatives, 1,2,4-oxadiazole derivatives or 1,2,4-thiadiazole derivatives, specific specifically substituted 1,2,4-triazole derivatives, 1,2,4-oxadiazole derivatives and 1,2,4-thiadiazole derivatives and an organic light emitting element comprising the specific 1,2,4-azole derivatives as well as a light emitting layer comprising the specific 1,2,4-azole derivatives; the use of the specifically substituted 1,2,4-triazole derivatives, 1,2,4-oxadiazole derivatives and 1,2,4-thiadiazole derivatives for electrophotographic photoreceptors, photoelectric converters, sensors, dye lasers, solar cell devices and organic light emitting elements, and the use of the specifically substituted 1,2,4-triazole derivatives, 1,2,4-oxadiazole derivatives and 1,2,4-thiadiazole derivatives for generating delayed fluorescence emission.

The specifically substituted 1,2,4-triazole derivatives, 1,2,4-oxadiazole derivatives and 1,2,4-thiadiazole derivatives exhibit TADF (thermally activated delayed fluorescence) characteristics, usually at 298 K.

TADF is an effective triplet-harvesting process that involves up-conversion of triplet ($T_1$) to singlet ($S_1$) excited states.

Derivatives exhibiting TADF characteristics are characterized by having a sufficiently small energy gap between $S_1$ and $T_1$ ($\Delta E_{ST}$) to enable up-conversion of the triplet exciton from $T_1$ to $S_1$.

The present invention therefore relates to organic light emitting elements, which emit delayed fluorescence comprising the specifically substituted 1,2,4-triazole derivatives, 1,2,4-oxadiazole derivatives and 1,2,4-thiadiazole derivatives as thermally activated delayed fluorescence (TADF) emitters (guests) and/or hosts. The organic light emitting elements show high electroluminescent efficiency.

The development of OLED luminescent materials is an important issue and these materials have been classified into two major categories. The first category concerns fluorescent materials, which can harvest only the singlet excitons (25%) that are generated by electrical excitation. The second category concerns phosphorescent materials, which can harvest the triplet excitons generated (75%). The branching ratio of singlet and triplet excitons is 1:3. Therefore, in recent devices, phosphorescent materials and their related technologies have been indispensable to obtain high EL efficiency. However, phosphorescent materials are generally based on organometallic compounds containing Ir or Pt. These metals are rather expensive and are dependent on limited global resources.

Recently, the alternative concept of thermally activated delayed fluorescence (TADF) as a third generation luminescent material, instead of the conventional fluorescent and phosphorescent materials was described by C. Adachi et al. in Adv. Mater., 2009, 21, 4802; Appl. Phys. Lett., 2011, 98, 083302 and Chem. Commun., 2012, 48, 9580.

The TADF strongly depends on HOMO-LUMO separation in a single molecule. TADF materials have a sufficiently small energy gap between $S_1$ and $T_1$ ($\Delta E_{ST}$) to enable up-conversion of the triplet exciton from $T_1$ to $S_1$. This small $\Delta E_{ST}$ enables TADF materials to realize 100% of the exciton formation generated by electrical excitation at $S_1$.

$\Delta E_{ST}$ is the difference between the lowest excited singlet state $S_1$ and the lowest excited triplet state $T_1$ of a molecule. In the case that the energy gap between $S_1$ and $T_1$ ($\Delta E_{ST}$) is small enough to provide a thermal up-conversion of the triplet exciton from $T_1$ to $S_1$ according to a Boltzmann distribution, or pursuant to the thermal energy $k_B T$, a thermally activated light emission from the $S_1$ state is allowed (TADF), based on the following equation:

$$\mathrm{Int}(S_1 \to S_0)/\mathrm{Int}(T_1 \to T_0) = k(S_1)/k(T_1)\exp(-\Delta E/k_B T)$$

wherein,
$\mathrm{Int}(S_1 \to S_0)/\mathrm{Int}(T_1 \to T_0)$ is the intensity ratio of the emission from the $S_1$ state and the $T_1$ state $k_B$ is the Boltzmann constant
T is the absolute temperature
$k(S_1)/k(T_1)$ is the rate ratio of the transition processes from the singlet $S_1$ state and from the triplet $T_1$ state in the electronic ground state $S_0$.

WO 2006/114377 A1 relates to electroluminescent devices comprising organic layers containing triazole compounds of formula (I) or (II):

(I)

(II)

The triazole compounds are suitable components of organo-electroluminescent layers, according to the examples as a host component. According to the examples, the following triazole compounds are used as host materials in OLEDs:

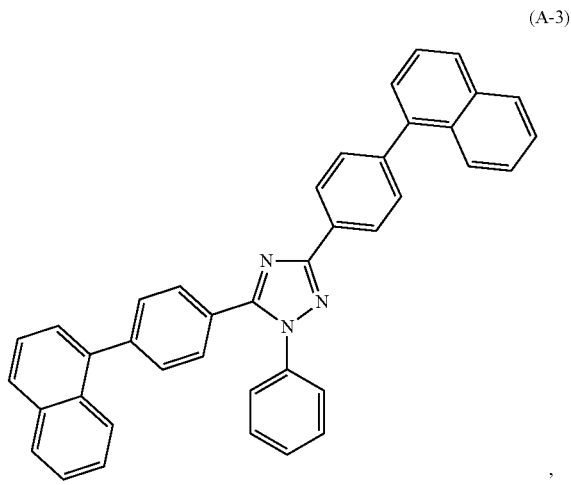

(A-3)

(A-6)
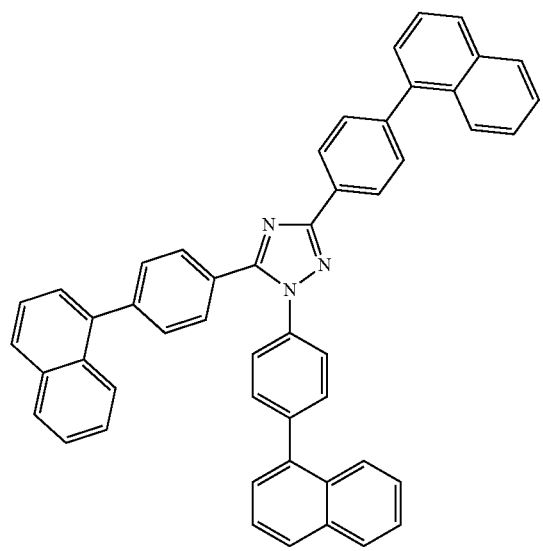
(A-14)
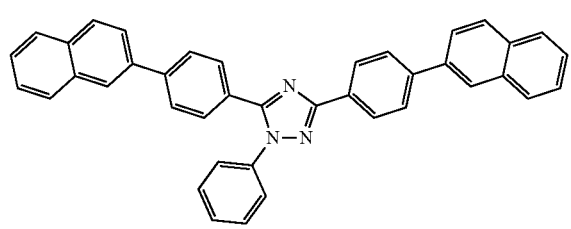
(A-19)
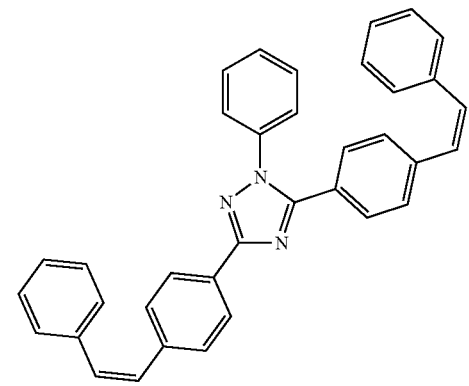
(A-20)
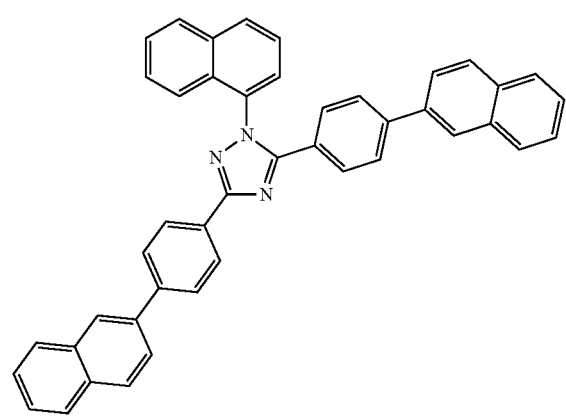
(A-21)
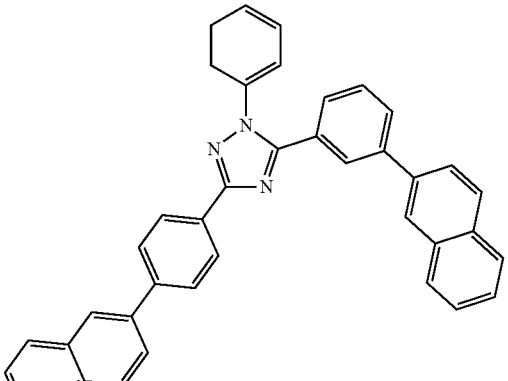
, and
(B-4)
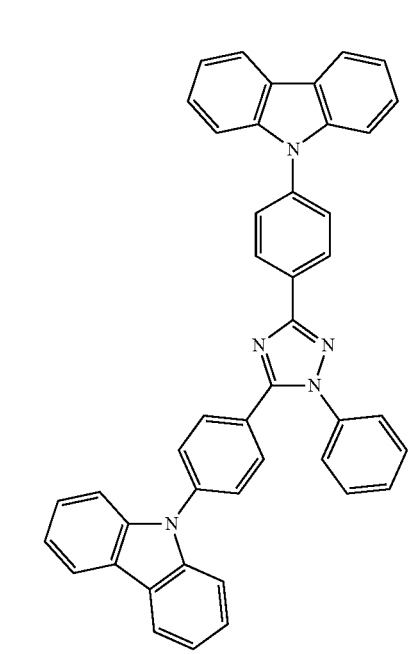
.
US 2010/0243959 A1 concerns derivatives of the formula G1
(G1)
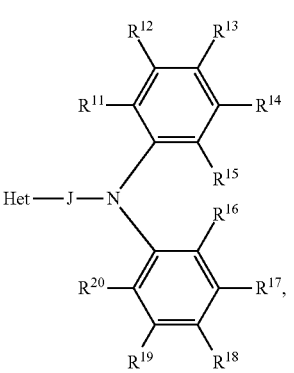
wherein Het is a substituent of formula (S1-1) or (S1-2)

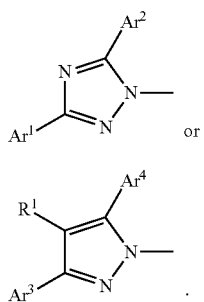

The compounds are used as hosts with bipolar properties for phosphorescent as well as fluorescent emitters in light-emitting elements. Examples for compounds G1 are:

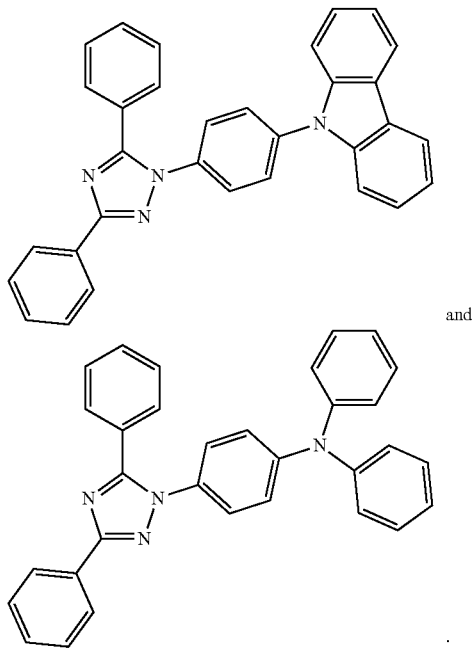

US 2010/0240902 A1 concerns oxadiazole derivatives of formula 1

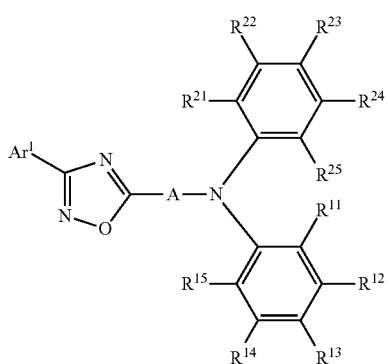

The compounds are used in the light-emitting layer in light-emitting elements. Examples for compounds 1 are:

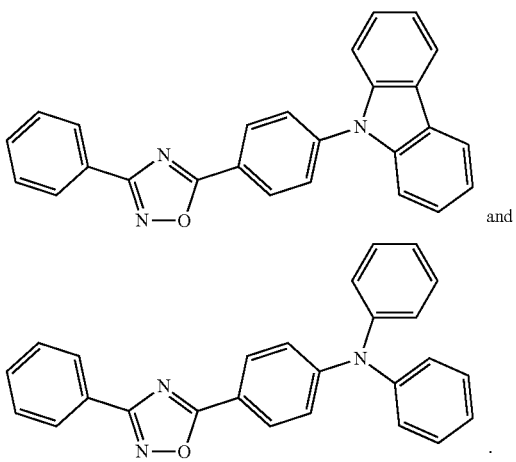

Q. Li et al., Dyes and Pigments 101 (2014) 142-148 concerns the synthesis of new bipolar host materials based on 1,2,4-oxadiazole for blue phosphorescent OLEDs. The following host materials are mentioned:

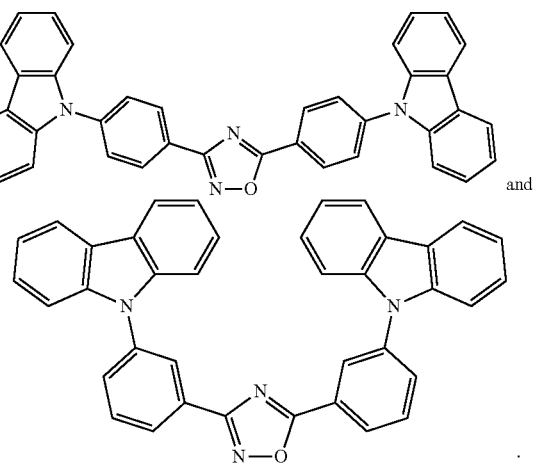

J. Jin et al., Chem. Mater. 2014 (26) 2388-2395 concerns bipolar host materials based on 1,2,4-thiadiazole for phosphorescent organic light-emitting diodes. The following host materials are mentioned:

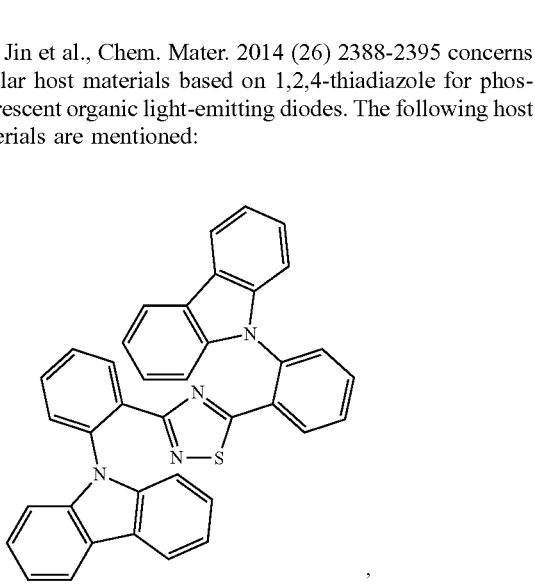

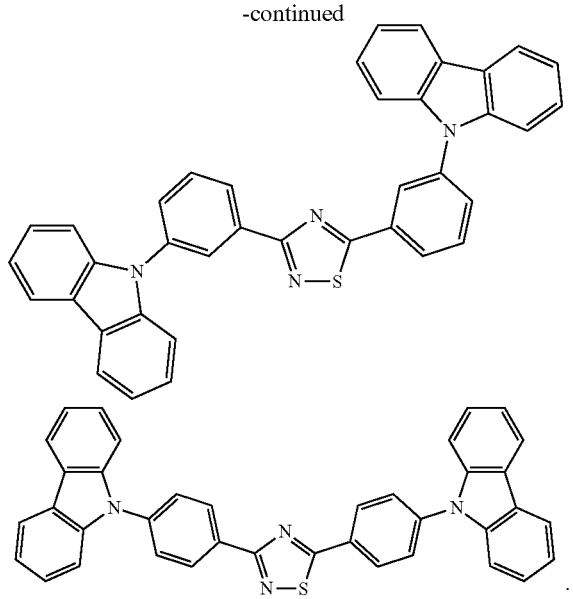

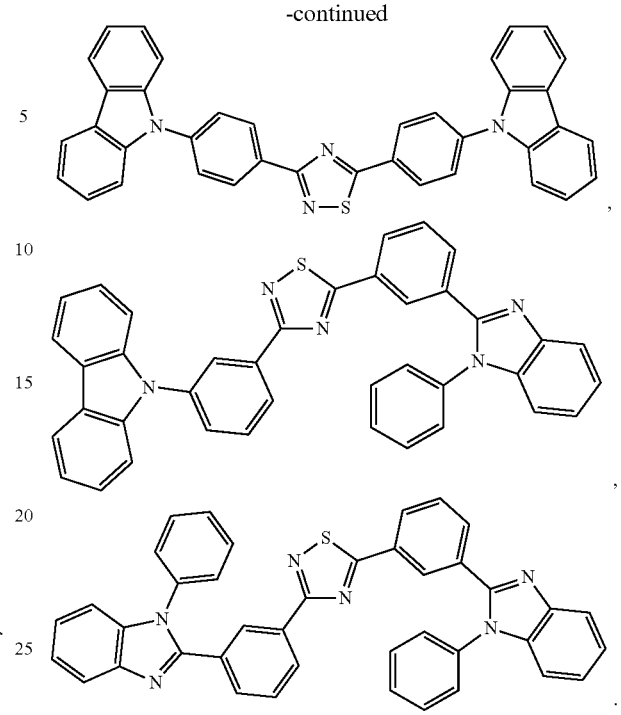

CN 10358870 A relates to the design and synthesis of 3,5-diphenyl substituted 1,2,4-thiadiazole derivatives as well as the application of the 3,5-diphenyl substituted 1,2,4-thiadiazole derivatives in an organic electroluminescent device (OLED). The 3,5-diphenyl substituted 1,2,4-thiadiazole derivatives may be used in the light-emitting layer of an OLED as host or light-emitting material or in a transport layer of an OLED as hole or electron transport material. According to the examples in CN 10358870 A, the 3,5-diphenyl substituted 1,2,4-thiadiazole derivatives are used as host materials in OLEDs for phosphorescent green emitters. The following 3,5-diphenyl substituted 1,2,4-thiadiazole derivatives are explicitly mentioned:

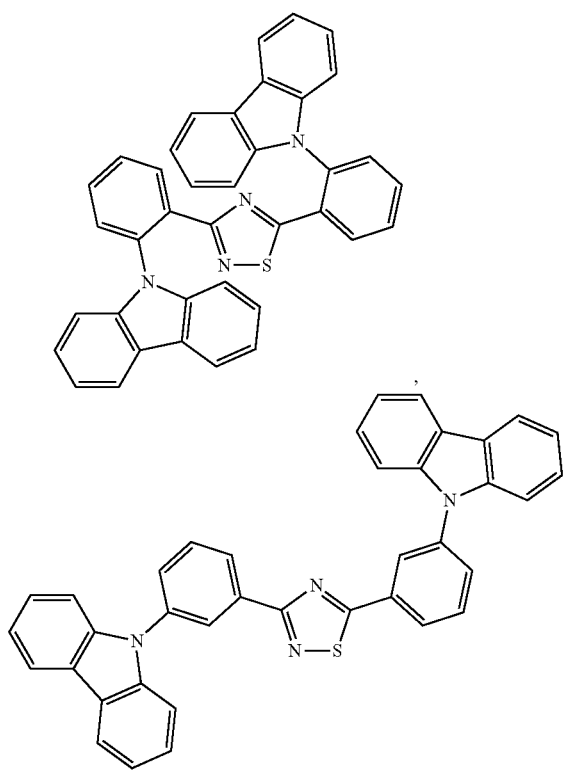

None of the documents mentioned above mentions TADF (thermally activated delayed fluorescence) characteristics of the compounds disclosed.

An object of the present invention is to provide a highly efficient and practically useful organic light-emitting element and an organic material suitable for providing the organic light-emitting element.

It has surprisingly been found that certain specifically substituted 1,2,4-triazole derivatives, 1,2,4-oxadiazole derivatives and 1,2,4-thiadiazole derivatives emit delayed fluorescence, usually at 298 K, and are useful for providing an organic light-emitting element having a high efficiency. The temperature of 298 K mentioned before means that the specifically substituted 1,2,4-triazole derivatives, 1,2,4-oxadiazole derivatives and 1,2,4-thiadiazole derivatives of formulae (I) and (I') according to the present invention show delayed fluorescence at room temperature (298 K) and does not mean that the specifically substituted 1,2,4-triazole derivatives, 1,2,4-oxadiazole derivatives and 1,2,4-thiadiazole derivatives according to the present invention do not emit delayed fluorescence at lower temperatures and at higher temperatures.

Accordingly, the present invention relates to an organic light-emitting element, comprising a light-emitting layer comprising i) a compound of formula

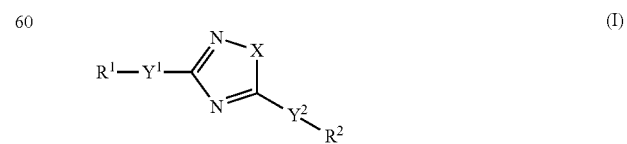

as guest and a host material; or ii) a compound of formula

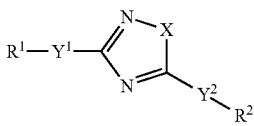
(I)

as host and a fluorescent guest material, wherein
wherein
X is O, S or N—Y$^4$—R$^4$,
Y$^1$ and Y$^2$ and Y$^4$ are independently of each other a direct bond, C$_1$-C$_{25}$-alkylene, or C$_6$-C$_{10}$-arylene, which is unsubstituted or substituted by one or more groups R$^3$;
R$^1$ and R$^2$ are independently of each other hydrogen, deuterium, F, Cl, a C$_1$-C$_{25}$alkyl group, a C$_1$-C$_{25}$alkoxy group, a C$_6$-C$_{14}$aryloxy group, which is unsubstituted or substituted by one or more groups R$^3$, a C$_6$-C$_{14}$aryl group, which is unsubstituted or substituted by one or more groups R$^3$, or a group of formula (Xa) or (Xd); preferably, R$^1$ and R$^2$ are independently of each other hydrogen, a C$_1$-C$_{25}$alkyl group, a C$_1$-C$_{25}$alkoxy group, a C$_6$-C$_{10}$aryl group, which is unsubstituted or substituted by one or more groups R$^3$, or a group of formula (Xa) or (Xd);
R$^3$ is deuterium, F, Cl, a C$_1$-C$_{25}$alkyl group, a C$_1$-C$_{25}$alkoxy group, a C$_6$-C$_{14}$aryloxy group, or a C$_6$-C$_{14}$aryl group; preferably, R$^3$ is a C$_1$-C$_{25}$alkyl group, a C$_1$-C$_{25}$alkoxy group, a C$_6$-C$_{10}$aryloxy group, or C$_6$-C$_{14}$aryl group;
R$^4$ is a C$_1$-C$_{25}$alkyl group, a C$_6$-C$_{10}$aryl group, which is unsubstituted or substituted by one or more groups R$^3$, or a group of formula (Xa) or (Xd);

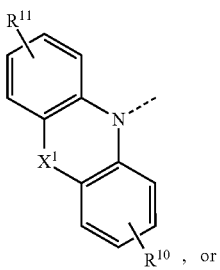
(Xa)

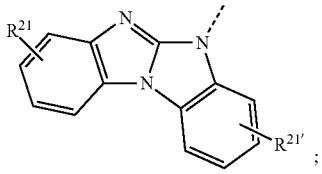
(Xd)

X$^1$ is O, S, N(R$^{15}$), C(═O), C(R$^{16}$)(R$^{17}$), B(R$^{18}$), or Si(R$^{19}$)(R$^{20}$); preferably, X$^1$ is O, S, C(O), N(R$^{15}$), or C(R$^{16}$)(R$^{17}$);
R$^{10}$, R$^{11}$, R$^{21}$ and R$^{21'}$ are independently of each other hydrogen, deuterium, F, Cl, a C$_1$-C$_{25}$alkyl group, a C$_1$-C$_{25}$alkoxy group, a C$_6$-C$_{14}$aryloxy group, which is unsubstituted or substituted by one or more groups R$^3$, or a C$_6$-C$_{14}$aryl group, which is unsubstituted or substituted by one or more groups R$^3$; preferably, R$^{10}$, R$^{11}$, R$^{21}$ and R$^{21'}$ are independently of each other hydrogen, or a C$_1$-C$_{25}$alkyl group;
R$^{15}$, R$^{16}$, R$^{17}$, R$^{18}$, R$^{19}$ and R$^{20}$ are independently of each other a C$_1$-C$_{25}$alkyl group, or a C$_6$-C$_{14}$aryl group, which is unsubstituted or substituted by one or more groups R$^3$;

wherein at least one group of formula (Xa), or (Xd) is present in the compound of formula (I), characterized in that it emits delayed fluorescence.

The present invention is also directed to the use of compounds of formula (I) for generating delayed fluorescence emission.

Thermally activated delayed fluorescence (TADF, E-type delayed fluorescence) is a promising way to obtain a high efficiency of exciton formation by converting spin-forbidden triplet excitons up to the singlet level by the mechanism of reverse intersystem crossing (RISC). In a TADF emitter, the upconversion mechanism uses the vibronic energy that, at sufficiently high temperatures (usually about 298 K), allows all of the excitons in an OLED to eventually produce light through singlet decay.

E-type delayed fluorescence is defined herein as a process in which the first excited singlet state (S$_1$) becomes populated by a thermally activated radiationless transition from the first excited triplet state (T$_1$).

The present invention is also directed to an organic light-emitting element, comprising a compound of formula (I) in the light-emitting layer, characterized in that it emits delayed fluorescence.

The organic light-emitting element preferably offers an external quantum efficiency of more than 5%, especially more than 10%. Further, the organic light-emitting element of the present invention shows reduced efficiency roll-off characteristics at high luminance.

The compound of formula (I) has preferably a difference between excited singlet energy (S$_1$) and excited triplet energy (T$_1$) (($\Delta E_{ST}$) of 0.5 eV or less, more preferably $\Delta E_{ST}$ of 0.35 eV or less, i.e. of 0.01 to 0.5 eV, especially 0.01 to 0.35 eV.

In the meaning of the present invention, an organic light-emitting element, comprising a light-emitting layer comprising a compound of formula (I), characterized in that it emits delayed fluorescence, is preferably an organic light-emitting element, comprising a light-emitting layer comprising a compound of formula (I), wherein the compound of formula (I) has a difference between excited singlet energy (S$_1$) and excited triplet energy (T$_1$) ($\Delta E_{ST}$) of 0.5 eV or less, more preferably $\Delta E_{ST}$ of 0.35 eV or less, i.e. a $\Delta E_{ST}$ of 0.01 to 0.5 eV, especially 0.01 to 0.35 eV.

The determination of $\Delta E_{ST}$ can be carried either by quantum mechanical calculations (for example TD-DFT (time dependent density functional theory) calculations, for example with commercially available Gaussian 09 or ADF Amsterdam Density Functional software programs; for example as described in Adv. Mater. 2008, 20, 3325-3330) or experimentally.

Experimental Determination of $\Delta E_{ST}$:
i)
$\Delta E_{ST}$ can be determined based on the information given in the following formula:

$$\text{Int}(S_1 \rightarrow S_0)/\text{Int}(T_1 \rightarrow T_0) = k(S_1)/k(T_1)\exp(-\Delta E/k_B T).$$

The intensities Int(S$_1$→S$_0$) and Int(T$_1$→T$_0$) can be determined spectroscopically by a spectrophotometer.

A graph of the logarithmic intensity ratios Int(S$_1$→S$_0$)/Int(T$_1$→T$_0$) measured at different temperatures versus the reciprocal of the absolute temperature T generally shows a straight line. The measurement is carried out in a temperature range from room temperature (300 K) to 77 K to 4.2 K (the temperature can be adjusted by means of a cryostat). The respective transitions (S$_1$→S$_0$) and (T$_1$→T$_0$) (band intensities) can be identified since the triplet transition is at lower energy than the singlet transition and increases in intensity with decreasing temperature. The measurements are usually performed in oxygen-free dilute solutions (about $10^{-2}$ molL$^{-1}$) or thin films of the respective compounds or doped films comprising the corresponding compounds.

The slope of the straight line mentioned above is $-\Delta E/k_B T$. With $k_B=1.380 \ 10^{-23}$ JK$^{-1}$=0.695 cm$^{-1}$ K$^{-1}$, $\Delta E_{ST}$ can be determined.

ii)

$\Delta E_{ST}$ can also be determined by measuring the temperature dependency of the emission decay as known by a person skilled in the art.

iii)

An approximate estimation of $\Delta E_{ST}$ can be achieved by recording the fluorescence and phosphorescence spectra at low temperature (for example 77 K or 4.2 K using a cryostat). $\Delta E_{ST}$ then corresponds to an approximation of the energy difference between the high-energy rising edges of the fluorescence or phosphorescence band.

The compounds of formula (I) contain—when X is O or S—one or two groups of formula (Xa) and/or (Xd).

The compounds of formula (I) contain—when X is N—Y$^4$—R$^4$—one, two or three groups of formula (Xa) and/or (Xd).

In the compounds of formula (I), the residues and symbols have the following meanings:

X is O, S or N—Y$^4$—R$^4$.

Y$^1$ and Y$^2$ and Y$^4$ are independently of each other a direct bond, C$_1$-C$_{25}$-alkylene, or C$_6$-C$_{10}$-arylene, which is unsubstituted or substituted by one or more groups R$^3$; preferably a direct bond, or a C$_6$-C$_{10}$arylene group which is unsubstituted or substituted by one or more C$_1$-C$_{25}$alkyl groups. Examples of C$_6$-C$_{10}$arylene groups are phenylene and naphthylene. Preferred C$_6$-C$_{10}$arylene groups are 1,3-phenylene and 3,6-naphthylene, which may be unsubstituted or substituted by one or more C$_1$-C$_8$alkyl groups. Y$^1$ and Y$^2$ and Y$^4$ are more preferably a direct bond, or a group of formula

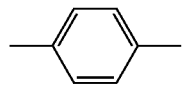

R$^1$ and R$^2$ are independently of each other hydrogen, deuterium, F, Cl, a C$_1$-C$_{25}$alkyl group, a C$_1$-C$_{25}$alkoxy group, a C$_6$-C$_{14}$aryloxy group, which is unsubstituted or substituted by one or more groups R$^3$, a C$_6$-C$_{14}$aryl group, which is unsubstituted or substituted by one or more groups R$^3$, or a donor group of formula (Xa) or (Xd); preferably, R$^1$ and R$^2$ are independently of each other hydrogen, a C$_1$-C$_{25}$alkyl group, a C$_1$-C$_{25}$alkoxy group, a C$_6$-C$_{10}$aryl group, which is unsubstituted or substituted by one or more groups R$^3$, or a group of formula

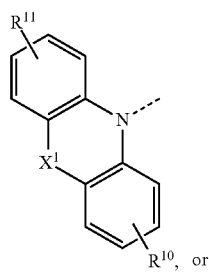

(Xa)

-continued

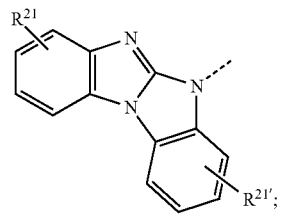

(Xd)

more preferably, R$^1$ and R$^2$ are independently of each other hydrogen, a C$_6$-C$_{10}$aryl group, or a group of formula

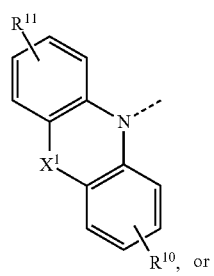

(Xa)

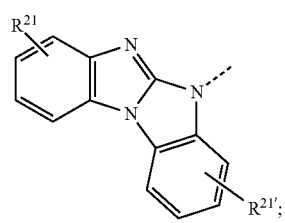

(Xd)

most preferably, R$^1$ and R$^2$ are independently of each other hydrogen, or a group of formula

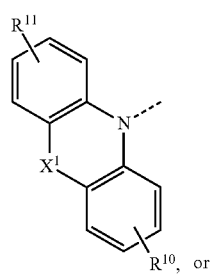

(Xa)

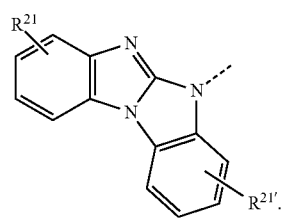

(Xd)

R$^3$ is deuterium, F, Cl, a C$_1$-C$_{25}$alkyl group, a C$_1$-C$_{25}$alkoxy group, a C$_6$-C$_{14}$aryloxy group, or a C$_6$-C$_{14}$aryl group; preferably, R$^3$ is a C$_1$-C$_{25}$alkyl group, a C$_1$-C$_{25}$alkoxy group, a C$_6$-C$_{14}$aryloxy group, or a C$_6$-C$_{14}$aryl group; more preferably, R$^3$ is a C$_1$-C$_{25}$alkyl group or a C$_1$-C$_{25}$alkoxy group.

R⁴ is a $C_1$-$C_{25}$alkyl group, a $C_6$-$C_{10}$aryl group, which is unsubstituted or substituted by one or more groups R³, or a group of formula

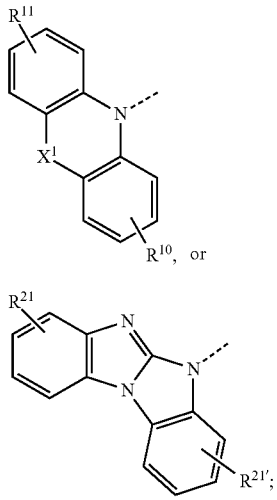

(Xa)

(Xd)

preferably, R⁴ is hydrogen, a $C_6$-$C_{10}$aryl group, or a group of formula (Xa) or (Xd).

$X^1$ is O, S, N(R¹⁵), C(=O), C(R¹⁶)(R¹⁷), B(R¹⁸), or Si(R¹⁹)(R²⁰); preferably, $X^1$ is O, S, C(O), N(R¹⁵), or C(R¹⁶)(R¹⁷); more preferably, $X^1$ is O, S, C(CH₃)(CH₃), C(=O), or

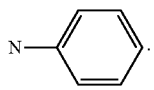

R¹⁰, R¹¹, R²¹ and R²¹' are independently of each other hydrogen, deuterium, F, Cl, a $C_1$-$C_{25}$alkyl group, a $C_1$-$C_{25}$alkoxy group, a $C_6$-$C_{14}$aryloxy group, which is unsubstituted or substituted by one or more groups R³, or a $C_6$-$C_{14}$aryl group, which is unsubstituted or substituted by one or more groups R³; preferably, R¹⁰, R¹¹, R²¹ and R²¹' are independently of each other hydrogen, or a $C_1$-$C_{25}$alkyl group.

R¹⁵, R¹⁶, R¹⁷, R¹⁸, R¹⁹ and R²⁰ are independently of each other a $C_1$-$C_{25}$alkyl group, or a $C_6$-$C_{14}$aryl group, which is unsubstituted or substituted by one or more groups R³; preferably, R¹⁵ and R¹⁸ are independently of each other a group of formula

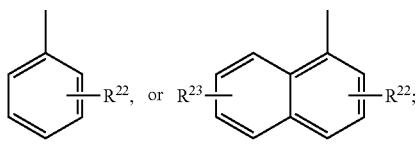

and R¹⁶, R¹⁷, R¹⁹ and R²⁰ are independently of each other hydrogen, or a $C_1$-$C_{25}$alkyl group;

R²² and R²³ are independently of each other hydrogen, a $C_1$-$C_{25}$alkyl group, a $C_1$-$C_{25}$alkoxy group, a $C_6$-$C_{10}$aryloxy group, or a $C_6$-$C_{10}$aryl group; preferably hydrogen.

The group of formula (Xa) is preferably a group of formula (Xa), wherein $X^1$ is O, S, C(CH₃)(CH₃), C(=O),

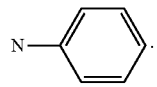

The group of formula (Xd) is preferably a group of formula (Xd), wherein R²¹ and R²¹' are hydrogen.

The group of formula (Xa) or (Xd) is more preferably a group of formula

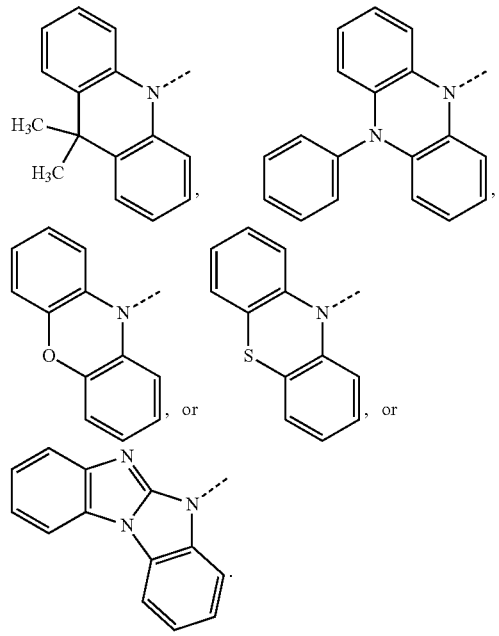

In particularly preferred compounds of formula (I) the residues have the following meanings:

R¹ and R² are independently of each other hydrogen, $C_1$-$C_{25}$alkyl group, a $C_6$-$C_{10}$aryl group, or a group of formula (Xa) or (Xd);

R⁴ is a $C_1$-$C_{25}$alkyl group, a $C_6$-$C_{10}$aryl group, or a group of formula (Xa) or (Xd);

$X^1$ is O, S, C(CH₃)(CH₃), C(=O), or

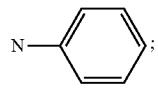

and

R¹⁰, R¹¹, R²¹ and R²¹' are independently of each other hydrogen, or a $C_1$-$C_{25}$alkyl group;

wherein at least one group of formula (Xa), or (Xd) is present in the compound of formula (I).

Specific examples of compounds of formula

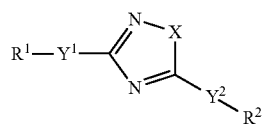

(I)

are shown below:

Specific examples of the compounds of formula (I), wherein X is N—Y⁴—R⁴ are the following compounds of formula (Ia):

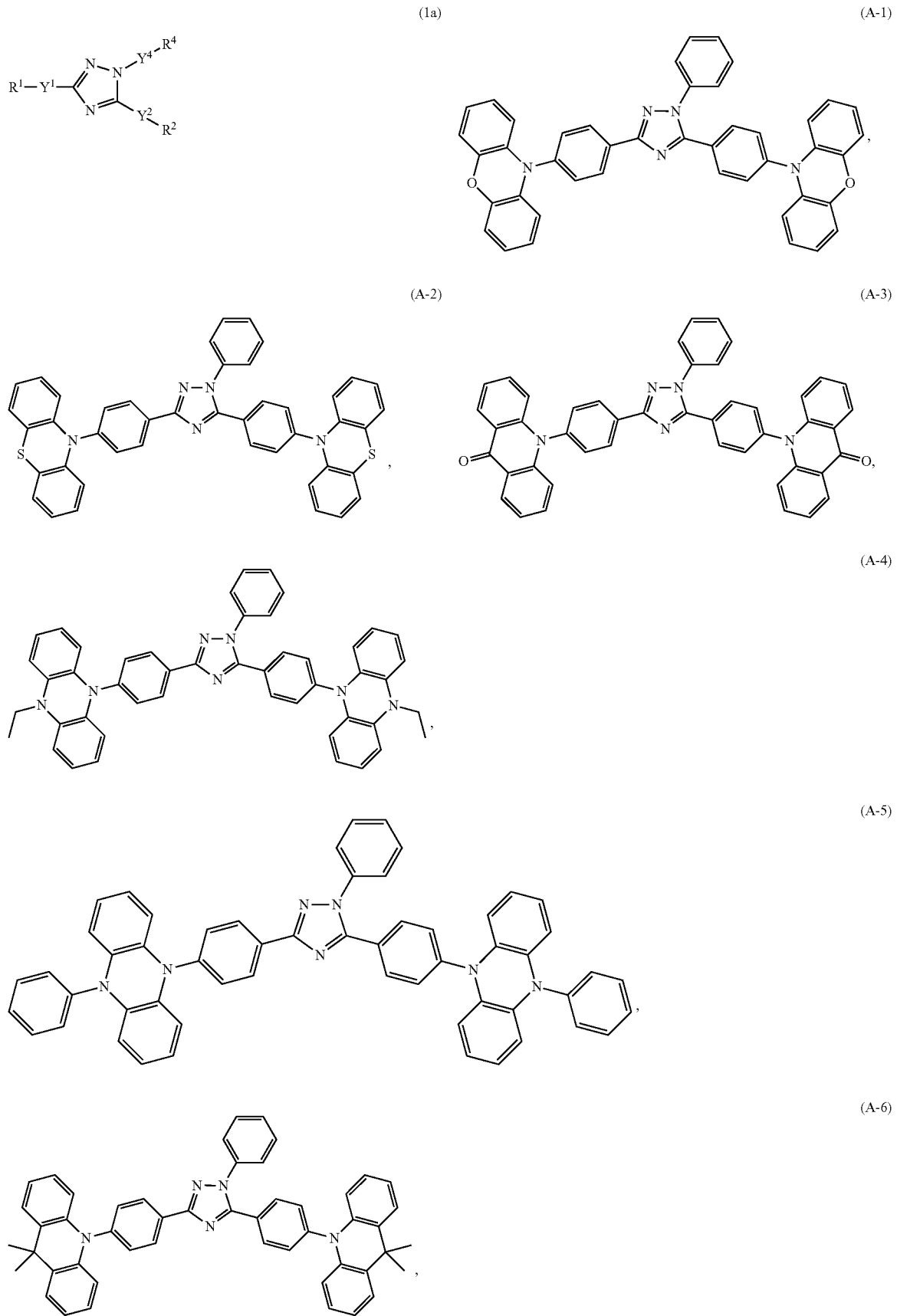

(A-7)
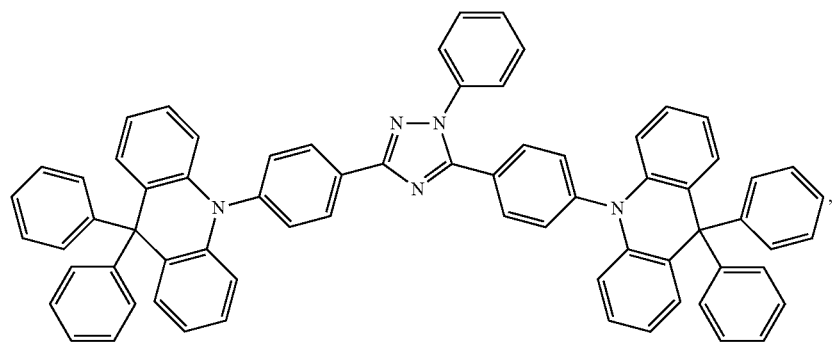
(A-8)
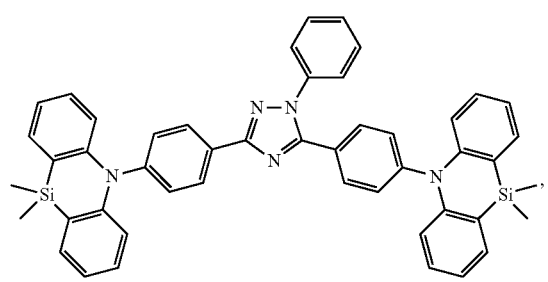
(A-9)
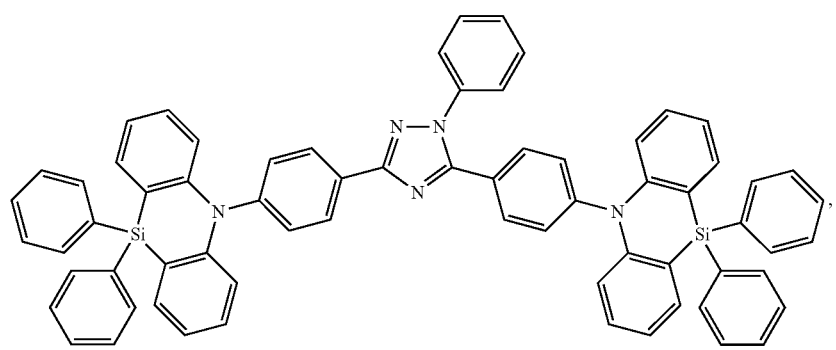
(A-10)
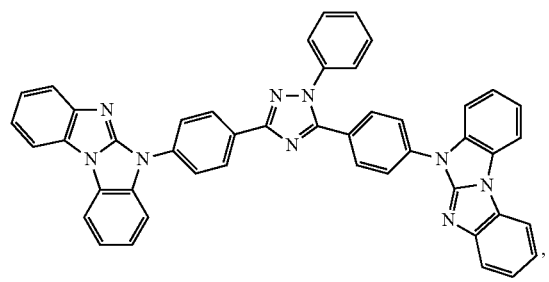
(A-11)
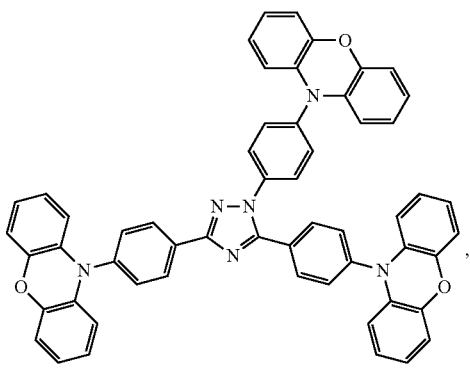

-continued
(A-12)
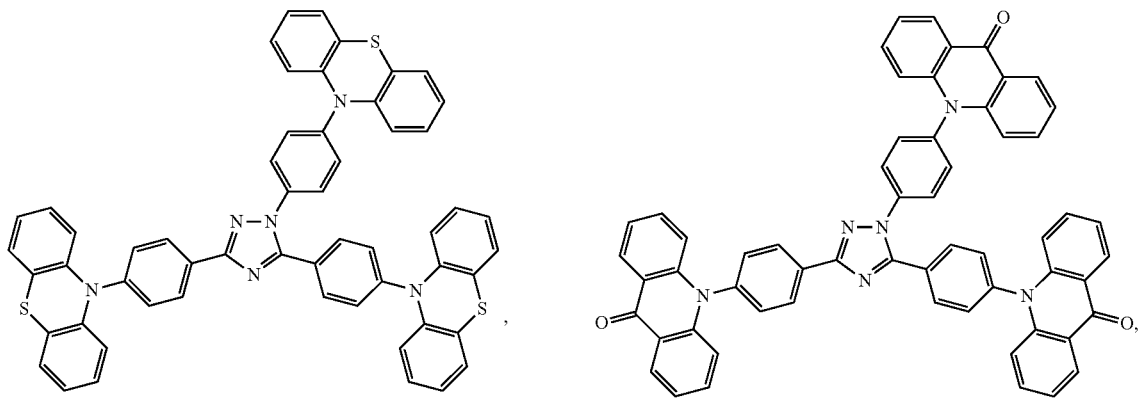
(A-13)
(A-14)
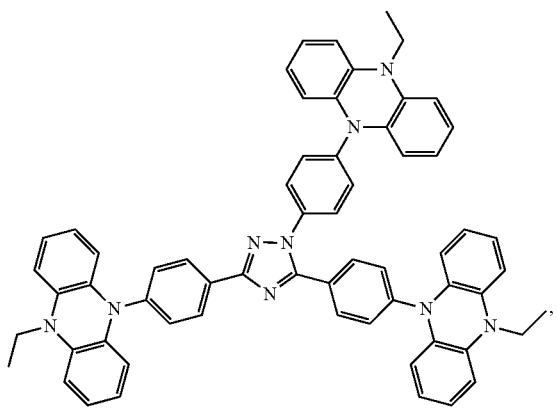
(A-15)
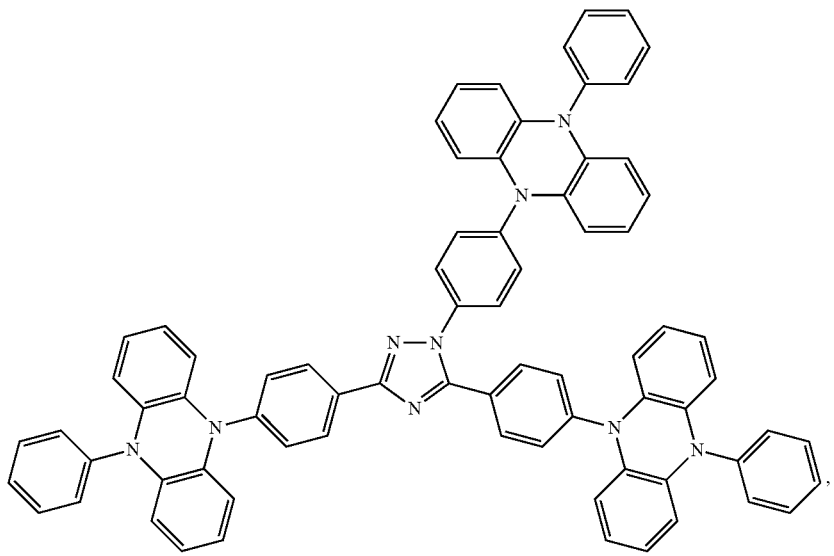

-continued
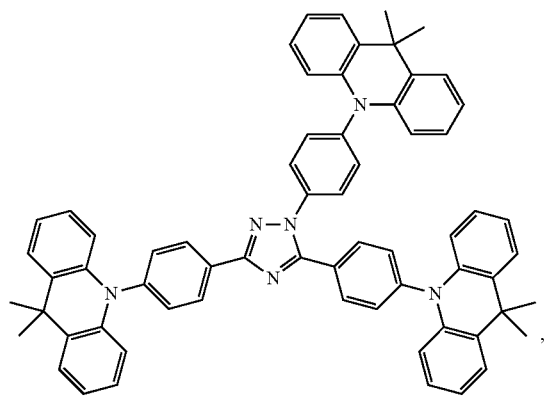
(A-16)
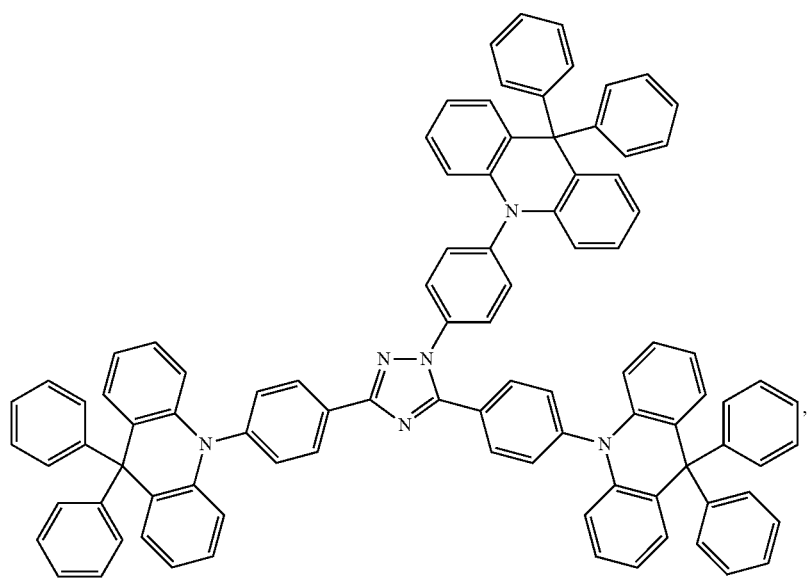
(A-17)
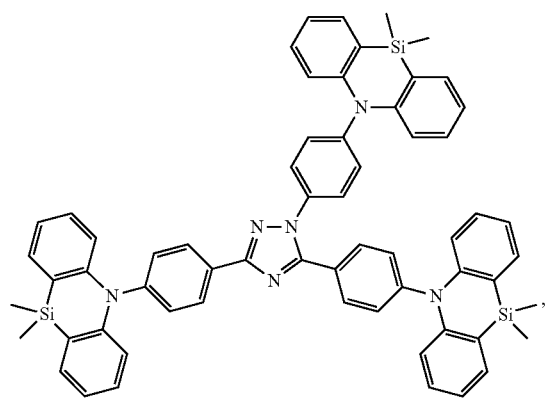
(A-18)

-continued
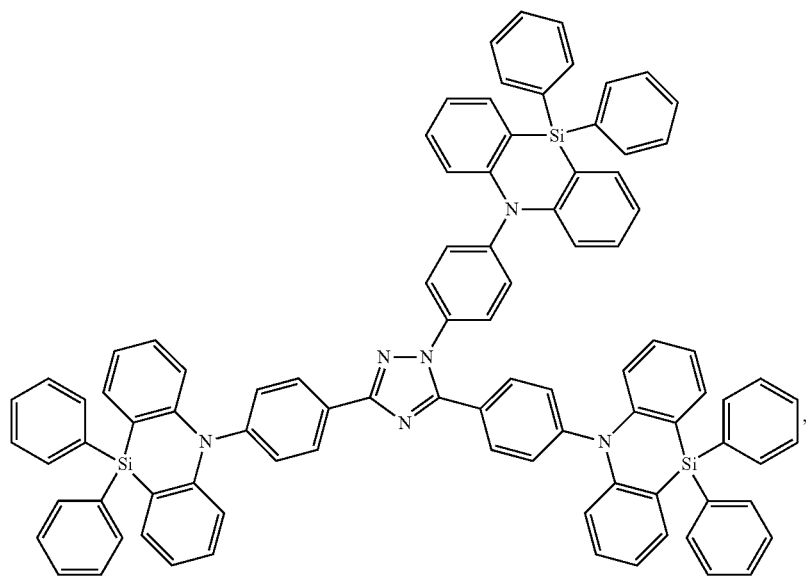
(A-19)
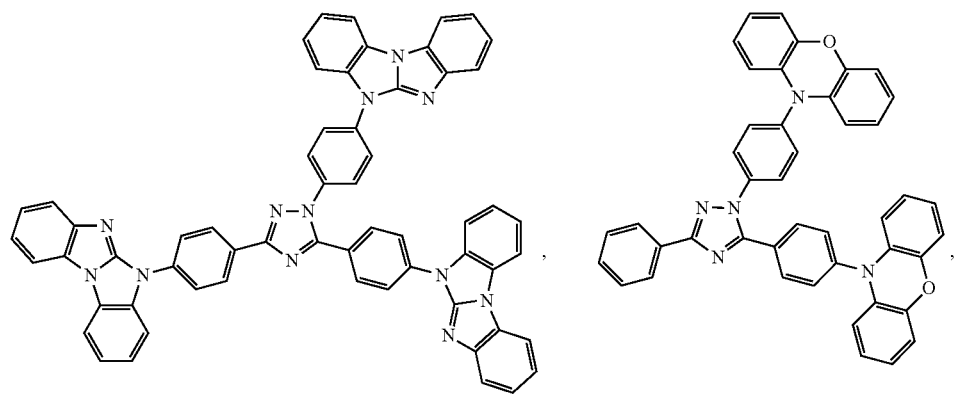
(A-20) (A-21)
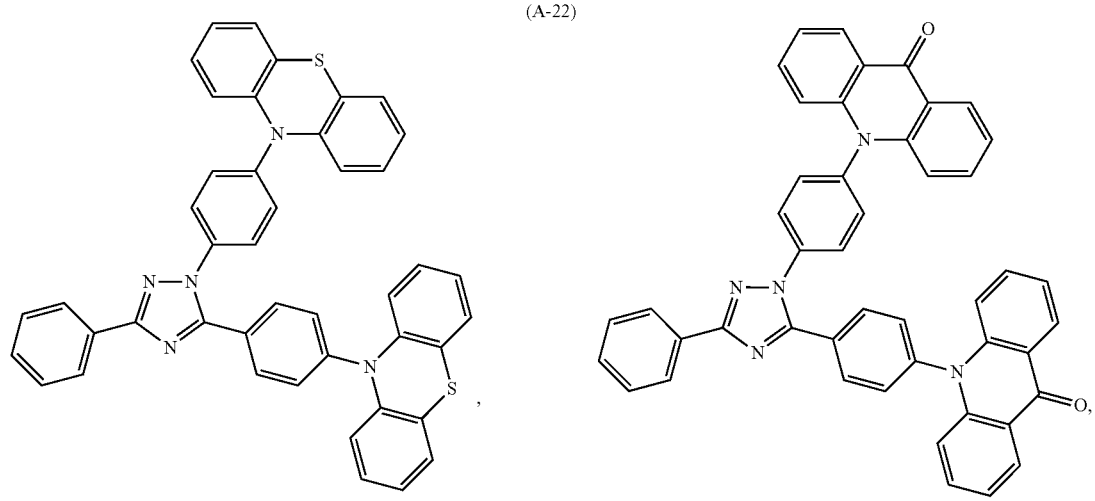
(A-22) (A-23)

-continued
(A-24)
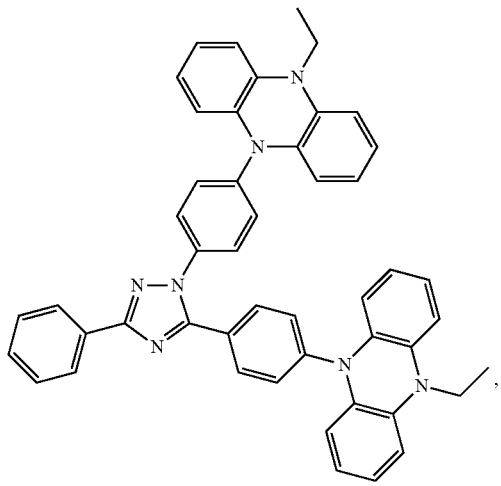
(A-25)
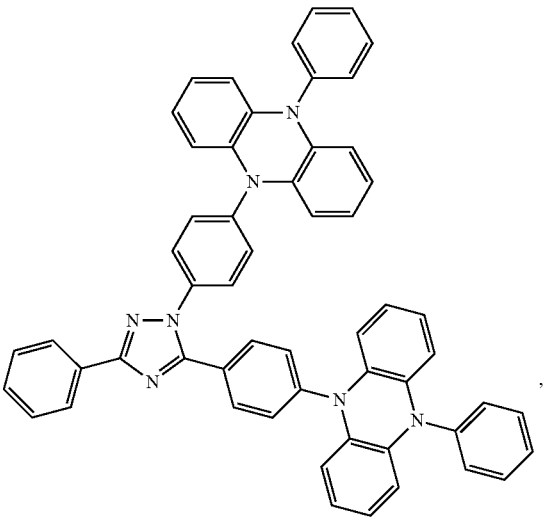
(A-26)
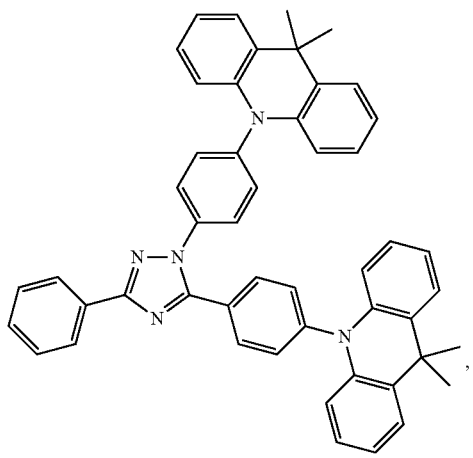
(A-27)
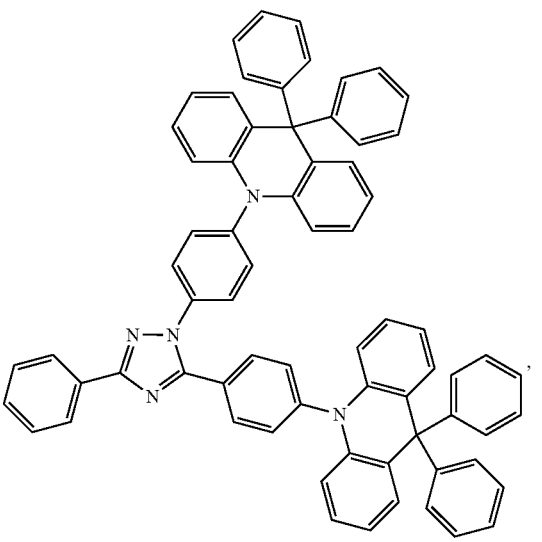
(A-28)
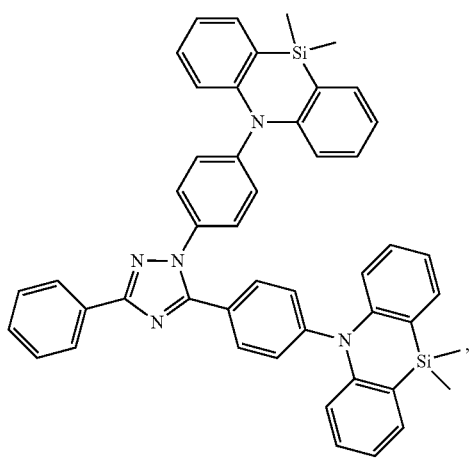
(A-29)
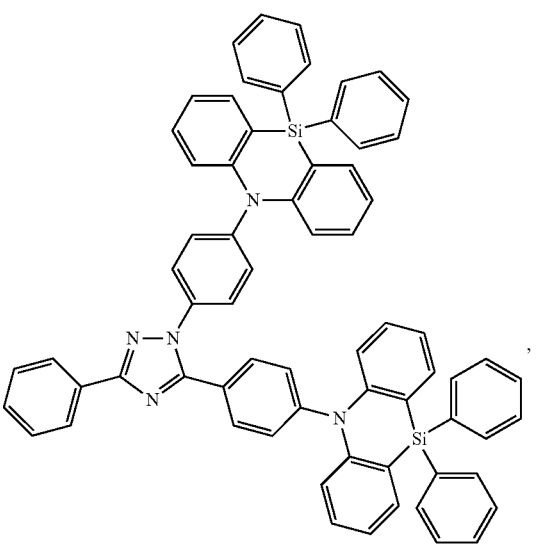

-continued
(A-30)
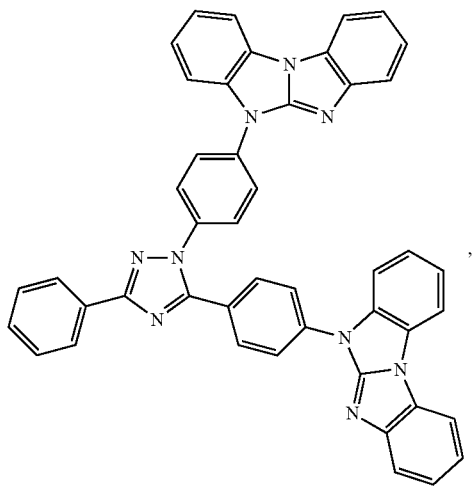
(A-31)
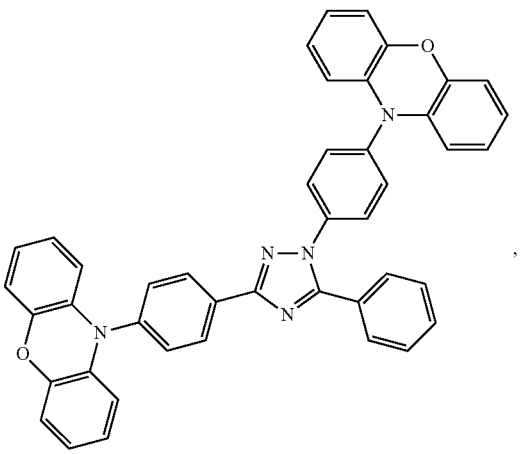
(A-32)
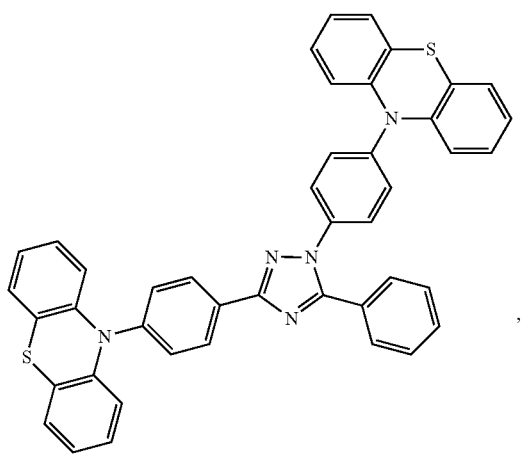
(A-33)
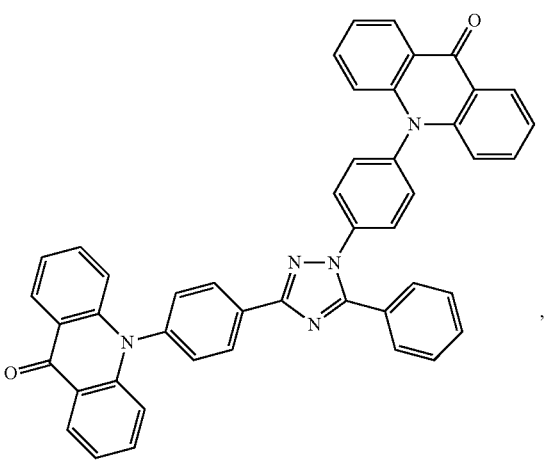
(A-34)
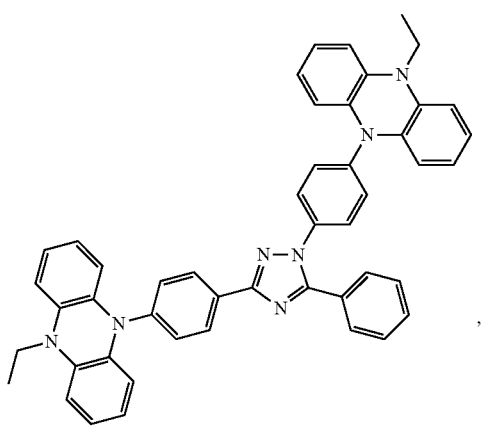
(A-35)
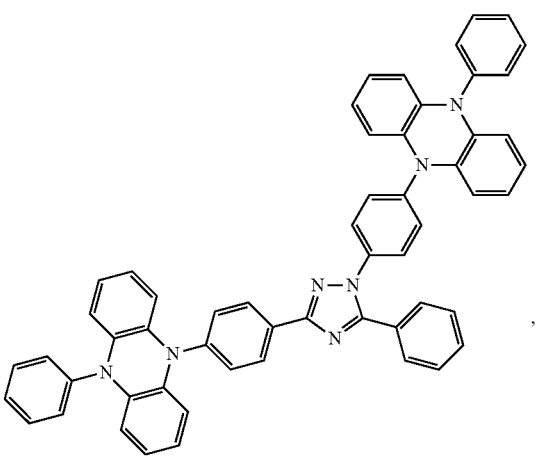

-continued
(A-36)
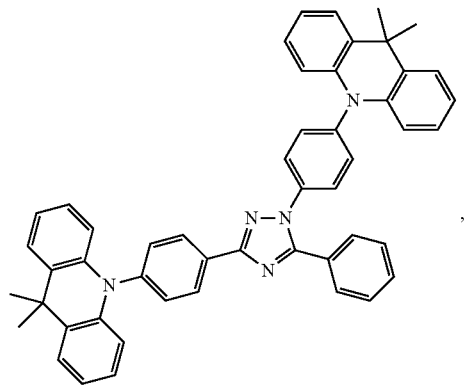
(A-37)
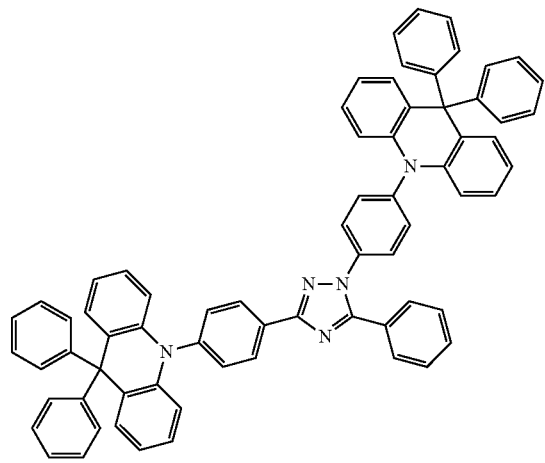
(A-38)
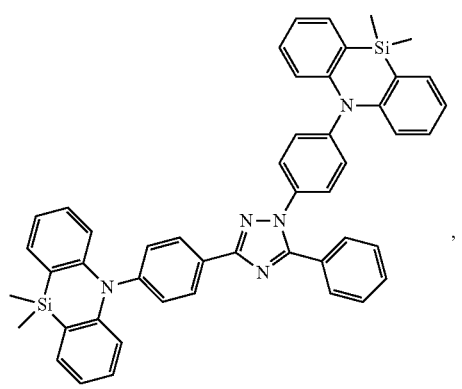
(A-39)
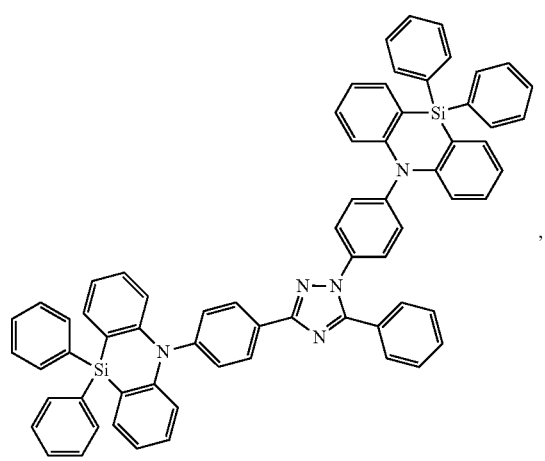
(A-40)
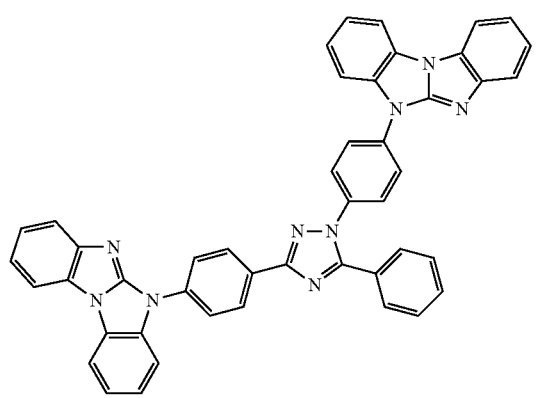
(A-41)
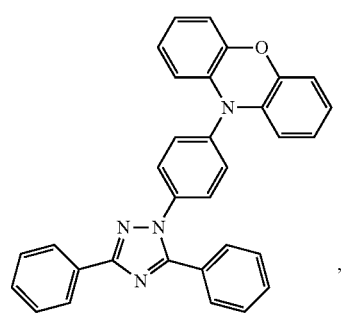

-continued
(A-42)
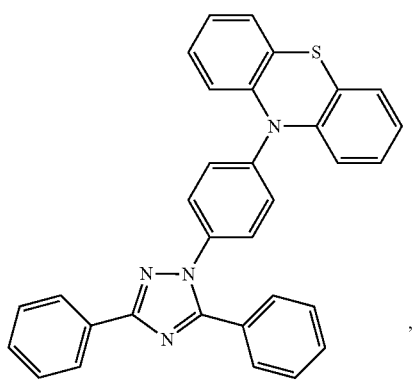
(A-43)
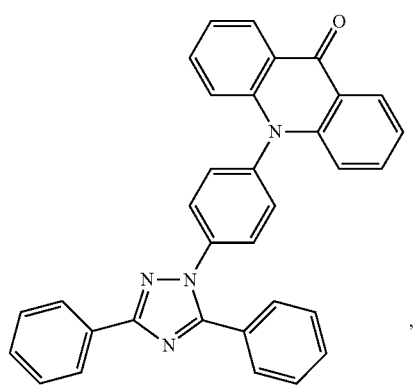
(A-44)
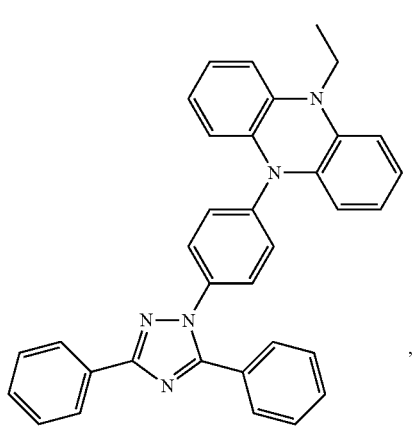
(A-45)
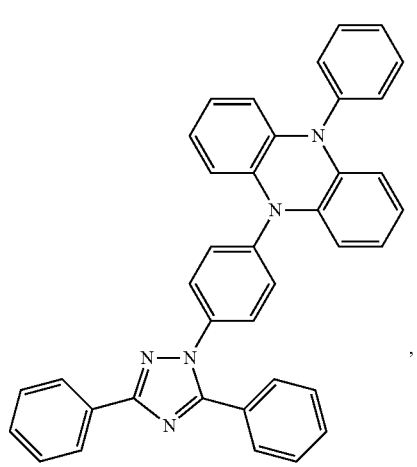
(A-46)
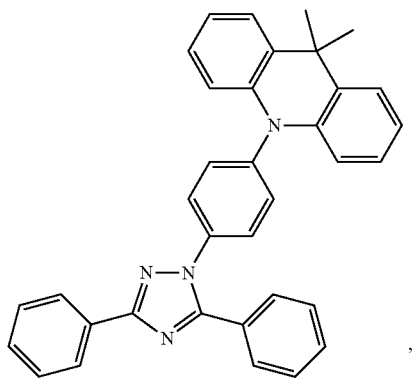
(A-47)
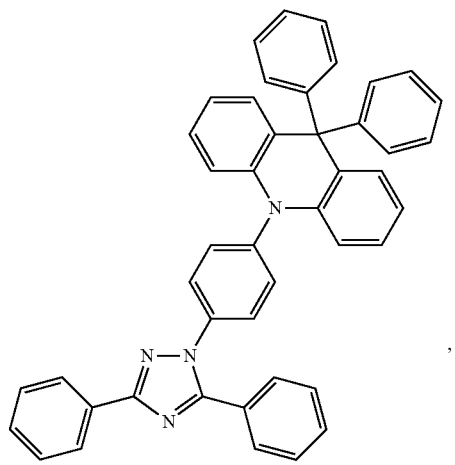

-continued
(A-48)
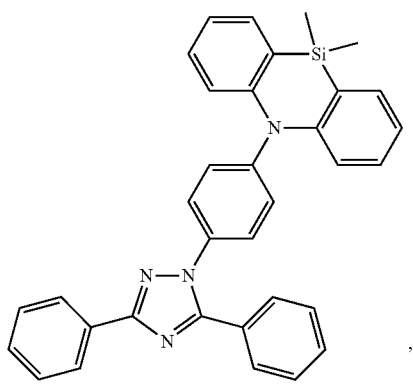
(A-49)
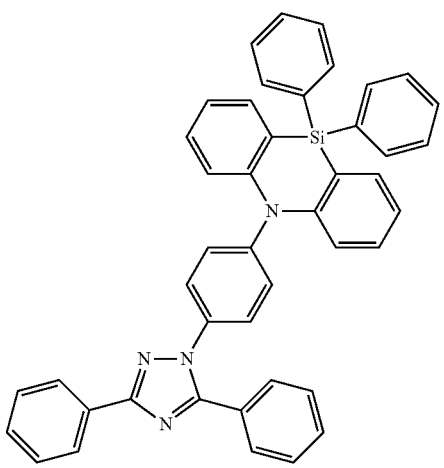
(A-50)
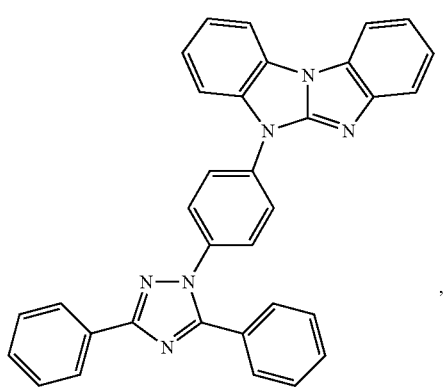
(A-51)
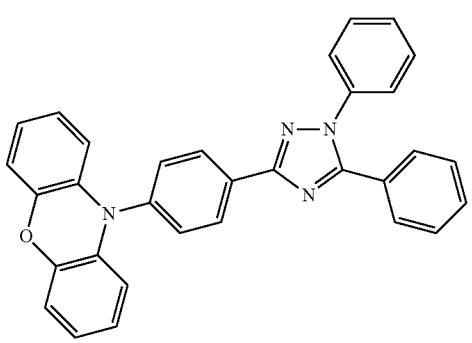
(A-52)
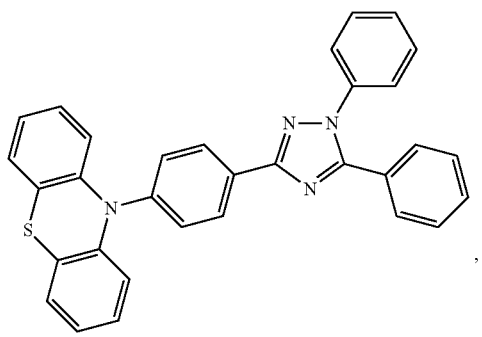
(A-53)
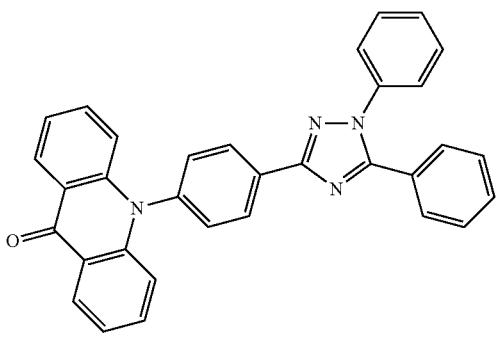
(A-54)
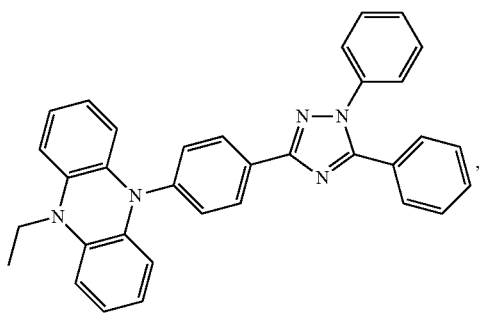
(A-55)
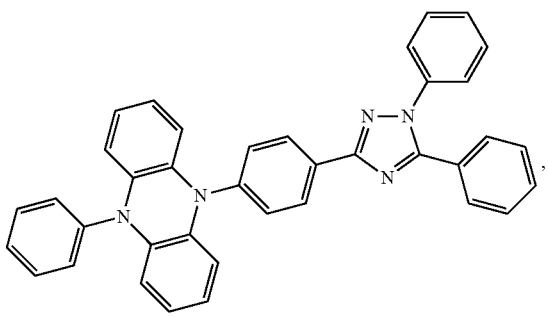

-continued
(A-56)
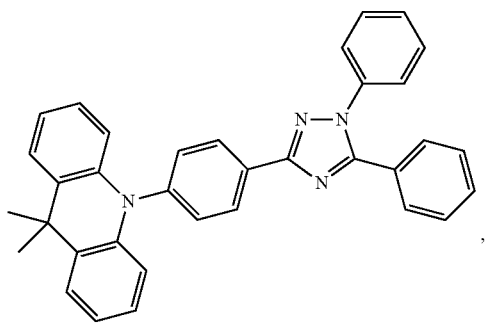
(A-57)
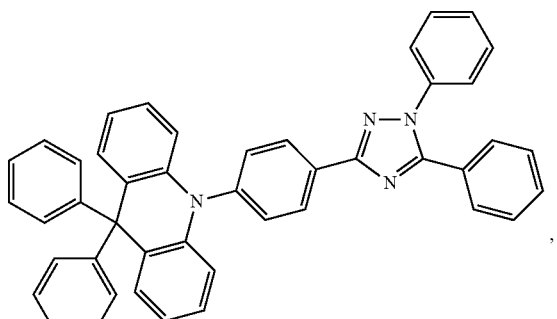
(A-58)
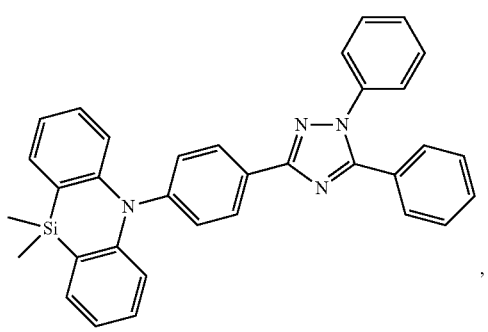
(A-59)
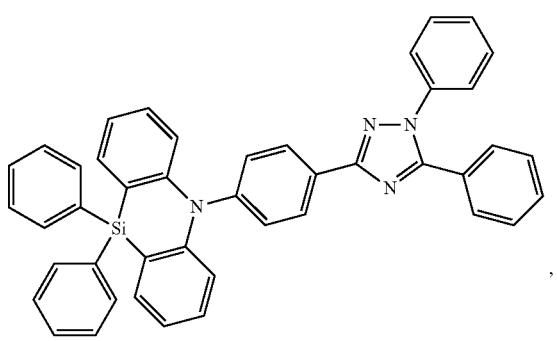
(A-60)
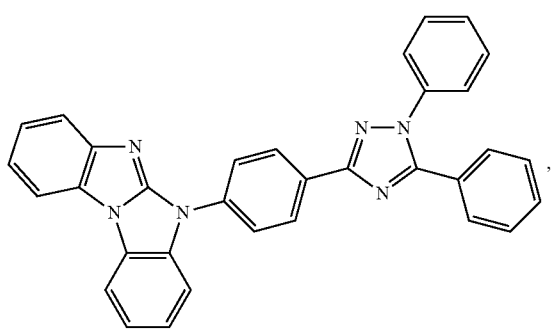
(A-61)
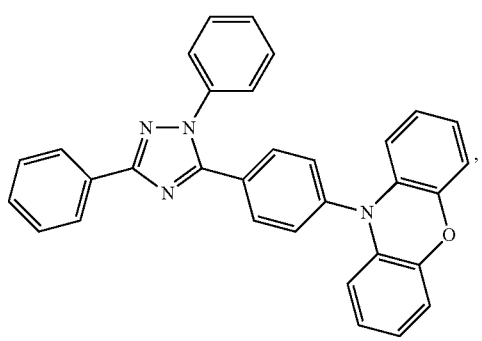
(A-62)
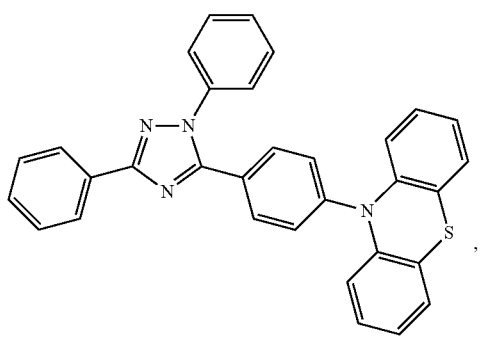
(A-63)
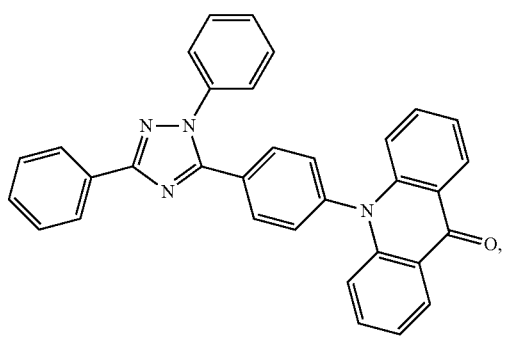

-continued
(A-64)
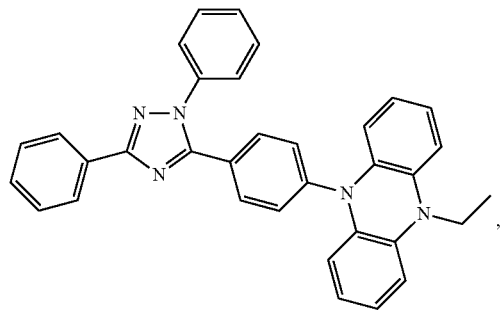
(A-65)
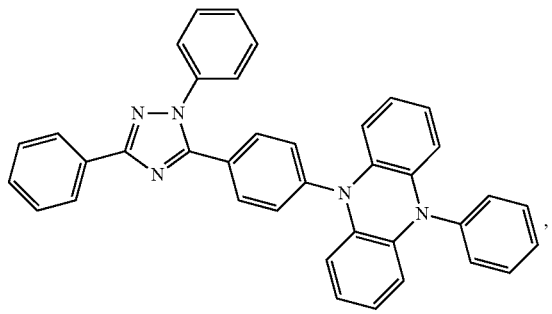
(A-66)
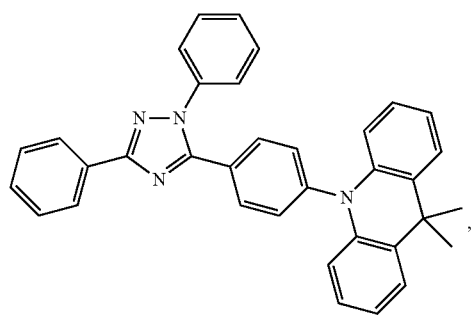
(A-67)
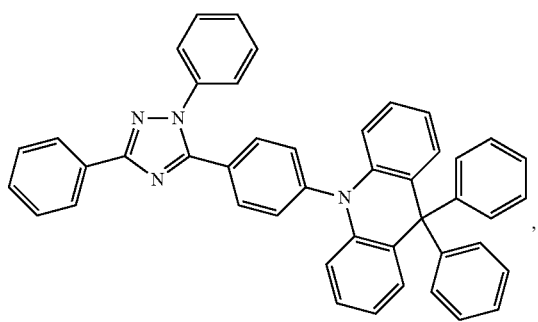
(A-68)
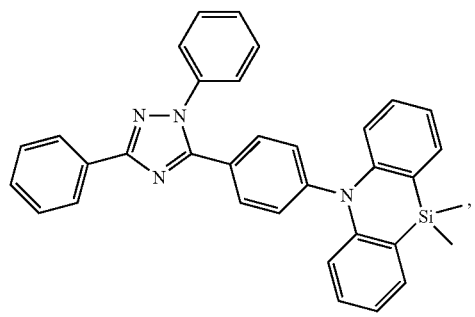
(A-69)
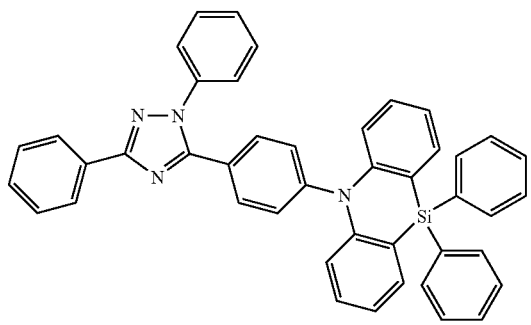
(A-70)
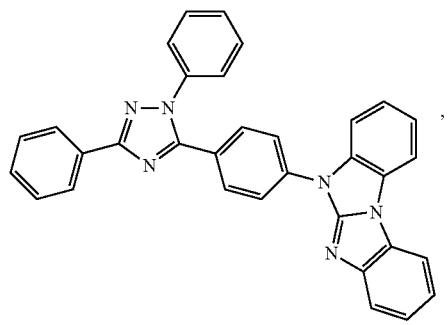
(A-71)
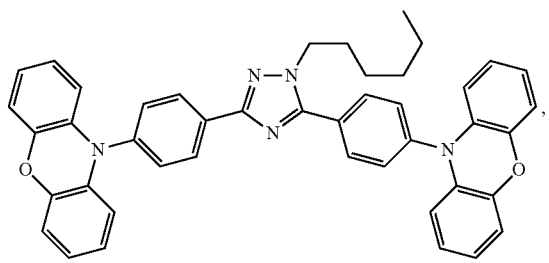

-continued
(A-72)
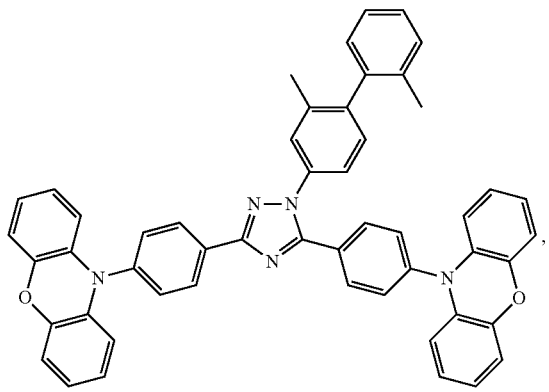
(A-73)
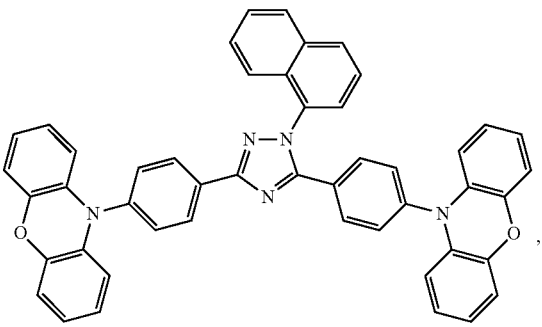
(A-74)
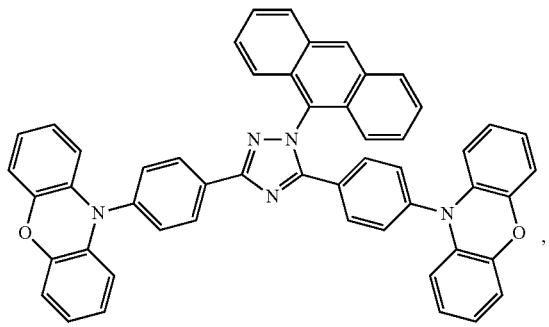
(A-75)
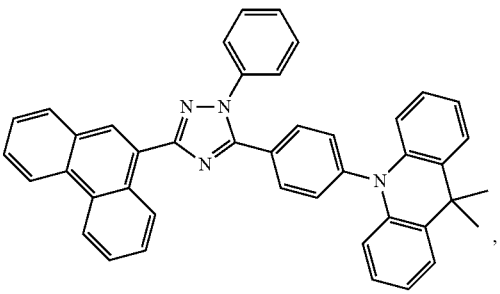
(A-76)
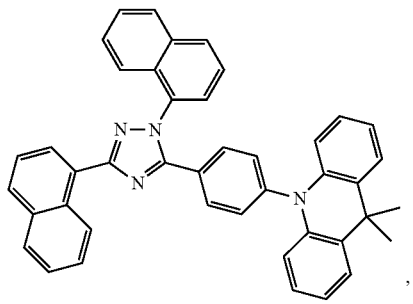
(A-77)
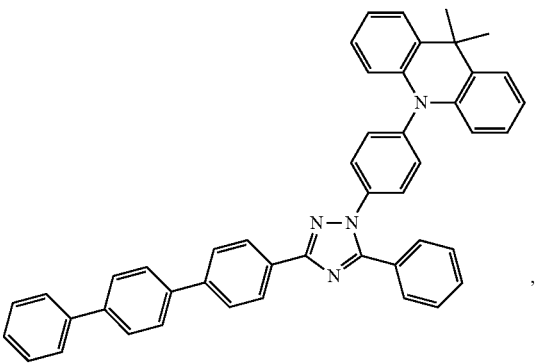
(A-78)
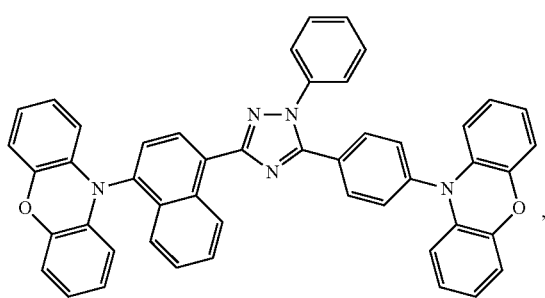

-continued
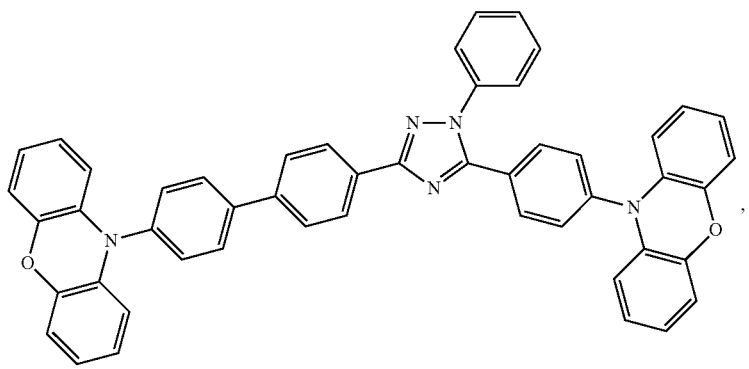
(A-79)
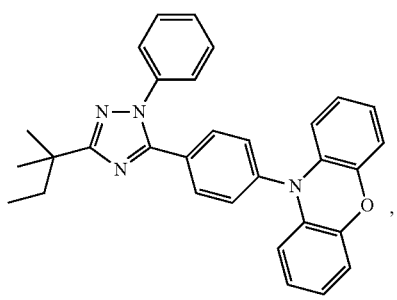
(A-80)
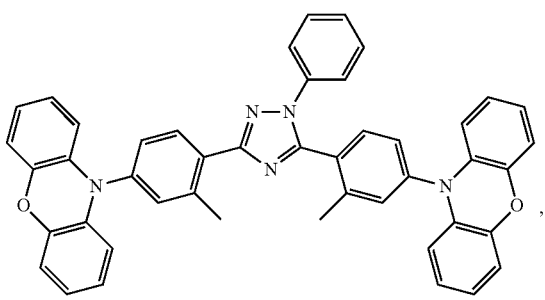
(A-81)
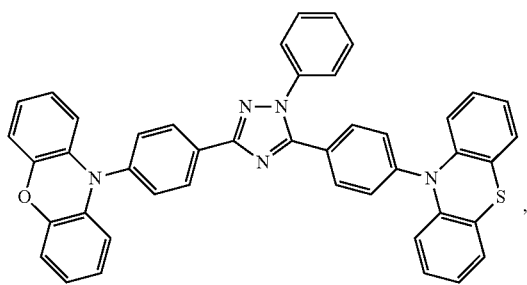
(A-82)
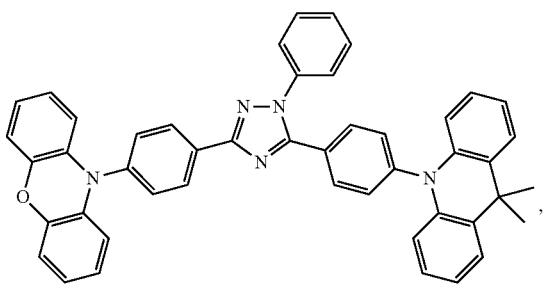
(A-83)
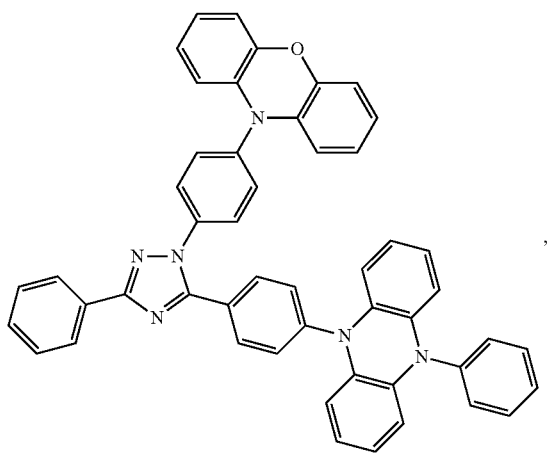
(A-84)
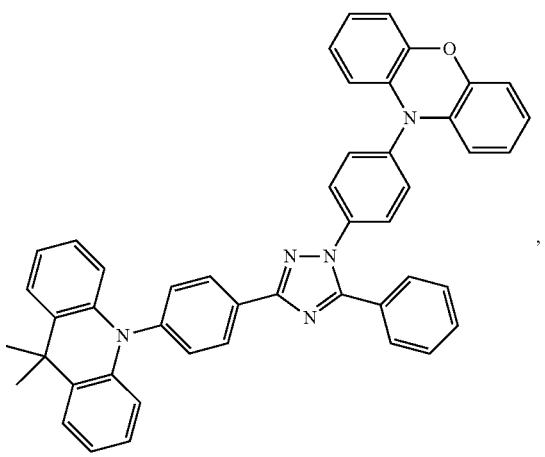
(A-85)

-continued
(A-86)
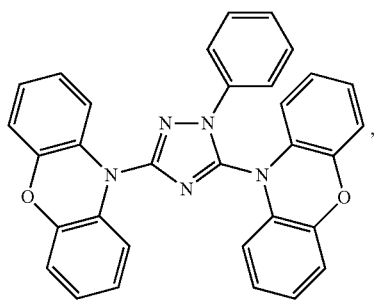
(A-87)
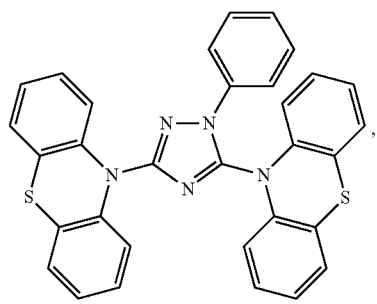
(A-88)
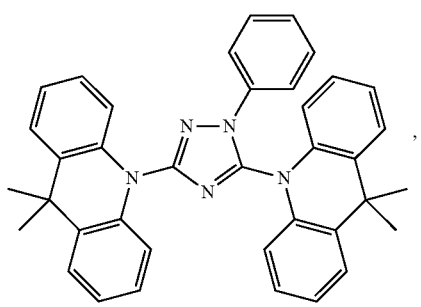
(A-89)
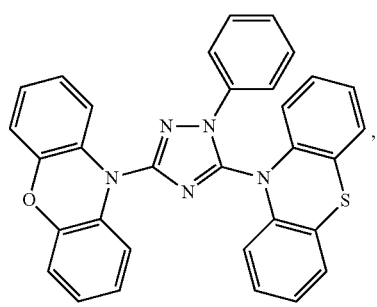
(A-90)
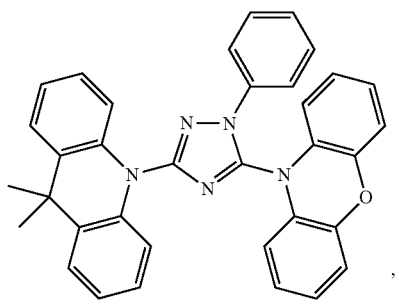
(A-91)
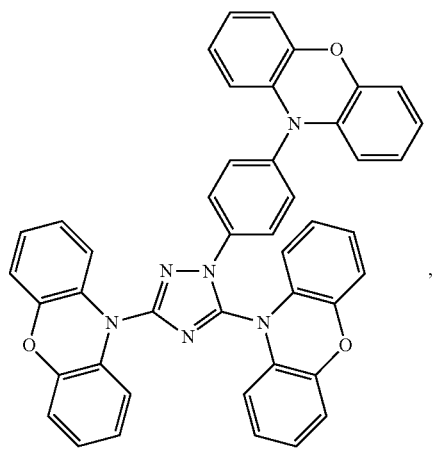
(A-92)
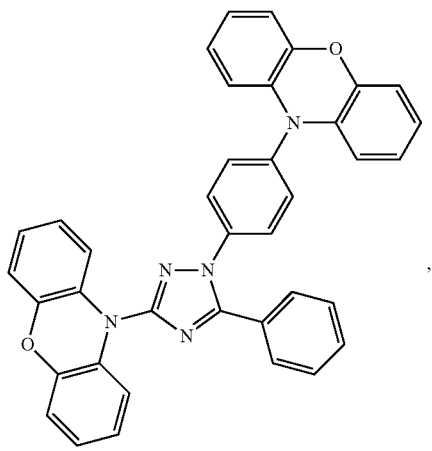
(A-93)
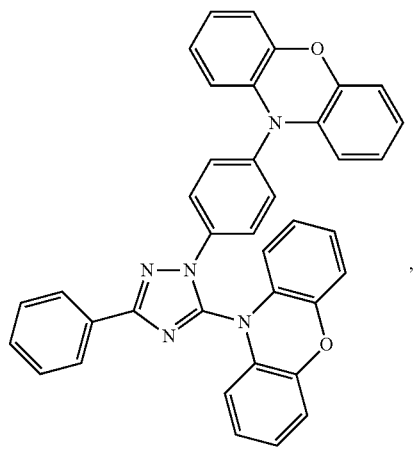

-continued
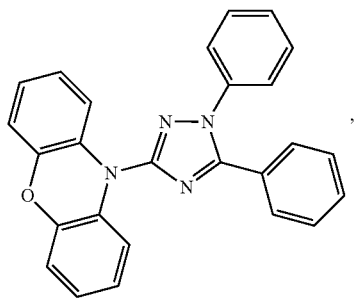
(A-94)
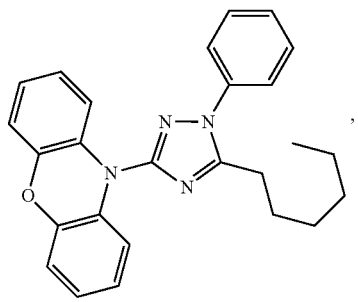
(A-95)
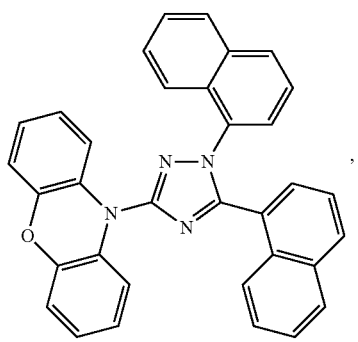
(A-96)
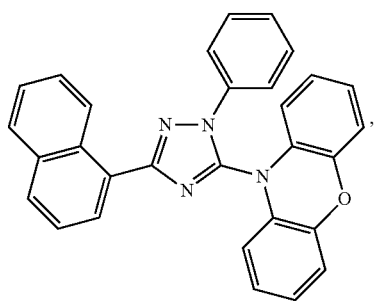
(A-97)
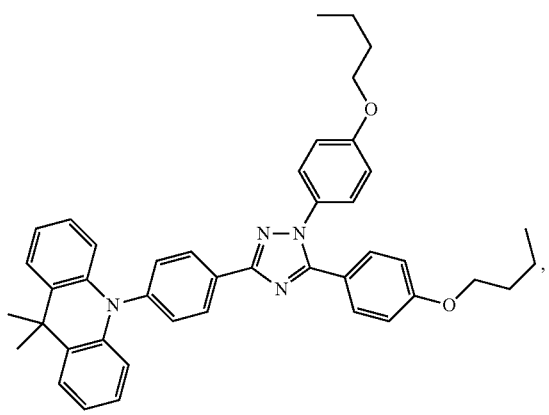
(A-98)
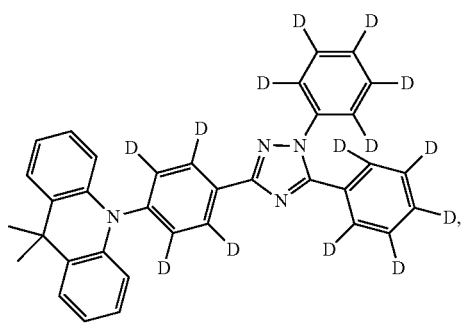
(A-99)
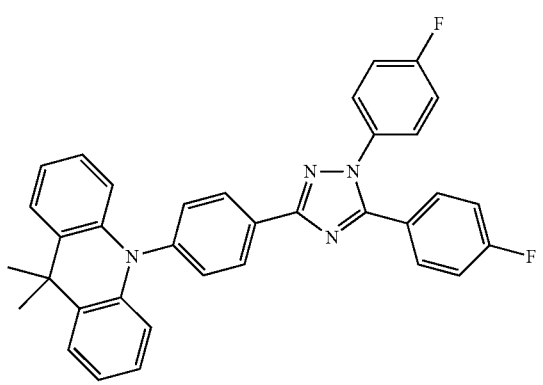
(A-100)

Among compounds of formula (Ia) those are preferred which are substituted especially by groups (Xa) and/or (Xd) of formula

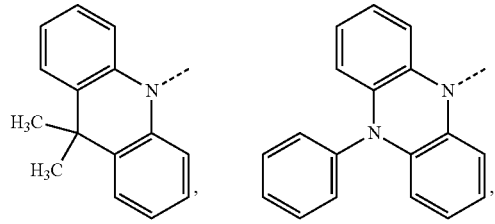

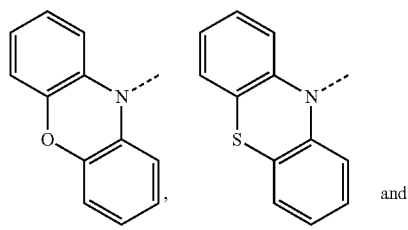 and

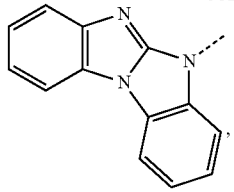

such as, for example, compounds (A-1), (A-2), (A-5), (A-6), (A-10), (A-11), (A-12), (A-15), (A-16), (A-20), (A-21), (A-22), (A-25), (A-26), (A-30), (A-31), (A-32), (A-35), (A-36), (A-40), (A-41), (A-42), (A-45), (A-46), (A-50), (A51), (A-52), (A-55), (A-56), (A-60), (A-61), (A-62), (A-65), (A-66), (A-70), (A-71), (A-72), (A-73), (A-75), (A-76), (A-78), (A-81) (A-82), (A-83), (A-84), (A-85), (A-86), (A-87), (A-88), (A-89), (A90), (A-91), (A-92), (A-93), (A-94), (A-99), and (A-100).

The most preferred examples are (A-1), (A-2), (A-5), (A-6), (A-11), (A-12), (A-15), (A-16), (A21), (A-22), (A-25), (A-26), (A-31), (A-32), (A-35), (A-36), (A-41), (A-42), (A-45), (A-46), (A-51), (A-52), (A-55), (A-56), (A-61), (A-62), (A-65), (A-66), (A-72), (A-73), (A-76), (A-82), (A-83), (A84) and (A-85).

Specific examples of the compounds of formula (I), wherein X is O are the following compounds of formula (Ib):

(Ib)

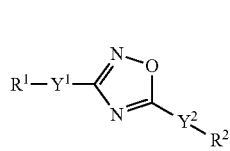

(B-1)

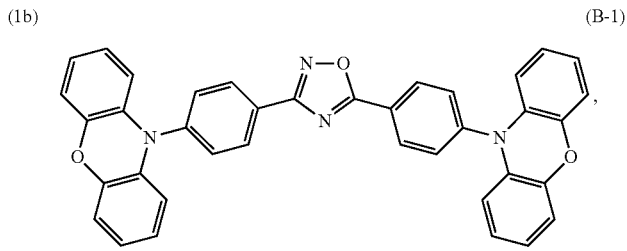

(B-2)

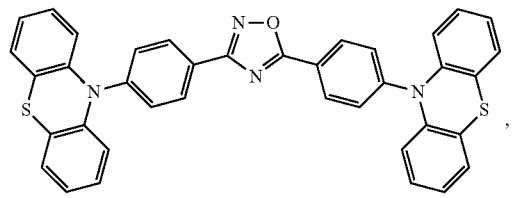

(B-3)

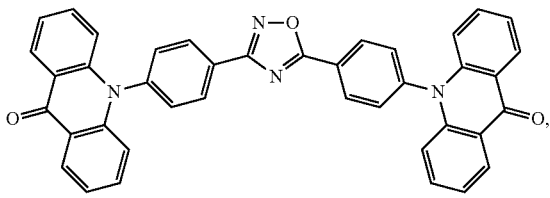

(B-4)

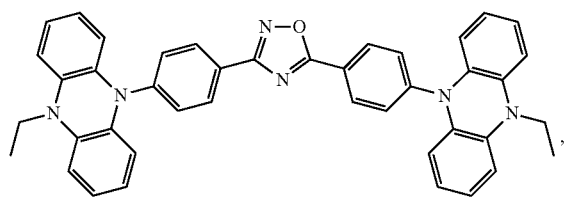

(B-5)

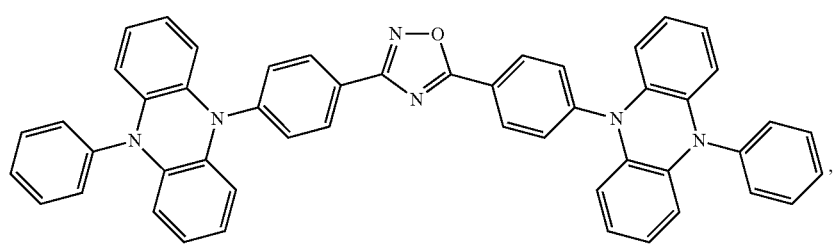

-continued
(B-6)
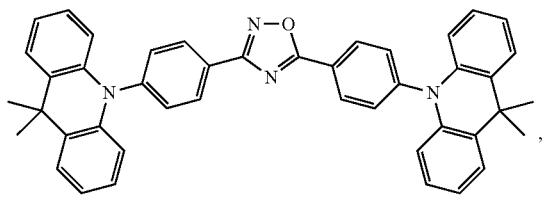
(B-7)
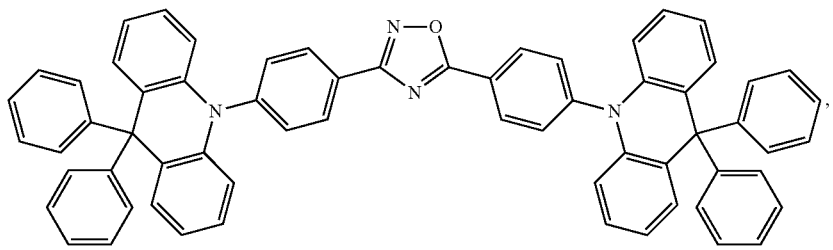
(B-8)
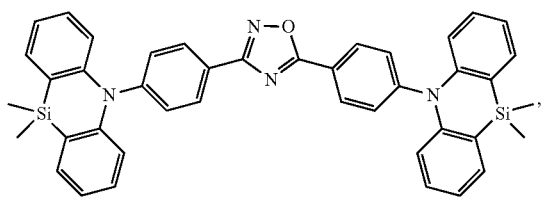
(B-9)
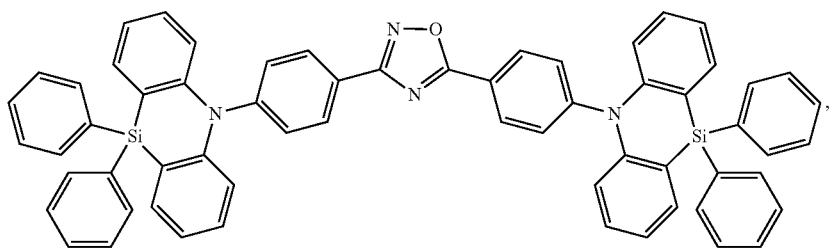
(B-10)
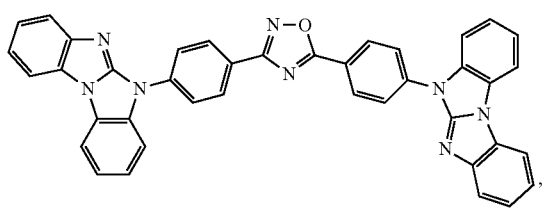
(B-21)
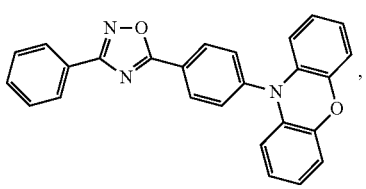
(B-22)
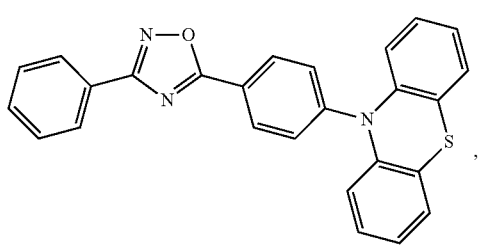
(B-23)
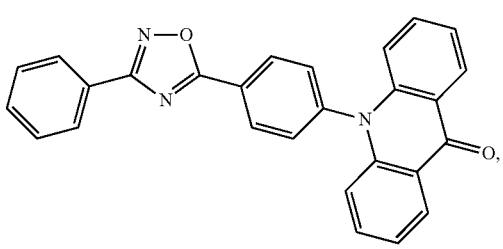
(B-24)
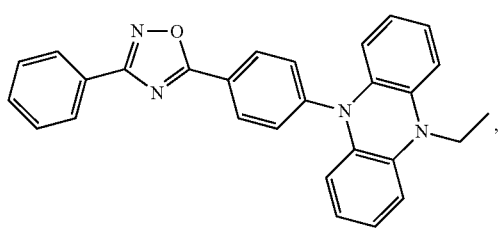
(B-25)
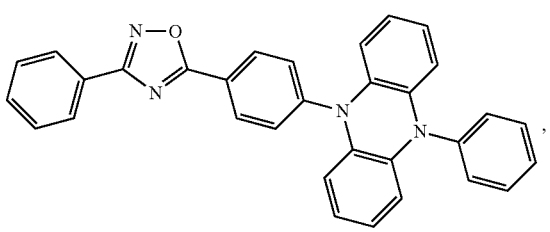

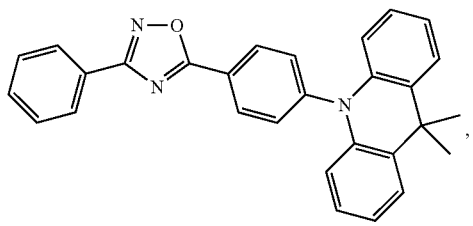
(B-26)
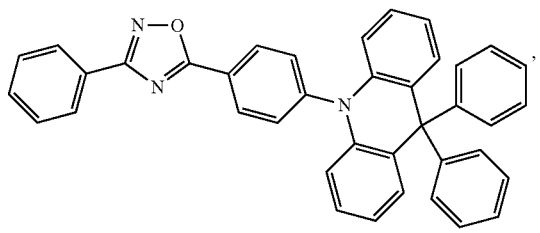
(B-27)
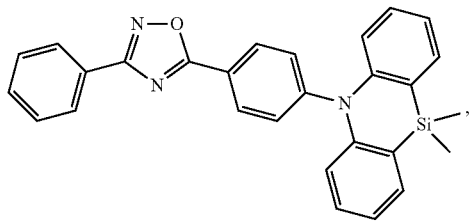
(B-28)
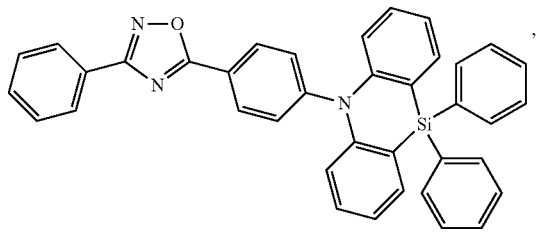
(B-29)
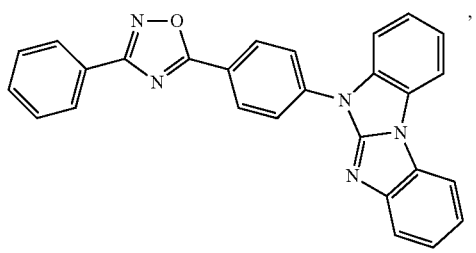
(B-30)
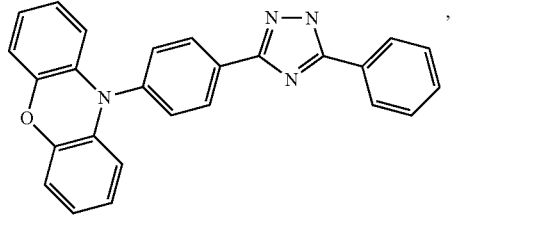
(B-31)
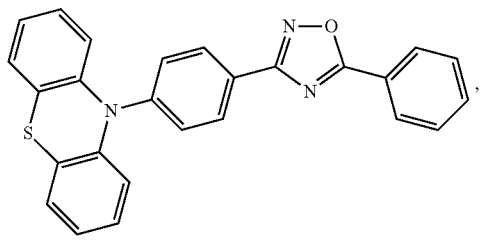
(B-32)
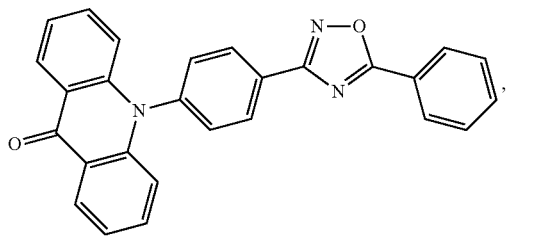
(B-33)
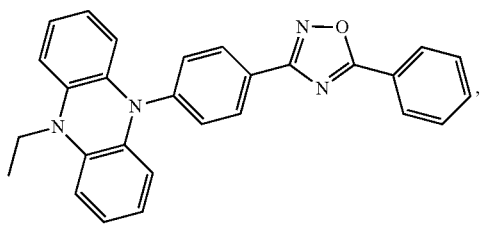
(B-34)
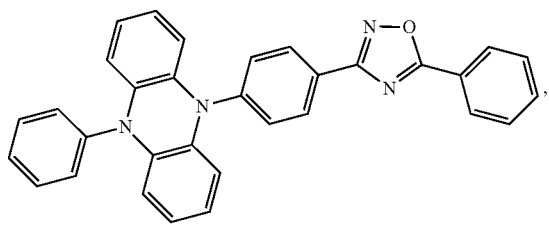
(B-35)
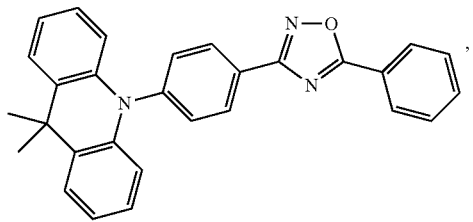
(B-36)
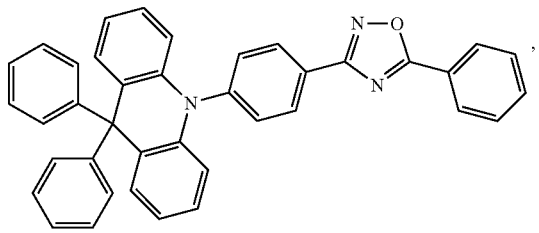
(B-37)

(B-38) 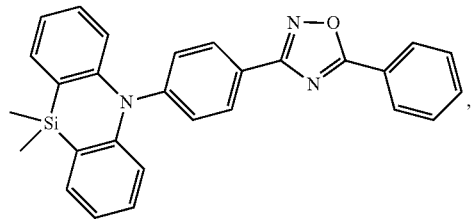
(B-39) 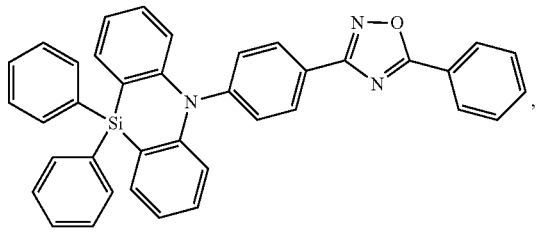
(B-40) 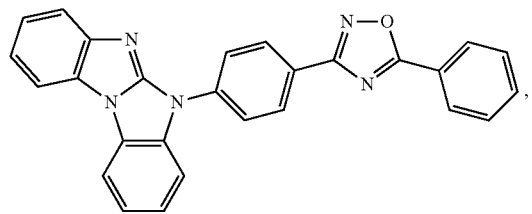
(B-75) 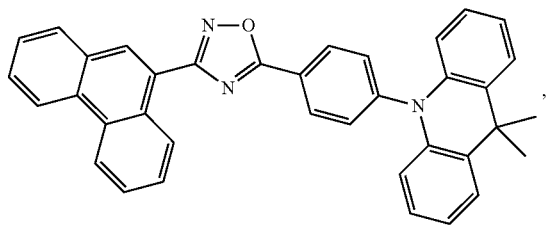
(B-76) 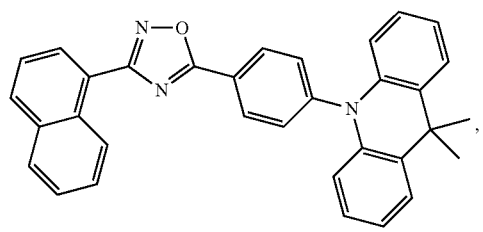
(B-77) 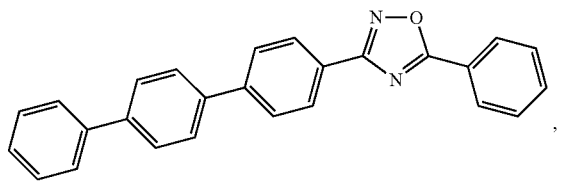
(B-78) 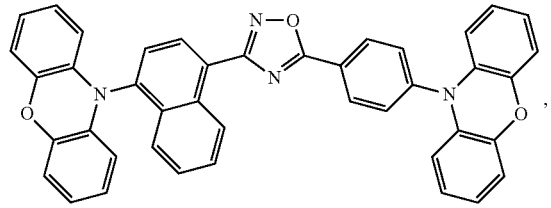
(B-79) 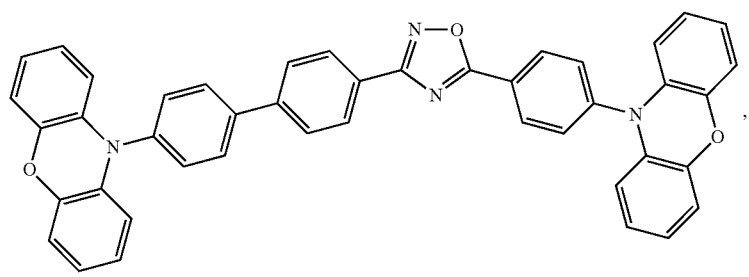
(B-80) 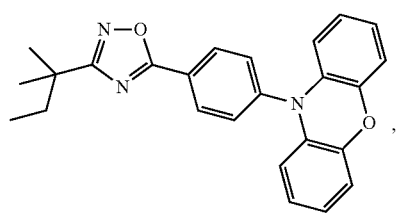
(B-81) 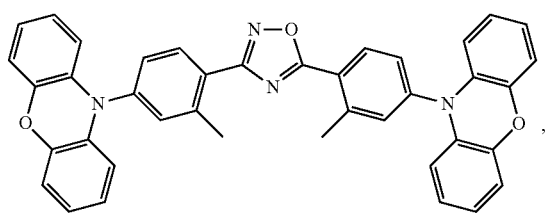

(B-82)
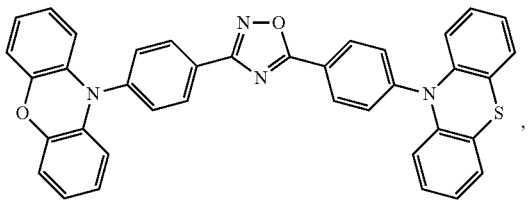
(B-83)
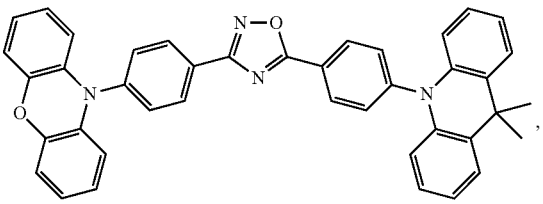
(B-84)
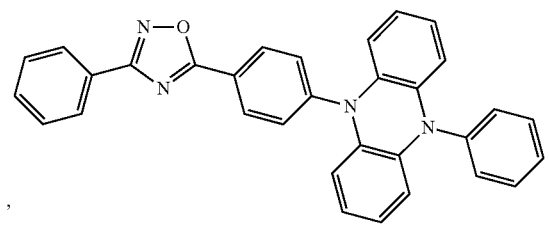
(B-85)
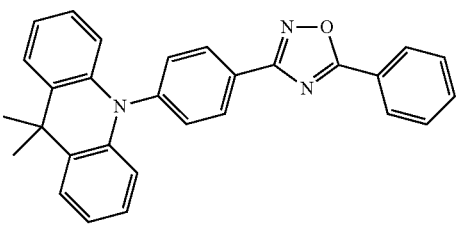
(B-86)
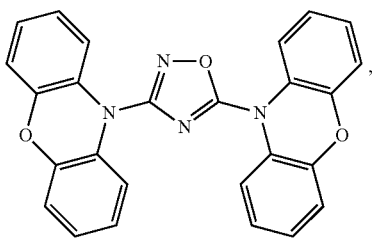
(B-87)
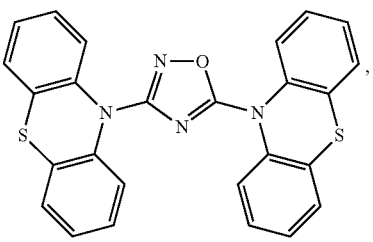
(B-88)
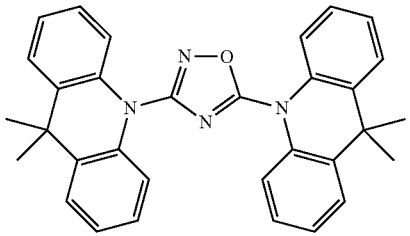
(B-89)
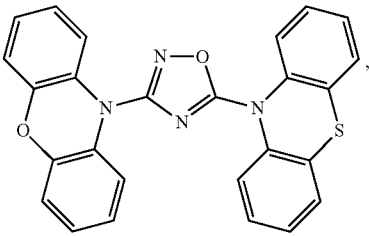
(B-90)
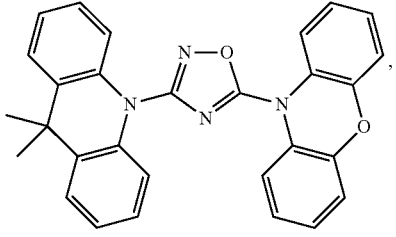
(B-92)
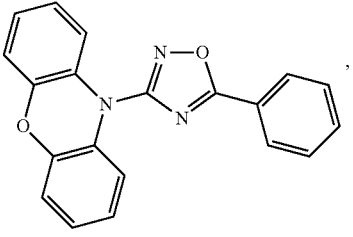
(B-93)
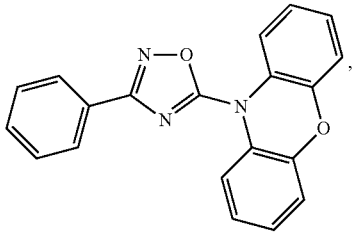
(B-95)
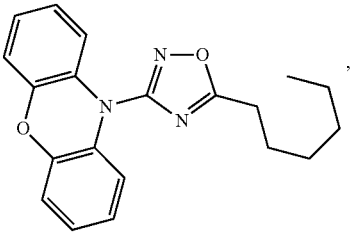

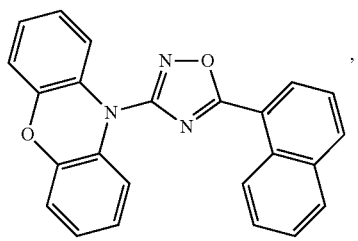
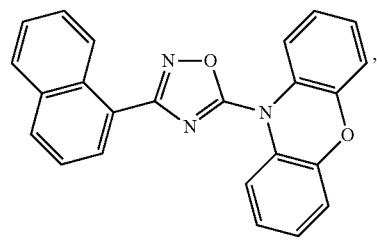
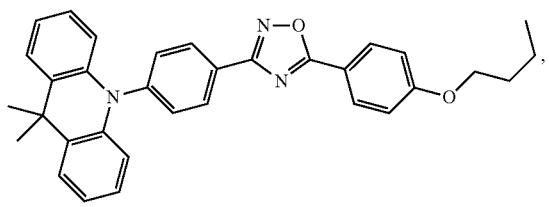
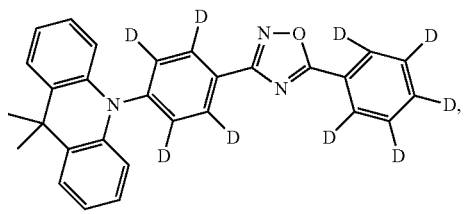
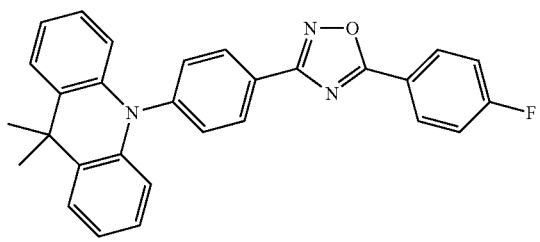
Among compounds of formula (Ib) those are preferred which are substituted especially by donor groups of formula
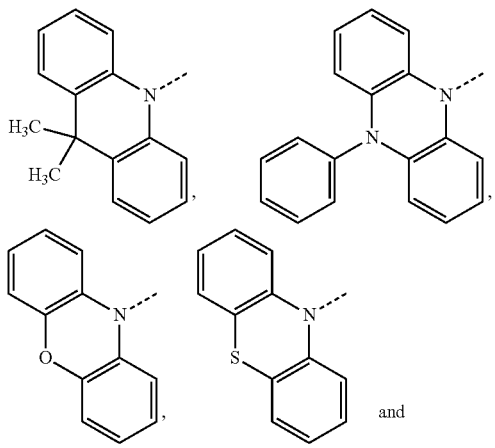
and
-continued
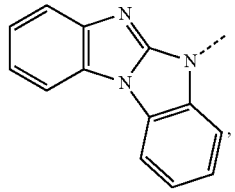
such as, for example, compounds (B-1), (B-2), (B-5), (B-6), (B-10), (B-21), (B-22), (B-25), (B-26), (B-30), (B-31), (B-32), (B-35), (B-36), (B-40), (B-75), (B-76), (B-78), (B-81), (B-82), (B-83), (B-86), (B-87), (B-88), (B-89), (B-90), (B-92), (B-93), (B-99), and (B-100).
The most preferred examples are (B-1), (B-2), (B-5), (B-6), (B-21), (B-22), (B-25), (B-26), (B-31), (B-32), (B-35), (B-36), (B-76), (B-82) and (B-83).
Specific examples of the compounds of formula (I), wherein X is O are the following compounds of formula (Ic):
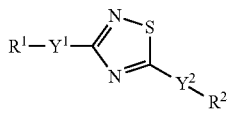
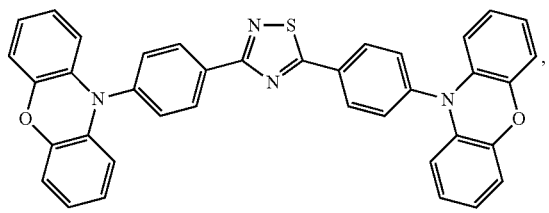

-continued
(C-2)
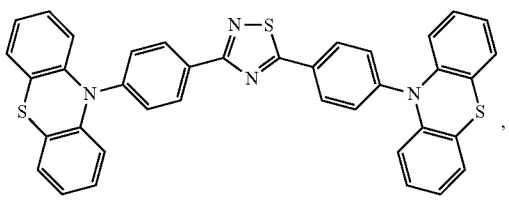
(C-3)
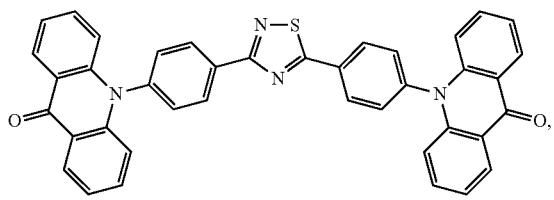
(C-4)
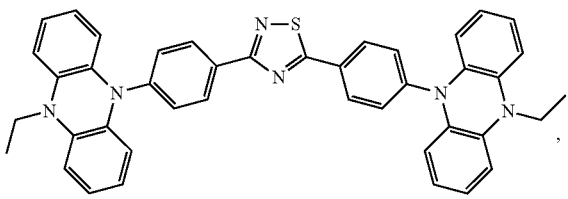
(C-5)
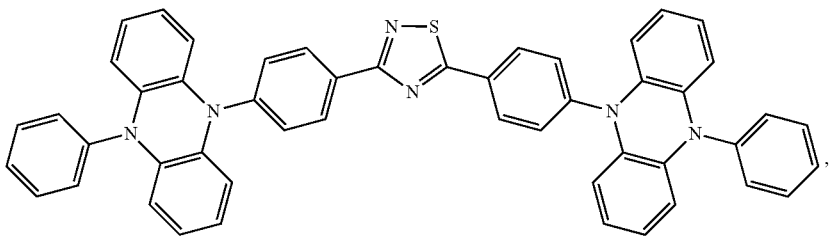
(C-6)
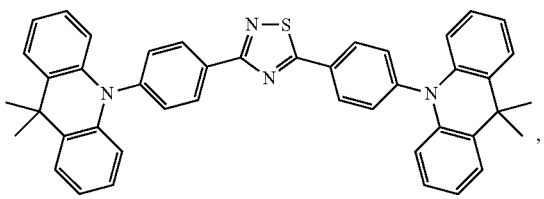
(C-7)
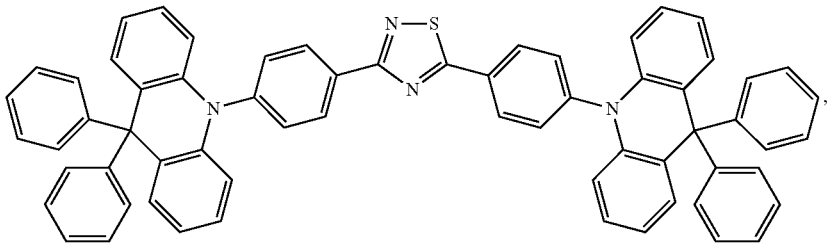
(C-8)
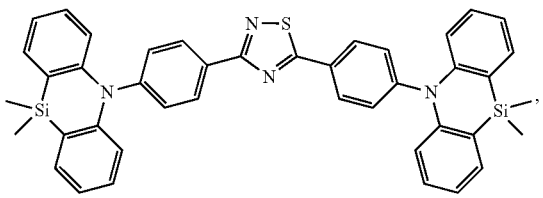
(C-9)
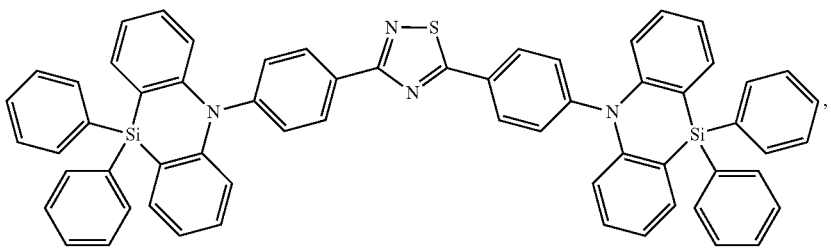

-continued
(C-10) 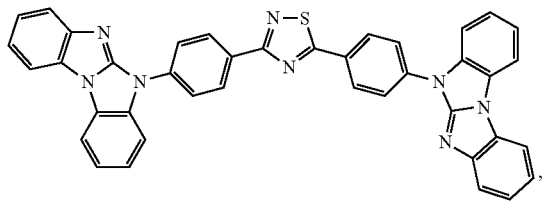
(C-21) 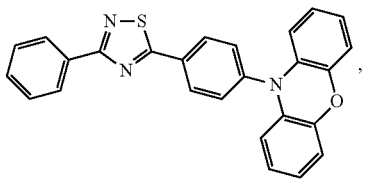
(C-22) 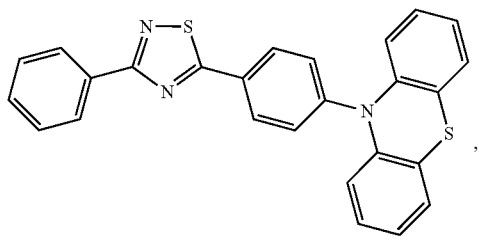
(C-23) 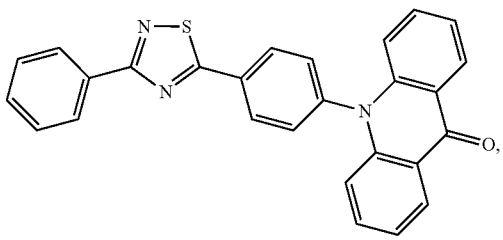
(C-24) 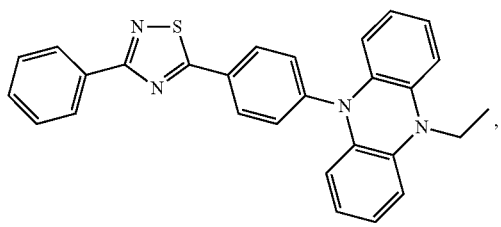
(C-25) 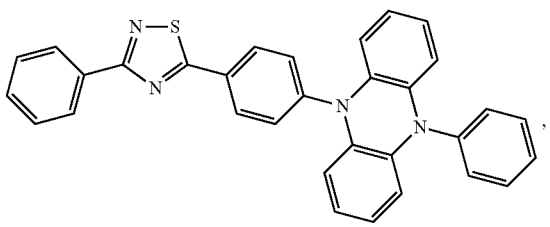
(C-26) 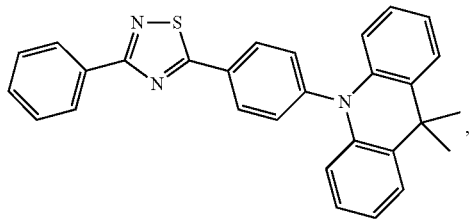
(C-27) 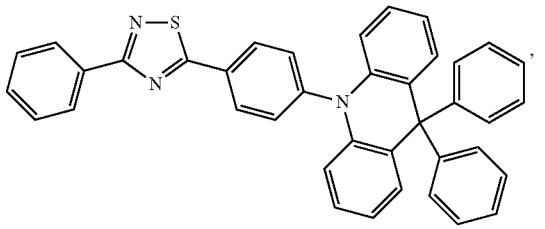
(C-28) 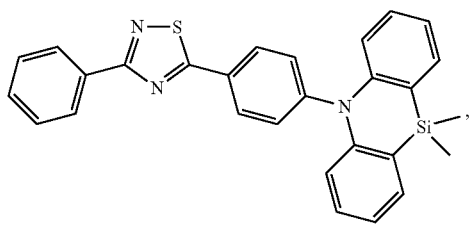
(C-29) 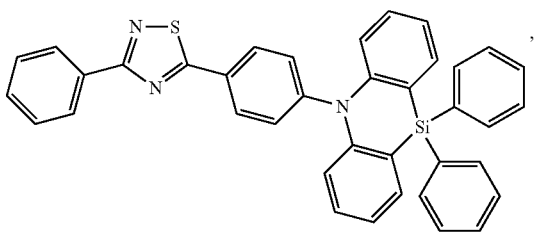
(C-30) 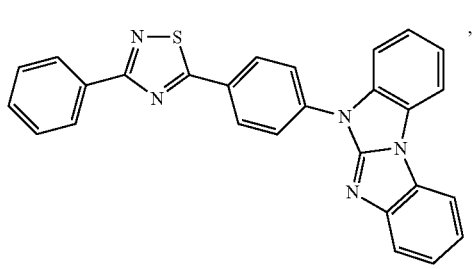
(C-31) 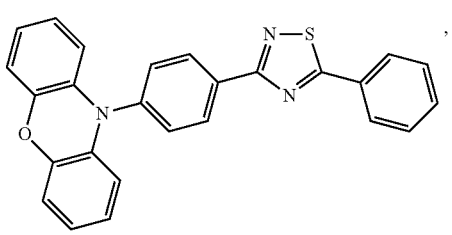

-continued
(C-32) 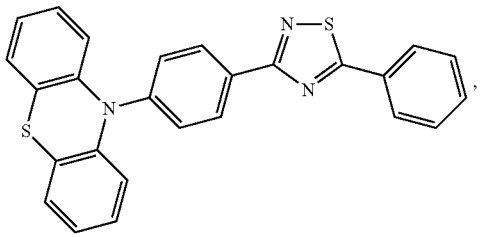
(C-33) 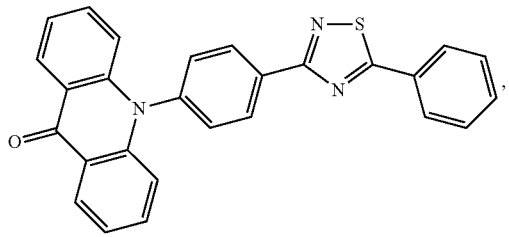
(C-34) 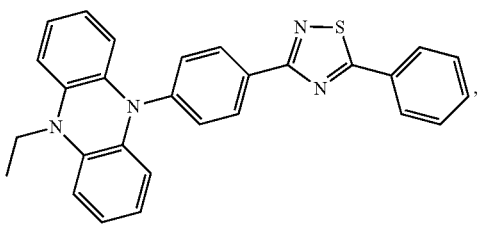
(C-35) 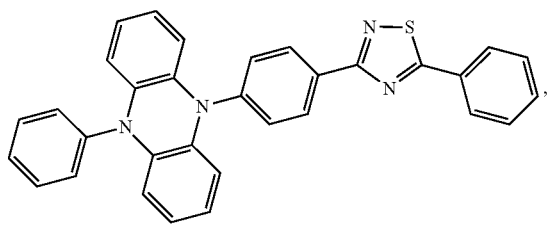
(C-36) 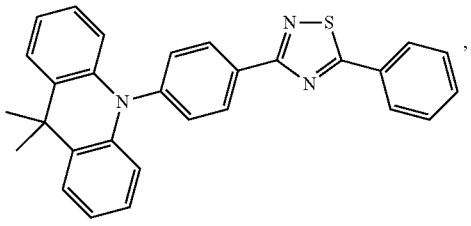
(C-37) 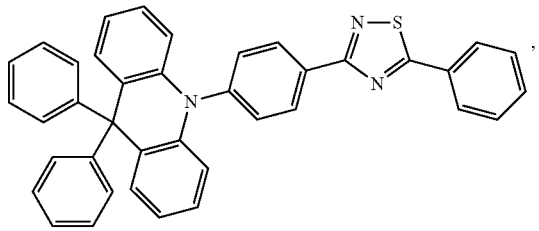
(C-38) 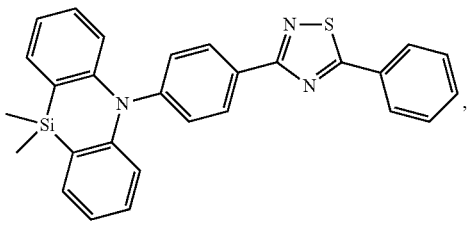
(C-39) 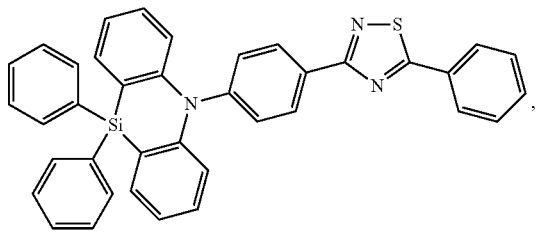
(C-40) 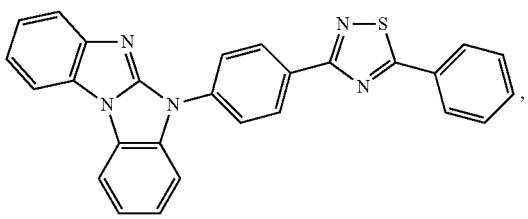
(C-75) 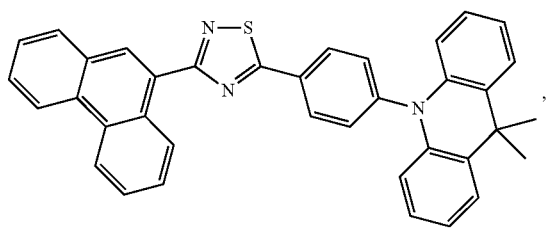
(C-76) 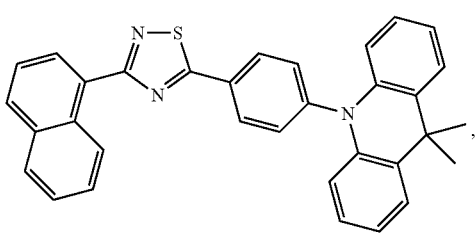
(C-77) 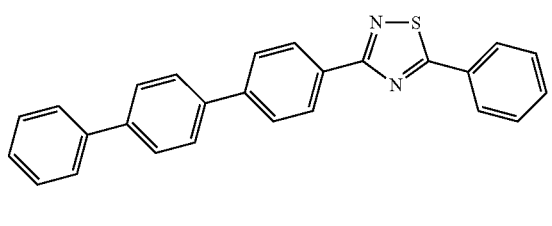

-continued
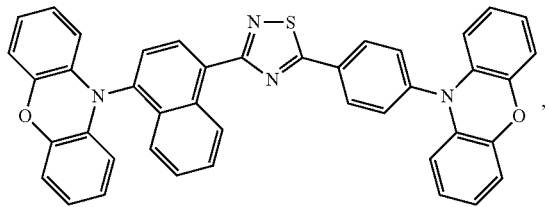
(C-78)
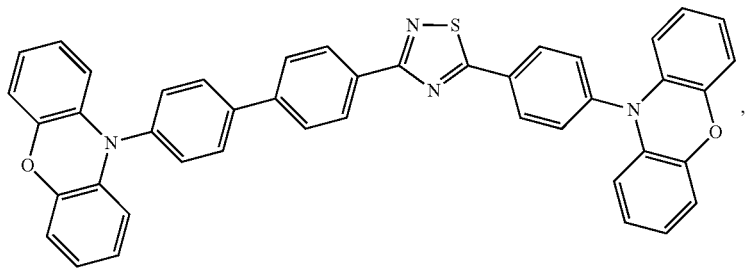
(C-79)
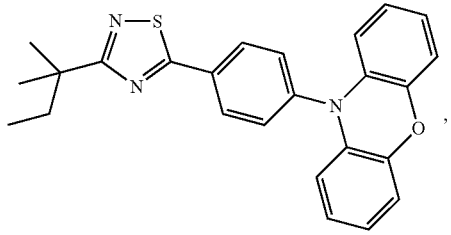
(C-80)
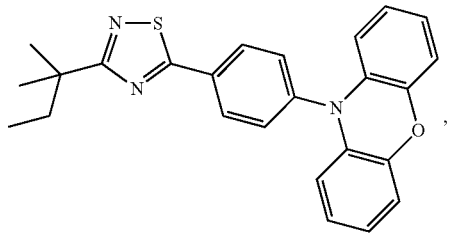
(C-81)
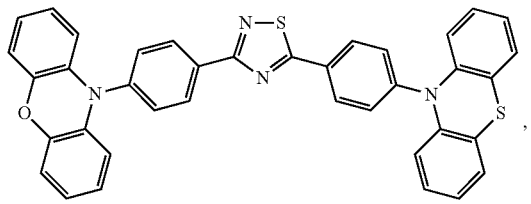
(C-82)
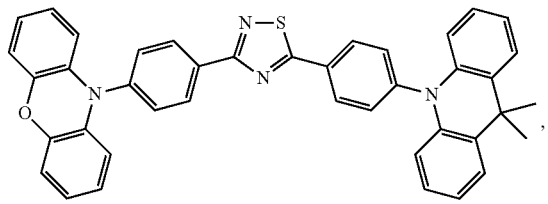
(C-83)
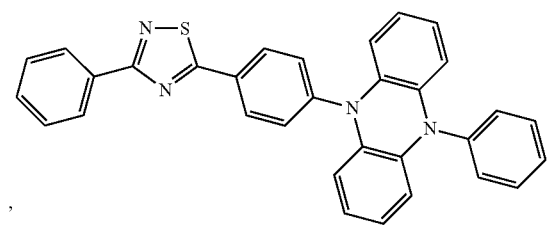
(C-84)
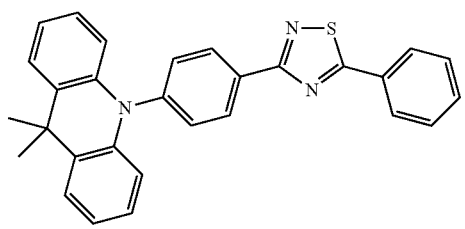
(C-85)
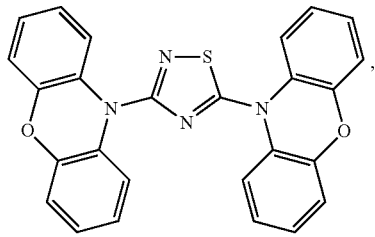
(C-86)
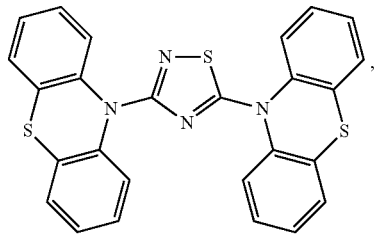
(C-87)

-continued
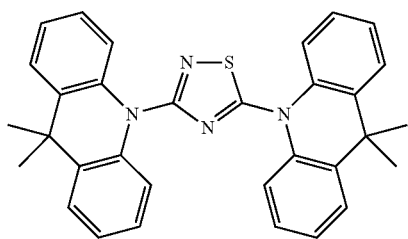
(C-88)
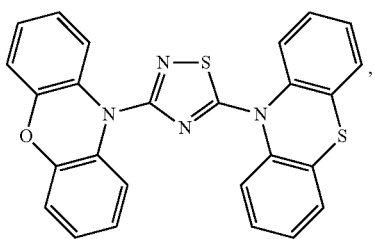
(C-89)
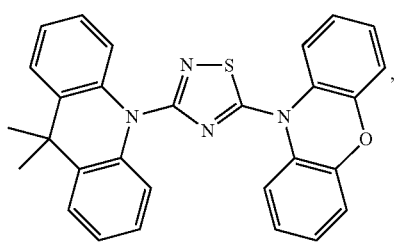
(C-90)
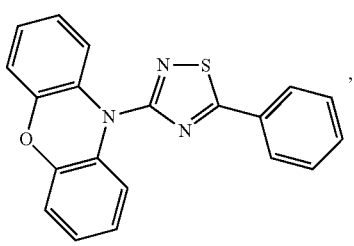
(C-92)
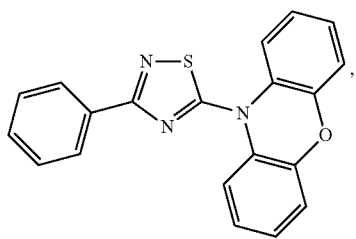
(C-93)
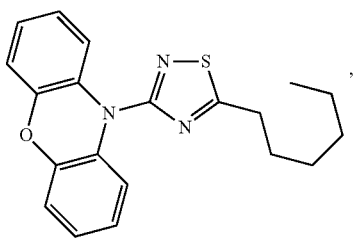
(C-95)
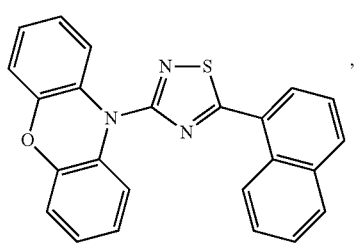
(C-96)
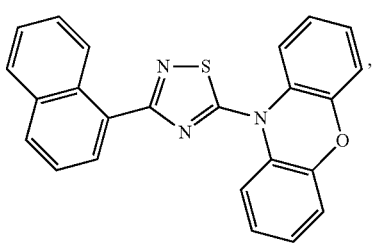
(C-97)
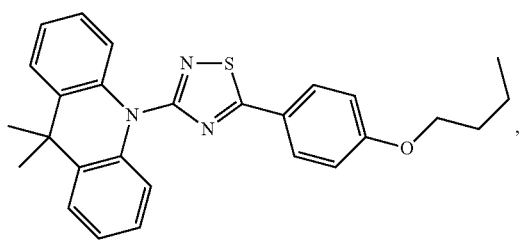
(C-98)
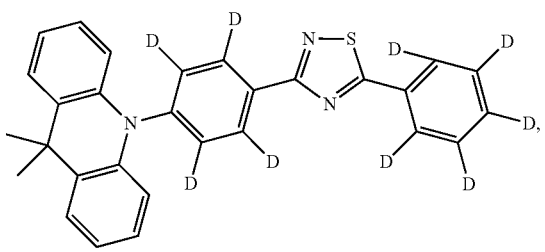
(C-99)
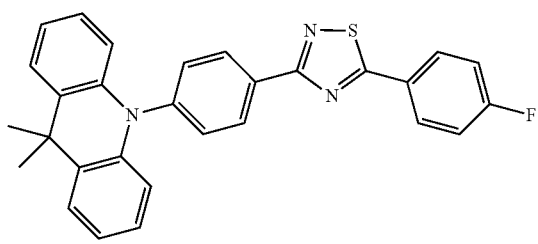
(C-100)

Among compounds of formula (Ic) those are preferred which are substituted especially by donor groups of formula

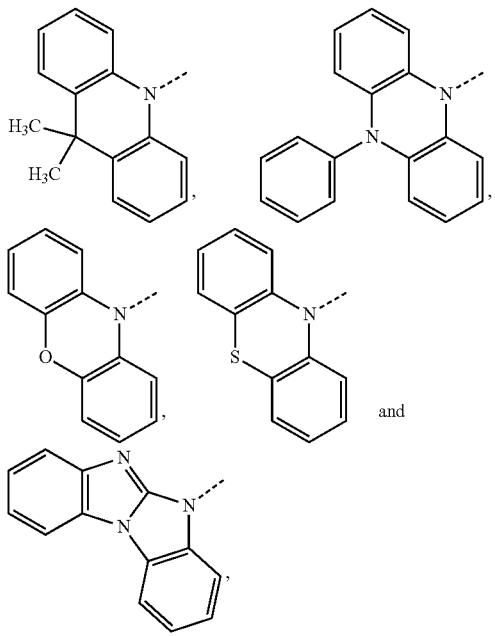

such as, for example, compounds (C-1), (C-2), (C-5), (C-6), (C-10), (C-21), (C-22), (C-25), (C-26), (C-30), (C-31), (C-32), (C-35), (C-36), (C-40), (C-75), (C-76), (C-81) (C-82), (C-83), (C-86), (C-87), (C-88), (C-89), (C-90), (C-92), (C-93), (C-99), and (C-100).

The most preferred examples are (C-1), (C-2), (C-5), (C-6), (C-21), (C-22), (C-25), (C-26), (C-31), (C-32), (C-35), (C-36), (C-76), (C-82), and (C-83).

$C_1$-$C_{25}$alkyl, preferably $C_1$-$C_{18}$alkyl is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups, preferably $C_1$-$C_{18}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

$C_6$-$C_{10}$aryl, which optionally can be substituted, is typically phenyl, naphthyl, especially 1-naphthyl, or 2-naphthyl, or biphenylyl, which may be unsubstituted or substituted by one, or more $C_1$-$C_8$alkyl, $C_1$-$C_8$alkoxy and/or $C_6$-$C_{10}$aryloxy groups, especially $C_1$-$C_8$alkyl, $C_1$-$C_8$alkoxy groups.

$C_6$-$C_{10}$aryloxy, which optionally can be substituted by one, or more $C_1$-$C_8$alkyl and/or $C_1$-$C_8$alkoxy groups, is typically phenoxy, 1-naphthoxy, or 2-naphthoxy.

The present invention further relates to a specific compound of formula

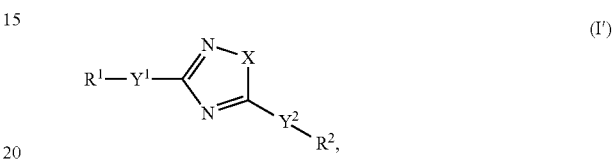

(I')

wherein

X is O, S, N—$Y^{4'}$—$R^4$ or N—$Y^{4''}$—$R^4$, $Y^1$ and $Y^2$ are independently of each other a direct bond, $C_1$-$C_{25}$-alkylene, or $C_6$-$C_{10}$-arylene, which is unsubstituted or substituted by one or more groups $R^3$;

$Y^{4'}$ is a direct bond, $C_1$-$C_{25}$-alkylene;

$Y^{4''}$ is $C_6$-$C_{10}$-arylene, which is unsubstituted or substituted by one or more groups $R^3$;

$R^1$ and $R^2$ are independently of each other hydrogen, deuterium, F, Cl, a $C_1$-$C_{25}$alkyl group, a $C_1$-$C_{25}$alkoxy group, a $C_6$-$C_{14}$aryloxy group, which is unsubstituted or substituted by one or more groups $R^3$, a $C_6$-$C_{14}$aryl group, which is unsubstituted or substituted by one or more groups $R^3$, or a group of formula (Xa) or (Xd);

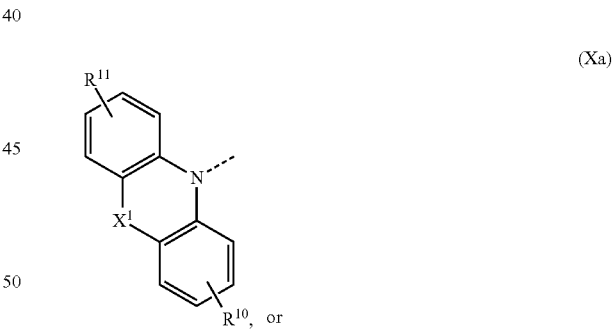

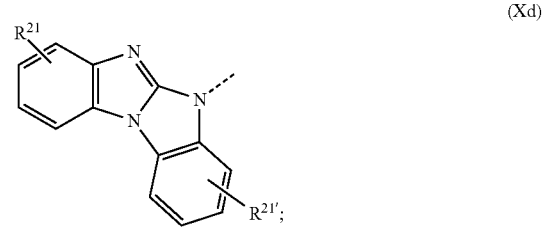

$R^3$ is deuterium, F, Cl, a $C_1$-$C_{25}$alkyl group, a $C_1$-$C_{25}$alkoxy group, a $C_6$-$C_{14}$aryloxy group, or a $C_6$-$C_{14}$aryl group;

$R^4$ is a $C_1$-$C_{25}$alkyl group, a $C_6$-$C_{10}$aryl group, which is unsubstituted or substituted by one or more groups $R^3$, or a group of formula (Xa) or (Xd);

$X^1$ is O, S, $N(R^{15})$, C(=O), $C(R^{16})(R^{17})$, $B(R^{18})$, or $Si(R^{19})(R^{20})$, or when X is N—$Y^{4''}$—$R^4$,
$X^1$ is $N(R^{15'})$, C(=O), $C(R^{16})(R^{17})$, $B(R^{18})$, or $Si(R^{19})(R^{20})$,
$R^{10}$, $R^{11}$, $R^{21}$ and $R^{21'}$ are independently of each other hydrogen, deuterium, F, Cl, a $C_1$-$C_{25}$alkyl group, a $C_1$-$C_{25}$alkoxy group, a $C_6$-$C_{14}$aryloxy group, which is unsubstituted or substituted by one or more groups $R^3$, or a $C_6$-$C_{14}$aryl group, which is unsubstituted or substituted by one or more groups $R^3$;
$R^{15}$, $R^{16}$, $R^{17}$, $R^{18}$, $R^{19}$ and $R^{20}$ are independently of each other a $C_1$-$C_{25}$alkyl group, or a $C_6$-$C_{14}$aryl group, which is unsubstituted or substituted by one or more groups $R^3$;
$R^{15'}$ is a $C_6$-$C_{14}$aryl group, which is unsubstituted or substituted by one or more groups $R^3$;
wherein at least one group of formula (Xa) or (Xd) is present in the compound of formula (I).

Preferred and particularly preferred residues and groups X, $X^1$, $Y^1$, $Y^2$, $R^1$, $R^2$, $R^3$, $R^4$, $R^{10}$, $R^{11}$, $R^{21}$, $R^{21'}$, $R^{15}$, $R^{16}$, $R^{17}$, $R^{18}$, $R^{19}$ and $R^{20}$ for the specific compounds of formula (I') are the same residues as mentioned concerning the compounds of formula (I) mentioned above.

$Y^{4'}$ is a is a direct bond, $C_1$-$C_{25}$-alkylene, preferably a direct bond; and $Y^{4''}$ is $C_6$-$C_{10}$-arylene, which is unsubstituted or substituted by one or more groups $R^3$ ($R^3$ is defined above); preferably a $C_6$-$C_{10}$arylene group which is unsubstituted or substituted by one or more $C_1$-$C_{25}$alkyl groups. Examples of $C_6$-$C_{10}$arylene groups are phenylene and naphthylene. Preferred $C_6$-$C_{10}$arylene groups are 1,3-phenylene and 3,6-naphthylene, which may be unsubstituted or substituted by one or more $C_1$-$C_8$alkyl groups. More preferably, $Y^{4''}$ is a group of formula

$X^1$ in the specific compounds of formula (I'), wherein X is N—$Y^{4''}$—$R^4$,
is $N(R^{15'})$, C(=O), $C(R^{16})(R^{17})$, $B(R^{18})$, or $Si(R^{19})(R^{20})$, preferably C(=O), $N(R^{15'})$, or $C(R^{16})(R^{17})$;
more preferably, $C(CH_3)(CH_3)$, C(=O), or

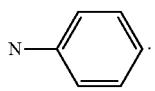

$R^{16'}$ in the specific compounds of formula (I') is a $C_6$-$C_{14}$aryl group, which is unsubstituted or substituted by one or more groups $R^3$, preferably a $C_6$-$C_{10}$aryl group, which is unsubstituted or substituted by one or more groups $R^3$, more preferably a group of formula

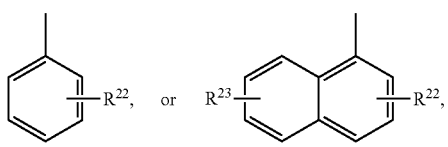

wherein $R^{22}$ and $R^{23}$ are independently of each other hydrogen, a $C_1$-$C_{25}$alkyl group, a $C_1$-$C_{25}$alkoxy group, a $C_6$-$C_{10}$aryloxy group, or a $C_6$-$C_{10}$aryl group; most preferably phenyl.

The group (Xa) in the specific compounds of formula (I'), wherein X is N—$Y^{4''}$—$R^4$, is therefore most preferably:

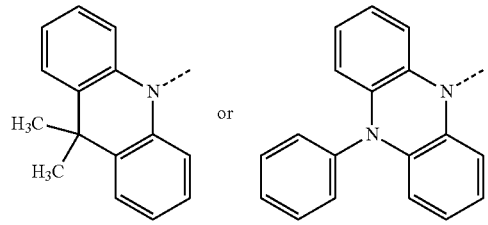

Specific examples of compounds of formula are:

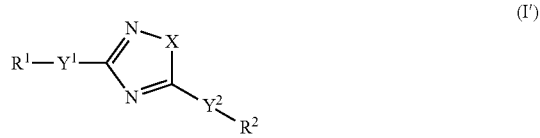

Specific examples of the compounds of formula (I'), wherein X is N—$Y^{4'}$—$R^4$ or N—$Y^{4'}$—$R^{4''}$ are the following compounds of formula (1'a):

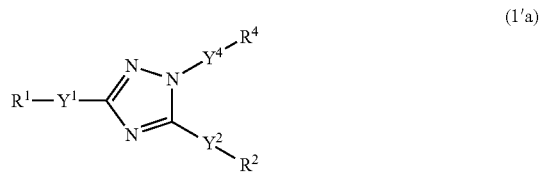

(A-1), (A-2), (A-3), (A-4), (A-5), (A-6), (A-7), (A-8), (A-9), (A-10), (A-13), (A-15), (A-16), (A-17), (A-18), (A-19) (A-20), (A-23), (A-25), (A-26), (A-27), (A-28), (A-29), (A-30), (A-33), (A-35), (A-36), (A-37), (A-38), (A-39), (A-40), (A-43), (A-45), (A-46), (A-47), (A-48), (A-49), (A-50), (A-51), (A-52), (A-53), (A-54), (A-55), (A-56), (A-57), (A-58), (A-59), (A-60), (A-61), (A-62), (A-63), (A-64), (A-65), (A-66), (A-67), (A-68), (A-69), (A-70), (A-71), (A-72), (A-73), (A-74), (A-75), (A-76), (A-77), (A-78), (A-79), (A-80), (A-81), (A-82), (A-83), (A-86), (A-87), (A-88), (A-89), (A-90), (A-94), (A-95), (A-96), (A-97), (A-98), (A-99), and (A-100).

Among compounds of formula (Ia) those are preferred which are substituted especially by groups (Xa) and/or (Xd) of formula

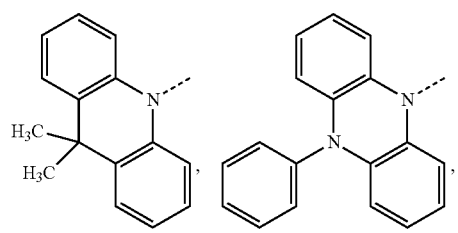

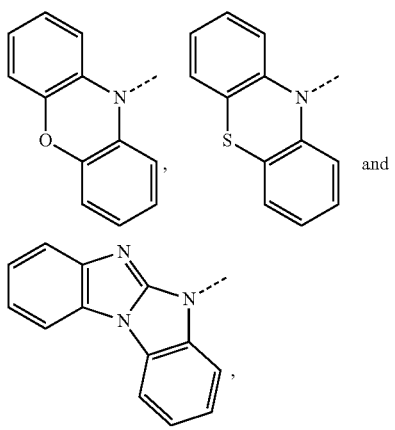

such as, for example, compounds (A-1), (A-2), (A-5), (A-6), (A-10), (A-15), (A-16), (A-20), (A-25), (A-26), (A-30), (A-35), (A-36), (A-40), (A-45), (A-46), (A-50), (A-51), (A-52), (A-55), (A-56), (A-60), (A-61), (A-62), (A-65), (A-66), (A-70), (A-71), (A-72), (A-73), (A-75), (A-76), (A-78), (A-81) (A-82), (A-83), (A-86), (A-87), (A-88), (A-89), (A-90), (A-94), (A-99), and (A-100).

The most preferred examples are (A-1), (A-2), (A-5), (A-6), (A-15), (A-16), (A-25), (A-26), (A-35), (A-36), (A-45), (A-46), (A-51), (A-52), (A-55), (A-56), (A-61), (A-62), (A-65), (A-66), (A-72), (A-73), (A-76), (A-82), and (A-83).

Specific examples of the compounds of formula (I'), wherein X is O are the following compounds of formula (I'b):

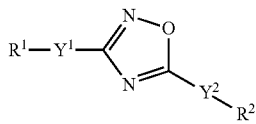
(1'b)

(B-1), (B-2), (B-3), (B-4), (B-5), (B-6), (B-7), (B-8), (B-9), (B-10), (B-21), (B-22), (B-23), (B-24), (B-25), (B-26), (B-27), (B-28), (B-29), (B-30), (B-31), (B-32), (B-33), (B-34), (B-35), (B-36), (B-37), (B-38), (B-39), (B-40), (B-75), (B-76), (B-77), (B-78), (B-79), (B-80), (B-81), (B-82), (B-83), (B-84), (B-85), (B-86), (B-87), (B-88), (B-89), (B-90), (B-92), (B-93), (B-95), (B-96), (B-97), (B-98), (B-99) and (B-100).

Among compounds of formula (1'b) those are preferred which are substituted especially by donor groups of formula

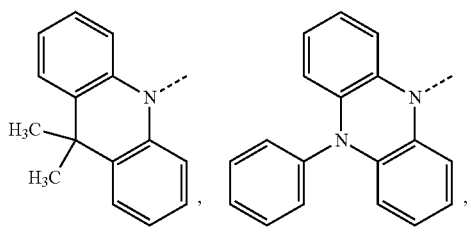

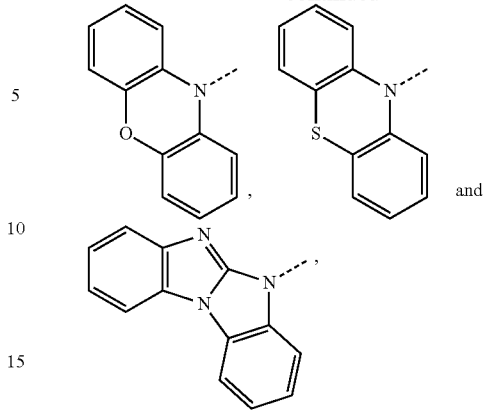

such as, for example, compounds (B-1), (B-2), (B-5), (B-6), (B-10), (B-21), (B-22), (B-25), (B-26), (B-30), (B-31), (B-32), (B-35), (B-36), (B-40), (B-75), (B-76), (B-78), (B-81), (B-82), (B-83), (B-86), (B-87), (B-88), (B-89), (B-90), (B-92), (B-93), (B-99), and (B-100).

The most preferred examples are (B-1), (B-2), (B-5), (B-6), (B-21), (B-22), (B-25), (B-26), (B-31), (B-32), (B-35), (B-36), (B-76), (B-82) and (B-83).

Specific examples of the compounds of formula (I'), wherein X is O are the following compounds of formula (1'c):

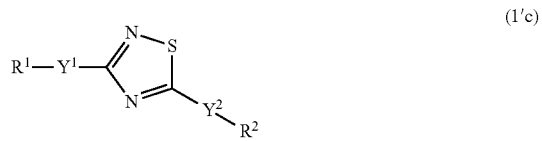
(1'c)

(C-1), (C-2), (C-3), (C-4), (C-5), (C-6), (C-7), (C-8), (C-9), (C-10), (C-21), (C-22), (C-23), (C-24), (C-25), (C-26), (C-27), (C-28), (C-29), (C-30), (C-31), (C-32), (C-33), (C-34), (C-35), (C-36), (C-37), (C-38), (C-39), (C-40), (C-75), (C-76), (C-77), (C-78), (C-79), (C-80), (C-81), (C-82), (C-83), (C-84), (C-85), (C-86), (C-87), (C-88), (C-89), (C-90), (C-92), (C-93), (C-95), (C-96), (C-97), (C-98), (C-99) and (C-100).

Among compounds of formula (1'c) those are preferred which are substituted especially by donor groups of formula

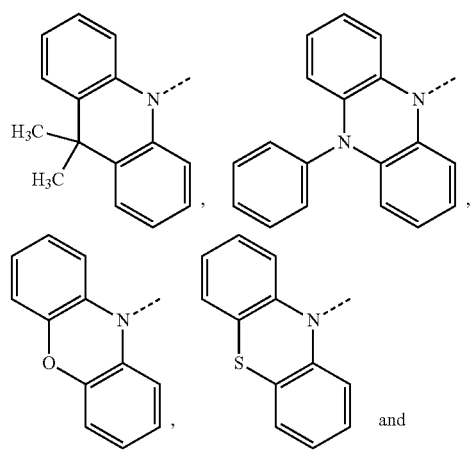

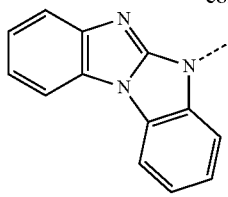

such as, for example, compounds (C-1), (C-2), (C-5), (C-6), (C-10), (C-21), (C-22), (C-25), (C-26), (C-30), (C-31), (C-32), (C-35), (C-36), (C-40), (C-75), (C-76), (C-81) (C-82), (C-83), (C-86), (C-87), (C-88), (C-89), (C-90), (C-92), (C-93), (C-99), and (C-100).

The most preferred examples are (C-1), (C-2), (C-5), (C-6), (C-21), (C-22), (C-25), (C-26), (C-31), (C-32), (C-35), (C-36), (C-76), (C-82), and (C-83).

In addition, the present invention is directed to an organic light emitting element, comprising the specific compound of the formula (I').

Further, the present invention is directed to an organic light-emitting element comprising the light-emitting layer comprising the specific compound of formula (I').

For the specific compounds of formula (I') the preferences specified above apply.

The specific compounds of formula (I') or the compounds of formula (I) can be used as host in combination with a fluorescent guest material in the emitting layer of an organic EL element. Known fluorescent materials are usable as the fluorescent guest material. Examples of the fluorescent guest material include a bisarylamino naphthalene derivative, an aryl-substituted naphthalene derivative, a bisarylamino anthracene derivative, an aryl-substituted anthracene derivative, a bisarylamino pyrene derivative, an aryl-substituted pyrene derivative, a bisarylamino chrysene derivative, an aryl-substituted chrysene derivative, a bisarylamino fluoranthene derivative, an aryl-substituted fluoranthene derivative, an indenoperylene derivative, a pyrromethene boron complex compound, a compound having a pyrromethene skeleton or a metal complex thereof, a diketopyrrolopyrrole derivative, and a perylene derivative. Examples are 2,5,8,11-tetra-tert-butylperylene (TBPe), 9,10-bis[N,N-di-(p-tolyl)-amino]anthracene (TTPA), 2,8-di-tert-butyl-5,11-bis (4-tert-butylphenyl)-6,12-diphenyltetracene (TBRb) and dibenzo{[f,f']-4,4',7,7'-tetraphenyl}diindeno[1,2,3-cd:1',2',3'-lm]perylene (DBP). In case of using the specific compound of formula (I') or the compounds of formula (I) as host material, the content of the compound of formula (I') or the compound of formula (I) in the light-emitting layer preferably falls within the range of 51 to 99 wt %, more preferably 80 to 99 wt %, based on the total weight of the light-emitting layer.

The present invention therefore further relates to the organic light-emitting element as mentioned above, comprising a light-emitting layer comprising a specific compound of formula (I') as host and a guest material.

For the specific compounds of formula (I') the preferences specified above apply.

Alternatively, the specific compounds of formula (I') as well as the compounds of formula (I) can be used as guest in combination with a host material in the light-emitting layer of an organic EL element. Said guest compounds are preferably present in the light-emitting layer in an amount of 1 to 50 wt %, more preferably 1% by weight to 25% by weight, most preferably 6% to 15% by weight, based on the total weight of the light emitting layer.

The compound of formula (I), respectively the specific compound of formula (I'), i.e. the organic light-emitting material, has preferably a difference between excited singlet energy and excited triplet energy (($\Delta E_{ST}$) of 0.5 eV or less, more preferably $\Delta E_{ST}$ of 0.35 eV or less, i.e. of 0.01 to 0.5 eV, especially 0.01 to 0.35 eV. The compound of formula (I) or the specific compounds of formula (I') may be used alone in the light-emitting layer as organic light-emitting material. However, as necessary, for the purpose of, for example, confining, in the organic light-emitting material, singlet excitons and triplet excitons generated in the organic light-emitting material, the organic light-emitting material of the present invention and an organic compound which has a higher value of at least any one of excited singlet energy and excited triplet energy than those of the organic light-emitting material and serves as a host material are preferably used in the light-emitting layer. At least any one of the excited singlet energy ($S_{1h}$) and excited triplet energy ($T_{1h}$) of the host compound is preferably higher by 0.1 eV or more, particularly preferably higher by 0.2 eV or more than the excited singlet energy ($S_{1g}$) and excited triplet energy ($T_{1g}$) of the organic light-emitting material of the present invention. That is, it is preferred that one or both of ($S_{1h}$)–($S_{1g}$)>0.1 eV and ($T_{1h}$)–($T_{1g}$)>0.1 eV be satisfied and it is more preferred that one or both of ($S_{1h}$)–($S_{1g}$)>0.2 eV and ($T_{1h}$)–($T_{1g}$)>0.2 eV be satisfied. In case of using the compound of formula (I) or the specific compound of formula (I') as guest material, the content of the compound of formula (I) or the specific compound of formula (I') in the light-emitting layer preferably falls within the range of 1 to 50 wt %, more preferably 1 to 25 wt %, most preferably 6 to 15 wt %, based on the total weight of the light emitting layer.

The present invention therefore further relates to the organic light-emitting element mentioned above, comprising a light-emitting layer comprising a specific compound of formula (I') as guest and a host material.

For the specific compounds of formula (I') the preferences specified above apply.

The organic EL element (organic light-emitting element) of the present invention usually has, as essential layers, an anode, a hole-transporting layer, a light-emitting layer, and a cathode.

Further, the organic EL element of the present invention may have—in addition to the usually essential layers—, as layers other than the usually essential layers, an electron-transporting layer, an electron-injecting layer, an electron-blocking layer, a hole-blocking layer, and an exciton element layer. In addition, the hole-transporting layer may be a hole-injecting/transporting layer having a hole-injecting function and the electron-transporting layer may be an electron-injecting/transporting layer having an electron-injecting function.

An example for an organic EL element comprises therefore at least the following layers: an anode, a hole-transporting layer, a light-emitting layer, an electron-transporting layer, and a cathode.

The organic EL element of the present invention may comprise in this order: a substrate, an anode, a hole-injecting layer, a hole-transporting layer, a light-emitting layer, an electron-transporting layer and a cathode. Alternatively, the cathode, the electron-transporting layer, the light-emitting layer, the hole-transporting layer, and the anode may be laminated on the substrate in the stated order.

Substrate

The organic EL element of the present invention is preferably supported by a substrate. The substrate is not particularly limited and may be any substrate which is conventionally used in an organic EL element. For example, a substrate formed of glass, transparent plastic, quartz, or the like may be used.

Anode

Preferably used as the anode in the organic EL element is one using, as an electrode substance, any of a metal, an alloy, an electrically conductive compound, and a mixture thereof with a high work function (4 eV or more). Specific examples of such electrode substance include metals such as Au and conductive transparent materials such as CuI, indium tin oxide (ITO), $SnO_2$, and ZnO. Further, a material capable of producing an amorphous transparent conductive film such as IDIXO ($In_2O_3$—ZnO) may be used. In the production of the anode, it is possible to form any of those electrode substances into a thin film by a method such as vapor deposition or sputtering, and then form a pattern having a desired shape by a photolithographic method. Alternatively, in the case of using a coatable substance such as an organic conductive compound, it is also possible to employ a wet film-forming method of a printing mode, a coating mode, or the like.

Cathode

Meanwhile, preferably used as the cathode is one using, as an electrode substance, any of a metal (referred to as electron-injecting metal), an alloy, an electrically conductive compound, and a mixture thereof with a low work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, from the viewpoints of electron-injecting property and durability against oxidation and the like, a mixture of an electron-injecting metal and a second metal, which has a work function value higher than that of the electron-injecting metal and is a stable metal, such as a magnesium/silver mixture, a magnesium/aluminum mixture, a magnesium/indium mixture, an aluminum/aluminum oxide ($Al_2O_3$) mixture, a lithium/aluminum mixture, or aluminum is suitable. It should be noted that a case where any one of the anode and the cathode of the organic EL element is transparent or translucent in order to transmit emitted light is advantageous because light emission luminance is improved.

Light-Emitting Layer

The light-emitting layer is a layer which emits light after excitons have been generated through the recombination of holes and electrons injected respectively from an anode and a cathode. The light-emitting layer preferably includes an organic light-emitting material and a host material. As the organic light-emitting material, there may be used one kind or two or more kinds selected from the compounds of formula (I), respectively selected from the specific compounds of formula (I'). In order that the organic EL element of the present invention exhibits high luminous efficiency, it is important to confine, in the organic light-emitting material, singlet excitons and triplet excitons generated in the organic light-emitting material. Accordingly, it is preferred to use a host material in addition to the organic light-emitting material in the light-emitting layer. As the host material, there may be used an organic compound having a higher value of at least any one of excited singlet energy and excited triplet energy than those of the organic light-emitting material of the present invention. This allows singlet excitons and triplet excitons generated in the organic light-emitting material of the present invention to be confined in the molecule of the organic light-emitting material of the present invention and allows the luminous efficiency to be exhibited sufficiently. In the organic EL element of the present invention, light is emitted from the organic light-emitting material of the present invention included in the light-emitting layer.

In case of using the host material below, the content of the organic light-emitting material of the present invention in the light-emitting layer falls preferably within the range of 1 to 50 wt %, more preferably 1 to 25 wt %, most preferably 6 to 15 wt %, based on the total weight of the light emitting layer.

The host material in the light-emitting layer is preferably an organic compound which has a hole-transporting ability and/or an electron-transporting ability, prevents an emission wavelength from becoming longer, and has a high glass transition temperature.

The host material may be a polymer, for example poly (N-vinylcarbazole) or polysilane. The host material may, however, be a small molecule, for example 4,4-N,N-dicarbazolebiphenyl (CDP=CBP), 2,6-bis(N-carbazolyl)phenyl (mCP), 3,3-Di(9H-carbazol-9-yl)biphenyl (mCBP),

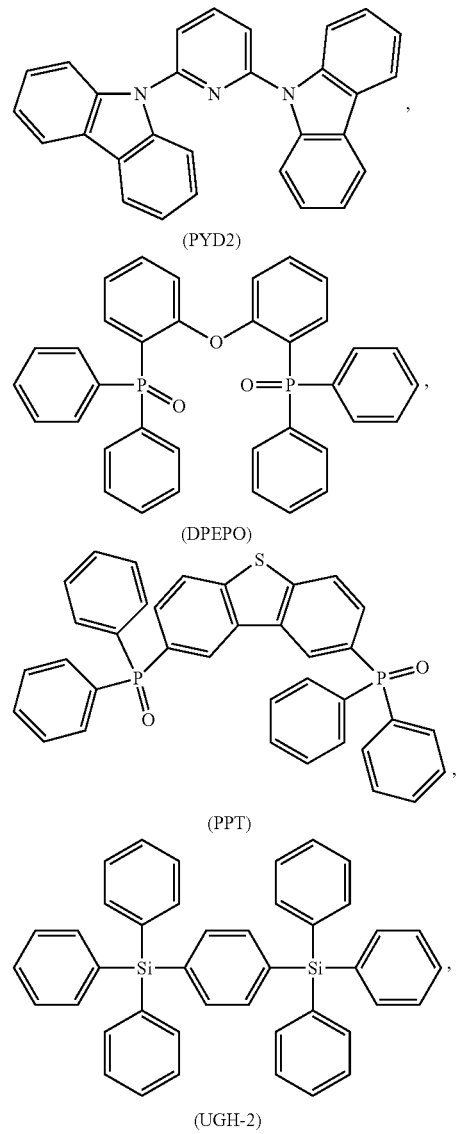

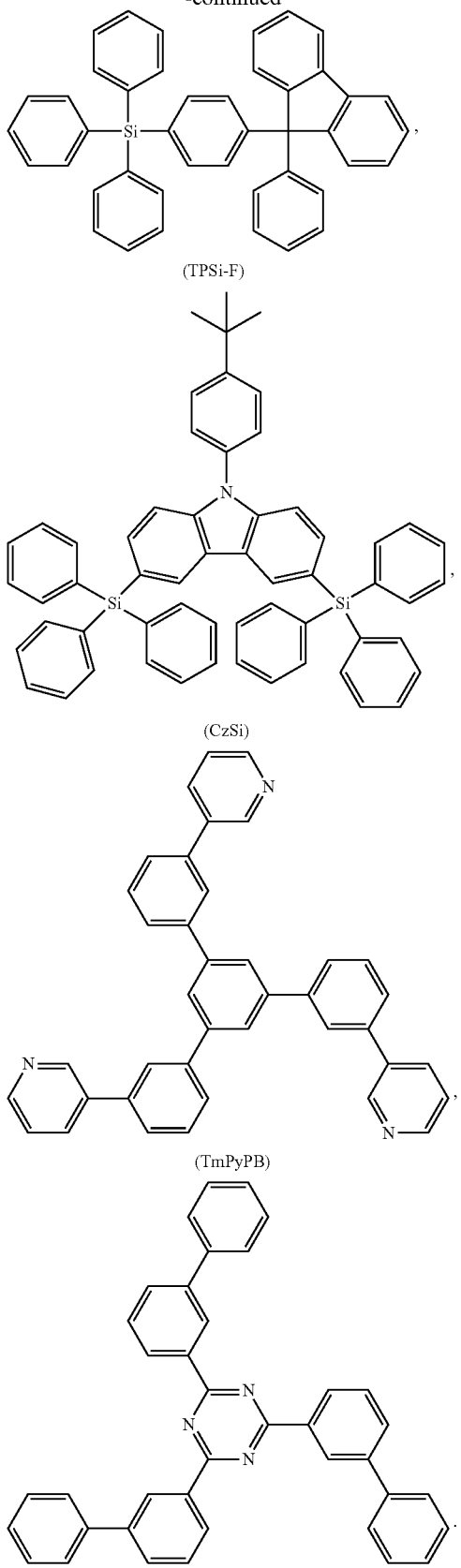

(TPSi-F), (CzSi), (TmPyPB), (2,4,6-tris(bipheyl-3-yl)-1,3,5,-triazine (T2T)) or tertiary aromatic amines, for example TCTA However, as mentioned above, the compounds of formula (I) as well as the specific compounds of formula (I') can alternatively be used as host in combination with a fluorescent guest material in the emitting layer of an organic EL element. Known fluorescent materials are usable as the fluorescent guest material. Suitable fluorescent materials are mentioned above.

Injecting Layer

The injecting layer refers to a layer to be provided between an electrode and an organic layer for the purposes of reducing a driving voltage and improving a light emission luminance. The injecting layer includes a hole-injecting layer and an electron-injecting layer, and may be provided between the anode and the light-emitting layer or the hole-transporting layer, and between the cathode and the light-emitting layer or the electron-transporting layer. The injecting layer may be provided as necessary.

Customarily used hole injection materials include CuPc, MTDATA, or dipyrazino[2,3-f:2',3'-h]quinoxaline-2,3,6,7,10,11-hexacarbonitrile (HAT-CN). Polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

Lithium-comprising organometallic compounds such as 8-hydroxyquinolatolithium (Liq), CsF, NaF, KF, $Cs_2CO_3$ or LiF may be applied between the electron transport layer and the cathode as an electron injection layer in order to reduce the operating voltage.

Blocking Layer

The blocking layer is capable of blocking charges (electrons or holes) and/or excitons present in the light-emitting layer from diffusing to the outside of the light-emitting layer. The electron-blocking layer may be arranged between the light-emitting layer and the hole-transporting layer, and blocks electrons from passing through the light-emitting layer toward the hole-transporting layer. Similarly, the hole-blocking layer may be arranged between the light-emitting layer and the electron-transporting layer, and blocks holes from passing through the light-emitting layer toward the electron-transporting layer. The blocking layer may also be used for blocking excitons from diffusing to the outside of the light-emitting layer. That is, the electron-blocking layer and the hole-blocking layer may each have a function of an exciton-blocking layer as well. The electron-blocking layer or exciton-blocking layer as used herein is meant to include a layer having a function of an electron-blocking layer and an exciton-blocking layer in one layer.

Hole-Blocking Layer

The hole-blocking layer has a function of the electron-transporting layer in a broad sense. The hole-blocking layer has a role in blocking holes from reaching the electron-transporting layer while transporting electrons. This can improve the probability of recombination of electrons and holes in the light-emitting layer. As a material for the hole-blocking layer, a material for the electron-transporting layer to be described below may be used as necessary.

Electron-Blocking Layer

The electron-blocking layer has a function of transporting holes in a broad sense. The electron-blocking layer has a role in blocking electrons from reaching the hole-transporting layer while transporting holes. This can improve the probability of recombination of electrons and holes in the light-emitting layer.

Exciton-Blocking Layer

The exciton-blocking layer refers to a layer for blocking excitons, which are generated by the recombination of holes and electrons in the light-emitting layer, from diffusing to a charge-transporting layer. The insertion of this layer allows excitons to be efficiently confined in the light-emitting layer, which can improve the luminous efficiency of an element. The exciton-blocking layer may be inserted on any of the anode side and the cathode side of the adjacent light-emitting layer, and may be simultaneously inserted on both of the sides. That is, when the exciton-blocking layer is provided on the anode side, the layer may be inserted between the hole-transporting layer and the light-emitting layer so as to be adjacent to the light-emitting layer. When the exciton-blocking layer is inserted on the cathode side, the layer may be inserted between the light-emitting layer and the cathode so as to be adjacent to the light-emitting layer. Further, the hole-injecting layer, the electron-blocking layer, and the like may be provided between the anode and the exciton-blocking layer adjacent to the anode side of the light-emitting layer, and the electron-injecting layer, the electron-transporting layer, the hole-blocking layer, and the like may be provided between the cathode and the exciton-blocking layer adjacent to the cathode side of the light-emitting layer. In the case of providing the blocking layer, it is preferred that at least any one of the excited singlet energy and excited triplet energy of a material to be used as the blocking layer be higher than the excited singlet energy and excited triplet energy of a light-emitting material.

Hole blocker materials typically used are 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris(N-phenyl-2-benzylimidazolyl)benzene) (TPBI), TPBI also being suitable as electron-transport material. Further suitable hole blockers and/or electron conductor materials are 2,2',2"-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2,2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris (2,4,6-trimethyl-3-(pyridin-3-yl)phenyl)borane, 2,9-bis (naphthalene-2-yl)-4,7-diphenyl-1,10-phenanthroline, 1-methyl-2-(4-(naphthalene-2-yl)phenyl)-1H-imidazo[4,5-f][1,10]phenanthroline,

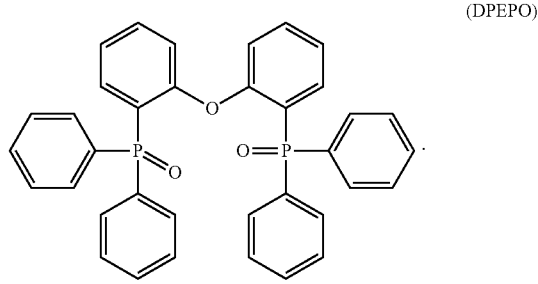 [SMILES: O=P(c1ccccc1)(c1ccccc1)c1ccccc1Oc1ccccc1P(=O)(c1ccccc1)c1ccccc1]

(DPEPO)

Hole-Transporting Layer

The hole-transporting layer is formed of a hole-transporting material having a function of transporting holes. The hole-transporting layer may be provided in a single layer or a plurality of layers.

The hole-transporting material has any of hole-injecting or -transporting property and electron-blocking property, and may be an organic material or an inorganic material. An applicable known hole-transporting material is exemplified by a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, or a conducting polymeric oligomer, particularly a thiophene oligomer. However, preferably used are a porphyrin compound, an aromatic tertiary amine compound, and a styrylamine compound, and more preferably used is an aromatic tertiary amine compound. Customarily used hole-transporting molecules are selected from the group consisting of

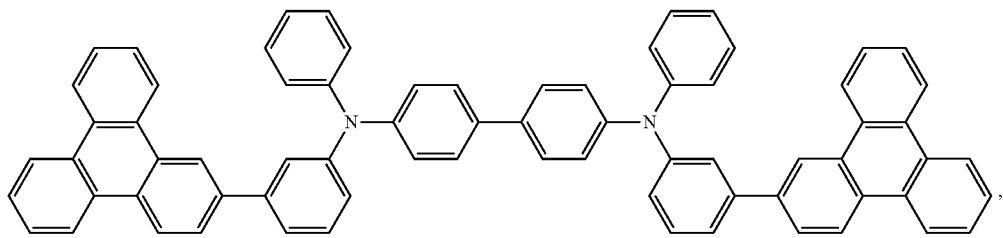

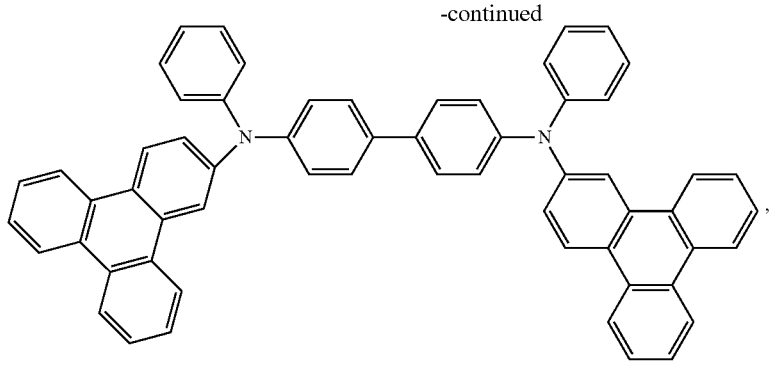
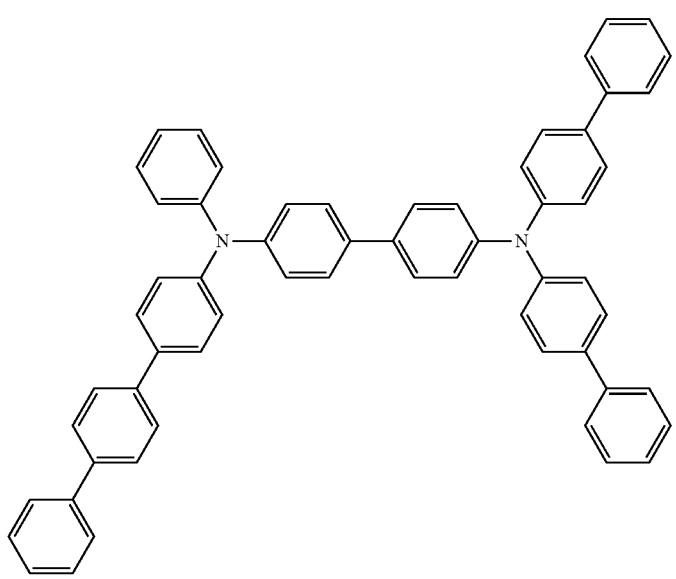
(4-phenyl-N-(4-phenylphenyl)-N-[4-[4-(N-[4-(4-phenyl-phenyl)phenyl]anilino)phenyl]phenyl]aniline),
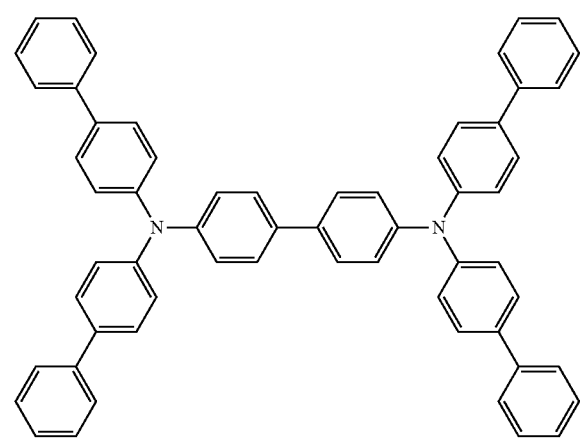 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
(4-phenyl-N-(4-phenylphenyl)-N-[4-[4-(4-phenyl-N-(4-phenylphenyl)anilino)phenyl]phenyl]aniline),
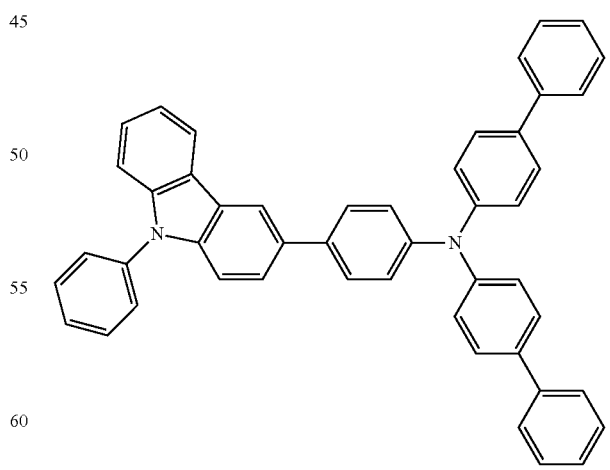
(4-phenyl-N-[4-(9-phenylcarbazol-3-yl)phenyl]-N-(4-phenylphenyl)aniline),

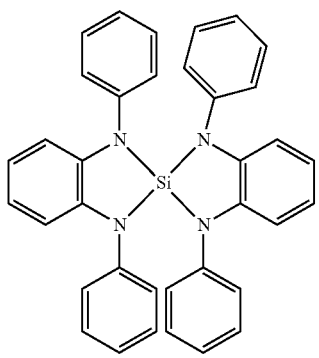 [SMILES: c1ccc(N2c3ccccc3N(c3ccccc3)[Si]23N(c2ccccc2)c2ccccc2N3c2ccccc2)cc1]

(1,1',3,3'-tetraphenylspiro[1,3,2-benzodiazasilole-2,2'-3a,7a-dihydro-1,3,2-benzodiazasilole]),

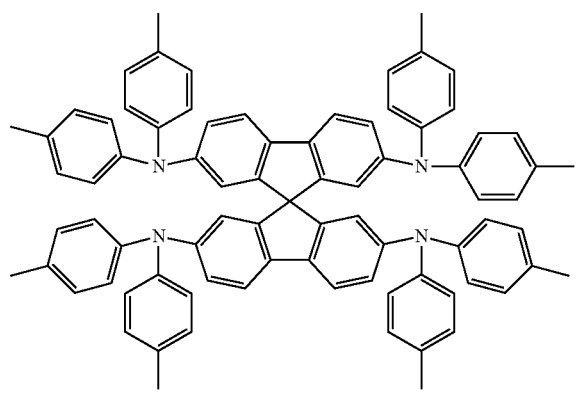

(N2,N2,N2',N2',N7,N7,N7',N7'-octakis(p-tolyl)-9,9'-spirobi[fluorene]-2,2',7,7'-tetramine), 4,4'-bis[N-(1-naphthyl)-N-phenylamino]biphenyl (α-NPD), N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)2-methylphenyl](4-methylphenyl)methane (MPMP), 1-phenyl-3-[p-(diethylamino)styryl]5-[p-(diethylamino)phenyl]pyrazoline (PPR or DEASP), 1,2-trans-bis(9H-carbazol 9-yl)-cyclobutane (DCZB), N,N,N',N'-tetrakis(4-methylphenyl)-(1,1'-biphenyl)-4,4'-diamine (TTB), fluorine compounds such as 2,2',7,7'-tetra(N,N-di-tolyl)amino9,9-spirobifluorene (spiro-TTB), N,N'-bis(naphthalen-1-yl)-N,N'-bis(phenyl)9,9-spirobifluorene (spiro-NPB) and 9,9-bis(4-(N,N-bis-biphenyl-4-yl-amino)phenyl-9Hfluorene, benzidine compounds such as N,N'-bis(naphthalen-1-yl)-N,N'-bis(phenyl)benzidine and porphyrin compounds such as copper phthalocyanines,

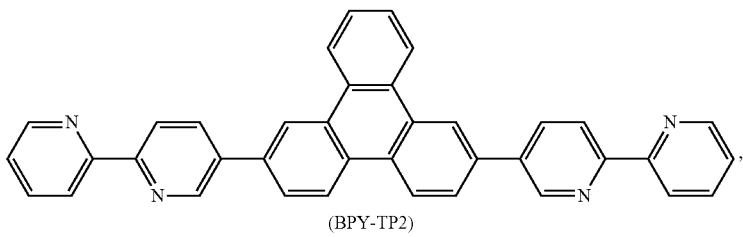
(BPY-TP2)

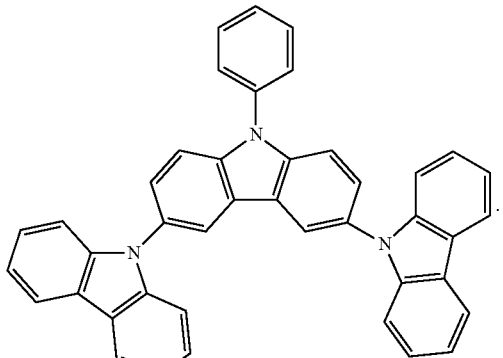
(Tris-PCz)

In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

Electron-Transporting Layer

The electron-transporting layer is formed of a material having a function of transporting electrons. The electron-transporting layer may be provided in a single layer or a plurality of layers.

An electron-transporting material (may also serve as a hole-blocking material) has only to have a function of transporting electrons, which are injected from the cathode, to the light-emitting layer. An applicable electron-transporting layer is exemplified by a nitro-substituted fluorene derivative, a diphenylquinone derivative, a thiopyran dioxide derivative, carbodiimide, a fluorenylidenemethane derivative, an anthraquinodimethane derivative, an anthrone derivative, or an oxadiazole derivative. In addition, in oxadiazole derivative, a thiadiazole derivative in which an oxygen atom of an oxadiazole ring is substituted by a sulfur atom, or a quinoxaline derivative having a quinoxaline ring known as an electron-withdrawing group may also be used as the electron-transporting material. In addition, a polymer material obtained by introducing any of those materials into a polymer chain, or a polymer material including any of those materials in a polymer main chain may also be used. Suitable electron-transporting materials comprise 1,3,5-tris (N-phenyl-2-benzylimidazolyl)benzene (TPBi), (BPY-TP2)

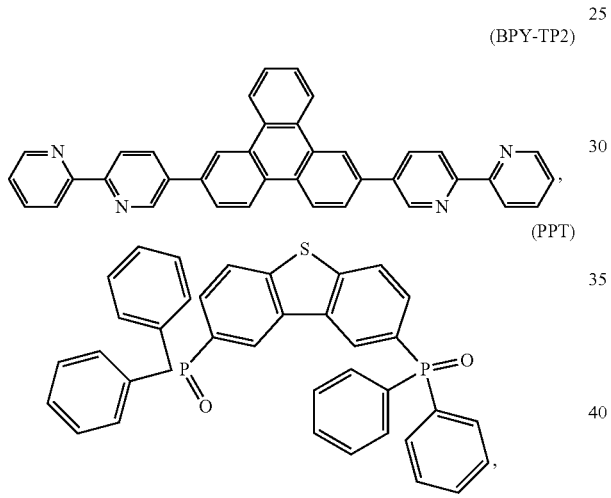

(PPT)

metals chelated with oxinoid compounds, such as tris(8-hydroxyquinolato)aluminum (Alq$_3$), compounds based on phenanthroline such as 2,9-dimethyl-4,7-diphenyl-1,10-phenanthroline (DDPA=BCP), 4,7-diphenyl-1,10-phenanthroline (Bphen), 2,4,7,9-tetraphenyl-1,10-phenanthroline, 4,7-diphenyl-1,10-phenanthroline (DPA) or phenanthroline derivatives disclosed in EP1786050, in EP1970371, or in EP1097981, and azole compounds such as 2-(4-biphenylyl)-5-(4-t-butylphenyl)-1,3,4-oxadiazole (PBD) and 3-(4-biphenylyl)-4phenyl-5-(4-t-butylphenyl)-1,2,4-triazole (TAZ).

Examples of possible element structures are shown below:
ITO (100 nm)/α-NPD (35 nm)/CBP: 6% by weight compound of formula (I), respectively of the specific compound of formula (I') (15 nm)/TPBi (65 nm)/LiF (0.8 nm)/Al (80 nm)
ITO (100 nm)/α-NPD (40 nm)/mCP/PPT: 6% by weight compound of formula (I), respectively of the specific compound of formula (I') (20 nm)/PPT (40 nm)/LiF (0.8 nm)/Al (80 nm)
ITO (30-100 nm)/α-NPD (60 nm)/mCP: 6% by weight compound of formula (I), respectively of the specific compound of formula (I') (20 nm)/Bphen (40 nm)/MgAg (100 nm)/Ag (20 nm)
ITO (30-100 nm)/α-NPD (60 nm)/PYD2: 6% by weight compound of formula (I), respectively of the specific compound of formula (I') (20 nm)/Bphen (40 nm)/MgAg (100 nm)/Al (20 nm)
ITO/α-NPD (35 nm)/6% by weight compound of formula (I), respectively of the specific compound of formula (I'): CBP (15 nm)/TPBi (65 nm)/LiF (0.8 nm)/Al (80 nm)
ITO (100 nm)/HAT-CN (10 nm)/Tris-PCz (30 nm)/CBP: 3, 6, 10, or 15% by weight compound of formula (I), respectively of the specific compound of formula (I') (30 nm)/BPY-TP2 (40 nm)/LiF (0.8 nm)/Al (100 nm)
ITO (100 nm)/α-NPD (35 nm)/CBP (10 nm)/DPEPO: 6 to 12% by weight compound of formula (I), respectively of the specific compound of formula (I') (15 nm)/DPEPO (10 nm)/TPBi (65 nm)/LiF (0.5 nm)/Al (80 nm)]
ITO: indium/tin oxide; α-NPD: 4,4'-bis[N-(1-naphthyl)-N-phenylamino]biphenyl;
CBP: 4,4'-N,N'-dicarbazolebiphenyl; TPBi: 1,3,5-tris(N-phenyl-2-benzylimidazolyl)benzene; mCP: 2,6-bis(N-carbazolyl)pyridine;

PPT

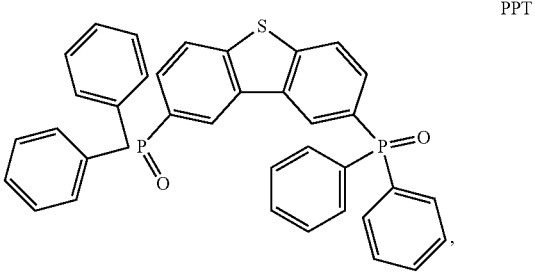

Bphen:4,7-diphenyl-1,10-phenanthroline;

PYD2

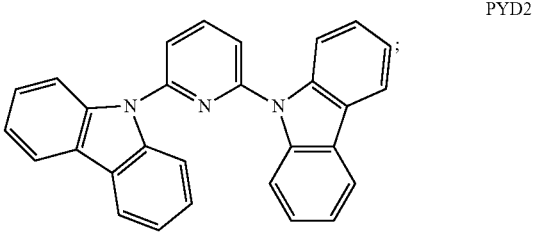 [SMILES: c1cc(-n2c3ccccc3c3ccccc32)nc(-n2c3ccccc3c3ccccc32)c1]

HAT-CN: dipyrazino[2,3-f:2',3'-h]quinoxaline-2,3,6,7,10,11-hexacarbonitrile;

Tris-PCz

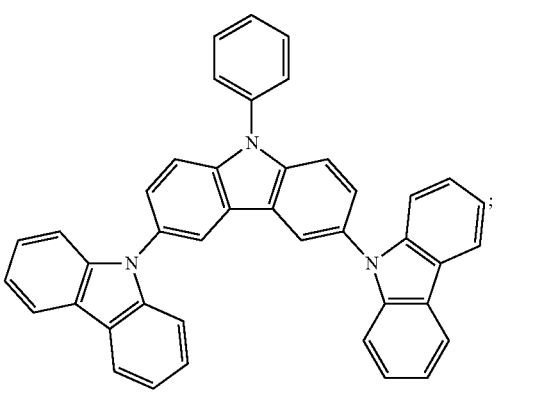

BPY-TP2

DPEPO

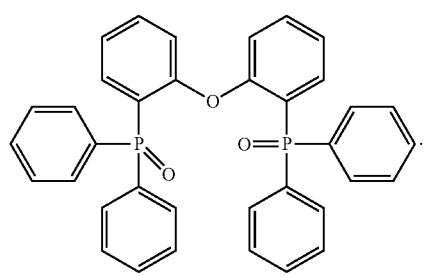

The organic EL element emits light when an electric field is applied between an anode and a cathode of the resultant element.

The organic EL element of the present invention may be applied to any of a single element, an element formed of a structure with arrangement in an array fashion, and a structure in which an anode and a cathode are arranged in an X-Y matrix fashion.

The organic light-emitting element according to the present invention is characterized in that it emits light by delayed fluorescence.

According to the present invention, there is provided an element having significantly improved luminous efficiency as compared to a conventional element using light emission from a singlet state by incorporating the organic light-emitting material having a specific skeleton of the present invention into the light-emitting layer which emits delayed fluorescence. The element can exhibit excellent performance when being applied to a full-color or multi-color panel. The element may also be utilized in a backlight, lighting, and the like.

The above compounds of formula (I) and the above specific compounds of formula (I') can be used in electrophotographic photoreceptors, photoelectric converters, sensors, dye lasers, solar cell devices and organic light emitting elements. The present invention therefore further relates to the use of the compounds of formula (I) and the specific compounds of formula (I') for electrophotographic photoreceptors, photoelectric converters, sensors, dye lasers, solar cell devices and organic light emitting elements.

The present invention further relates to the use of the compounds of formula (I) and the specific compounds of formula (I') for generating delayed fluorescence emission.

The compounds of formula (I) and the specific compounds of formula (I') of the present invention can be synthesized using copper catalyzed Ullmann conditions or palladium catalyzed Buchwald-Hartwig conditions. Suitable benzobisoxazole, benzobisthiazole and benzobisimidazole base skeletons are either commercially available, or can be obtained by processes known to those skilled in the art. Reference is made to JP10340786, KR20110085784A and KR101160670.

The following examples are included for illustrative purposes only and do not limit the scope of the claims. Unless otherwise stated, all parts and percentages are by weight.

EXAMPLES

Example 1

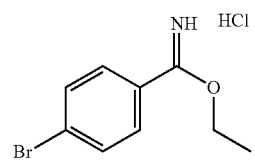

a) 4-Bromobenzonitrile (56 mmol) and Ethanol (35 g) are placed in a 100 ml flask. While stirring, Acetyl chloride (448 mmol) is slowly added. The mixture is stirred at room temperature overnight (15 hours). After the reaction is completed, Ethanol is removed by evaporation, then the residue is washed with Diethyl ether. White solid is obtained by drying in vacuum. (Yield: 84.4%) The product is used for the next reaction without further purification.

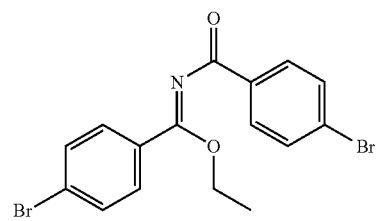 [SMILES: CCO/C(=N\C(=O)c1ccc(Br)cc1)c1ccc(Br)cc1]

b) The product from example 1a (11.3 mmol), Triethylamine (24.9 mmol), 4-Bromobenzoyl chloride (11.3 mmol) and 35 ml of dichloromethane are placed in a 100 ml flask. The mixture is stirred at −15° C. to room temperature overnight (15 hours). After the reaction is completed, dichloromethane is removed by evaporation, then the residue is washed with warm Tetrahydrofuran. White solid is obtained by drying in vacuum. (Crude, Yield: 105%). The product is used for the next reaction without further purification.

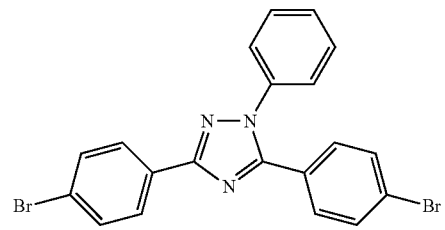 [SMILES: Brc1ccc(-c2nc(-c3ccc(Br)cc3)n(-c3ccccc3)n2)cc1]

c) The product from example 1b (11.3 mmol), phenylhydrazine (12.5 mmol), and 70 ml of tetrachloromethane are placed in a 100 ml flask. The mixture is stirred at room temperature overnight (15 hours). After the reaction is completed, tetrachloromethane is removed by evaporation. The crude product is purified by column chromatography with dichloromethane/hexane=1/30-1/1 as eluent. Beige solid is obtained by drying in vacuum. (yield: 16.5%). $^1$H-NMR (ppm, CDCl$_3$): 8.09 (dd, 2H), 7.59 (dd, 2H), 7.52-7.39 (m, 9H)

(A-1)

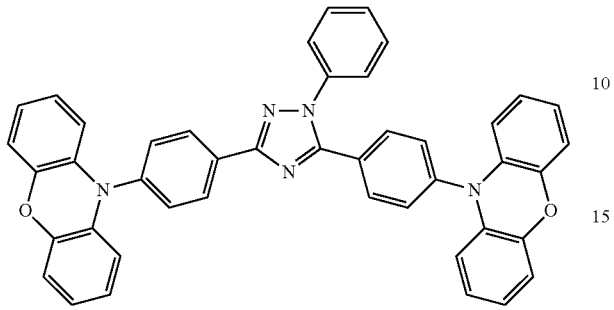

d) The product from example 1c (0.66 mmol), phenoxazine (1.35 mmol), Tris(dibenzylideneacetone) dipalladium (0.013 mmol), tri-tert-butylphosphine (0.026 mmol), sodium t-buthoxide (1.98 mmol) and 7 ml of toluene are placed in a 50 ml flask. The mixture is stirred at 110° C. overnight and cooled. The mixture is filtered and the solid is washed with hexane, subsequently purified by column chromatography with dichloromethane/hexane=1/5 as eluent. Pale yellow solid is obtained by drying in vacuum. (yield: 81.4%). The product is subsequently purified using zone sublimation. $^1$H-NMR (ppm, CDCl$_3$): 8.47 (d, 2H), 7.80 (d, 2H), 7.52 (m, 5H), 7.47 (d, 2H), 7.38 (d, 2H), 6.68 (m, 12H), 6.01 (dd, 2H), 5.94 (dd, 2H)

An organic light-emitting diode prepared comprising a light-emitting layer comprising the compound A-1 emits light with a high external quantum efficiency.

The invention claimed is:

1. A compound of formula

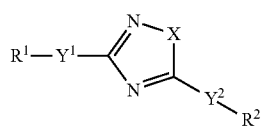

(I)

wherein

X is N—Y$^4$—R$^4$,

Y$^1$ and Y$^2$ and Y$^4$ are independently of each other a direct bond, C$_1$-C$_{25}$-alkylene, or C$_6$-C$_{10}$-arylene, which is unsubstituted or substituted by one or more groups R$^3$;

R$^1$ and R$^2$ are independently of each other deuterium, F, Cl, a C$_1$-C$_{25}$alkyl group, a C$_1$-C$_{25}$alkoxy group, a C$_6$-C$_{14}$aryloxy group, which is unsubstituted or substituted by one or more groups R$^3$, a C$_6$-C$_{14}$aryl group, which is unsubstituted or substituted by one or more groups R$^3$, or a group of formula (Xa) or (Xd);

R$^3$ is deuterium, F, Cl, a C$_1$-C$_{25}$alkyl group, a C$_1$-C$_{25}$alkoxy group, a C$_6$-C$_{14}$aryloxy group, or a C$_6$-C$_{14}$aryl group;

R$^4$ is a C$_1$-C$_{25}$alkyl group, a C$_6$-C$_{10}$aryl group, which is unsubstituted or substituted by one or more groups R$^3$, or a group of formula (Xa) or (Xd);

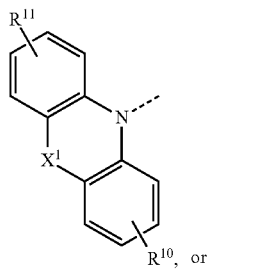

(Xa)

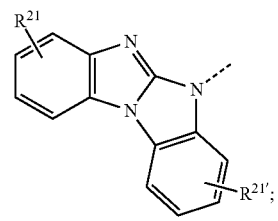

(Xd)

X$^1$ is O, S, N(R$^{15}$), C(=O),—C(R$^{16}$)(R$^{17}$), B(R$^{18}$), or Si(R$^{19}$)(R$^{20}$);

R$^{10}$R$^{11}$R$^{21}$ and R$^{21'}$ are independently of each other hydrogen, deuterium, F, Cl, a C$_1$-C$_{25}$alkyl group, a C$_1$-C$_{25}$alkoxy group, a C$_6$-C$_{14}$aryloxy group, which is unsubstituted or substituted by one or more groups R$^3$, or a C$_6$-C$_{14}$aryl group, which is unsubstituted or substituted by one or more groups R$^3$;

R$^{15}$, R$^{16}$, R$^{17}$, R$^{18}$, R$^{19}$, and R$^{20}$ are independently of each other a C$_1$-C$_{25}$alkyl group, or a C$_6$-C$_{14}$aryl group, which is unsubstituted or substituted by one or more groups R$^3$;

wherein at least one group of formula (Xa), or (Xd) is present in the compound of formula (I).

2. The compound according to claim 1, wherein Y$^1$ and Y$^2$ and Y$^4$ are independently of each other a direct bond, or a group of formula

3. The compound according to claim 1, wherein

R$^1$ and R$^2$ are independently of each other a C$_1$-C$_{25}$alkyl group, a C$_1$-C$_{25}$alkoxy group, a C$_6$-C$_{10}$aryl group, which is unsubstituted or substituted by one or more groups R$^3$, or a group of formula (Xa) or (Xd);

R$^3$ is a C$_1$-C$_{25}$alkyl group, a C$_1$-C$_{25}$alkoxy group, a C$_6$-C$_{10}$aryloxy group, or a C$_6$-C$_{14}$aryl group;

R$^4$ is a C$_1$-C$_{25}$alkyl group, a C$_6$-C$_{10}$aryl group, which is unsubstituted or substituted by one or more groups R$^3$, or a group of formula (Xa) or (Xd);

X$^1$ is O, S, C(O), N(R$^{15}$), or C(R$^{16}$)(R$^{17}$); and

R$^{10}$, R$^{11}$, R$^{21}$ and R$^{21'}$ are independently of each other hydrogen, or a C-C$_{25}$alkyl group;

$R^{15}$ is a group of formula

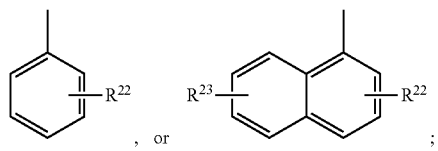, or 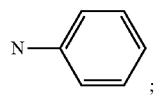;

$R^{16}$ and $R^{17}$ are independently of each other hydrogen, or a $C_1$-$C_{25}$alkyl group;

$R^{22}$ and $R^{23}$ are independently of each other hydrogen, a $C_1$-$C_{25}$alkyl group, a $C_1$-$C_{25}$alkoxy group, a $C_6$-$C_{10}$aryloxy group, or a $C_6$-$C_{10}$aryl group;

wherein at least one group of formula (Xa), or (Xd) is present in the compound of formula (I).

4. The compound according to claim 1, wherein the group of formula (Xa) or (Xd) is a group of formula (Xa), wherein $X^1$ is O, S, C(CH$_3$)(CH$_3$), C(=O),

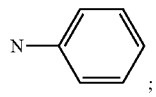;

or a group of formula (Xd), wherein $R^{21}$ and $R^{21'}$ are hydrogen.

5. The compound according to claim 1, wherein the group of formula (Xa) or (Xd) is a group of formula

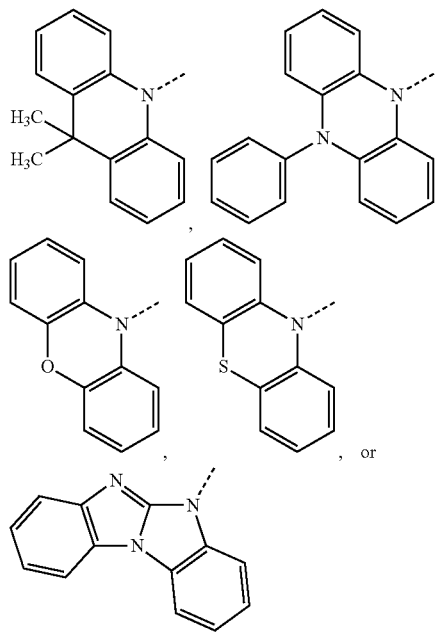

6. The compound according to claim 1, wherein
$R^1$ and $R^2$ are independently of each other a $C_6$-$C_{10}$aryl group, or a group of formula (Xa) or (Xd);
$R^4$ is a $C_1$-$C_{25}$alkyl group, a $C_6$-$C_{10}$aryl group, or a group of formula (Xa) or (Xd);
$X^1$ is O, S, C(CH$_3$)(CH$_3$), C(=O), or

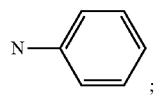;

and
$R^{10}$, $R^{11}$, $R^{21}$ and $R^{21'}$ are independently of each other hydrogen, or a $C_1$-$C_{25}$alkyl group;
wherein at least one group of formula (Xa), or (Xd) is present in the compound of formula (I).

7. A light-emitting layer comprising at least one compound of formula (I) as described in claim 1 as guest and a host material; or comprising at least one compound of formula (I) as described claim 1 as host and a fluorescent guest material.

8. A compound of formula

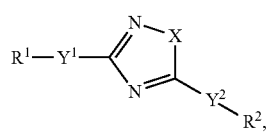

wherein
X is N—Y$^{4'}$—R$^4$ or N—Y$^{4''}$—R$^4$,
Y$^1$ and Y$^2$ are independently of each other a direct bond, $C_1$-$C_{25}$-alkylene, or $C_6$-$C_{10}$-arylene, which is unsubstituted or substituted by one or more groups R$^3$;
Y$^{4'}$ is a direct bond, $C_1$-$C_{25}$-alkylene;
Y$^{4''}$ is $C_6$-$C_{10}$-arylene, which is unsubstituted or substituted by one or more groups R$^3$;
$R^1$ and $R^2$ are independently of each other deuterium, F, Cl, a $C_1$-$C_{25}$alkyl group, a $C_1$-$C_{25}$alkoxy group, a $C_6$-$C_{14}$aryloxy group, which is unsubstituted or substituted by one or more groups R$^3$, a $C_6$-$C_{14}$aryl group, which is unsubstituted or substituted by one or more groups R$^3$, or a group of formula (Xa) or (Xd);

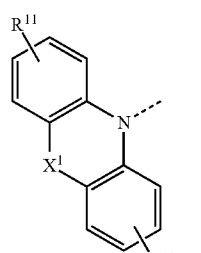

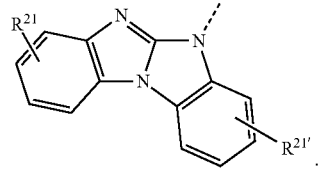

$R^3$ is deuterium, F, Cl, a $C_1$-$C_{25}$alkyl group, a $C_1$-$C_{25}$alkoxy group, a $C_6$-$C_{14}$aryloxy group, or a $C_6$-$C_{14}$aryl group;

R⁴ is a $C_1$-$C_{25}$alkyl group, a $C_6$-$C_{10}$aryl group, which is unsubstituted or substituted by one or more groups R³, or a group of formula (Xa) or (Xd);

X¹ is O, S, N(R¹⁵), C(=O), C(R¹⁶)(R¹⁷), B(R¹⁸), or Si(R¹⁹)(R²⁰), or when X is N—Y⁴''—R⁴,
  X¹ is N(R¹⁵'), C(=O), C(R¹⁶)(R¹⁷), B(R¹⁸), or Si(R¹⁹)(R²⁰), R¹⁰, R¹¹, R²¹ and R²¹' are independently of each other hydrogen, deuterium, F, Cl, a $C_1$-$C_{25}$alkyl group, a $C_1$-$C_{25}$alkoxy group, a $C_6$-$C_{14}$aryloxy group, which is unsubstituted or substituted by one or more groups R³, or a $C_6$-$C_{14}$aryl group, which is unsubstituted or substituted by one or more groups R³;

R¹⁵, R¹⁶, R¹⁷, R¹⁸, R¹⁹, R²⁰ are independently of each other a $C_1$-$C_{25}$alkyl group, or a $C_6$-$C_{14}$aryl group, which is unsubstituted or substituted by one or more groups R³;

R¹⁵' is a $C_6$-$C_{14}$aryl group, which is unsubstituted or substituted by one or more groups R³, wherein at least one group of formula (Xa) or (Xd) is present in the compound of formula (I').

9. The compound according to claim 8, wherein Y¹ and Y² are independently of each other a direct bond, or a group of formula

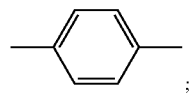
;

and

Y⁴ is selected from a direct bond; and or
Y⁴'' is a group of formula

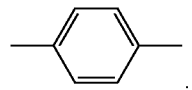
.

10. The compound according to claim 8, wherein

R¹ and R² are independently of each other a $C_1$-$C_{25}$alkyl group, a $C_1C_{25}$alkoxy group, a $C_6$-$C_{10}$aryl group, which is unsubstituted or substituted by one or more groups R³, or a group of formula (Xa) or (Xd);

R³ is a $C_1$-$C_{25}$alkyl group, a $C_1$-$C_{25}$alkoxy group, a $C_6$-$C_{14}$aryloxy group, or a $C_6$-$C_{14}$aryl group;

R⁴ is a $C_1$-$C_{25}$alkyl group, a $C_6$-$C_{10}$aryl group, which is unsubstituted or substituted by one or more groups R³, or a group of formula (Xa) or (Xd);

X¹ is O, S, C(O), N(R¹⁵), or C(R¹⁶)(R¹⁷); or when X is N—Y⁴''—R⁴,
X¹ is N(R¹⁵') or C(R¹⁶)(R¹⁷), and R¹⁰, R¹¹, R²¹ and R²¹' are independently of each other hydrogen, or a $C_1$-$C_{25}$alkyl group;

R¹⁵ and R¹⁵' are independently of each other a group of formula

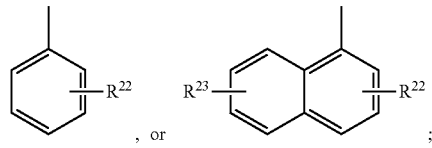
, or ;

R¹⁶ and R¹⁷ are independently of each other hydrogen, or a $C_1$-$C_{25}$alkyl group;

R²² and R²³ are independently of each other hydrogen, a $C_1$-$C_{25}$alkyl group, a $C_1$-$C_{25}$alkoxy group, a $C_6$-$C_{10}$aryloxy group, or a $C_6$-$C_{10}$aryl group;

wherein at least one group of formula (Xa), or (Xd) is present in the compound of formula (I').

11. The compound according to claim 8, wherein the group of formula (Xa) or (Xd) is a group of formula (Xa), wherein X¹ is O, S, C(CH₃)(CH₃), C(=O),

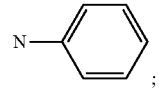
;

or when X is N—Y⁴''—R⁴,
X¹ is C(CH₃)(CH₃), C(=O),

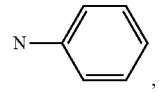
, or a group of formula (Xd), wherein R²¹ and R²¹' are hydrogen.

12. The compound according to claim 8, wherein the group of formula (Xa) or (Xd) is a group of formula

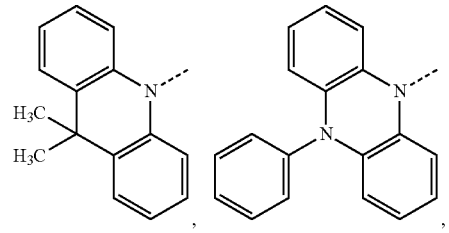
,

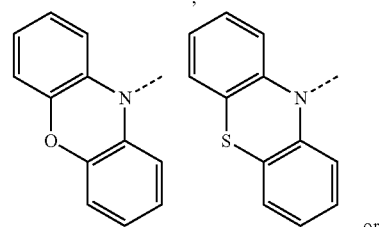
, or

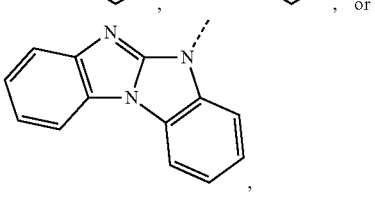

or when X is N—Y⁴'''—R⁴, a group of formula

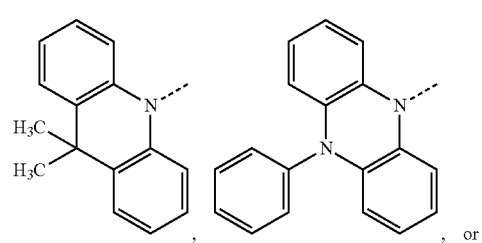
, or

-continued

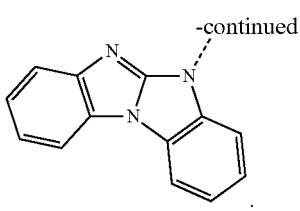

13. The compound according to claim 8, wherein
R$^1$ and R$^2$ are independently of each other a C$_6$-C$_{10}$aryl group, or a group of formula (Xa) or (Xd);
R$^{4'}$ is a C$_1$-C$_{25}$alkyl group, a C$_6$-C$_{10}$aryl group, or a group of formula (Xa) or (Xd);
X$^1$ is O, S, C(CH$_3$)(CH$_3$), C(=O), or

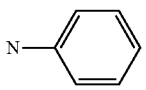

or
when X is N—Y$^{4''}$—R$^4$,
X$^1$ is C(CH$_3$)(CH$_3$), C(=O),

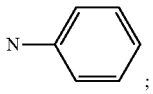

and
R$^{10}$, R$^{11}$, R$^{21}$ and R$^{21'}$ are independently of each other hydrogen, or a C$_1$-C$_{25}$alkyl group;
wherein at least one group of formula (Xa), or (Xd) is present in the compound of formula (I').

14. A light-emitting layer comprising the compound according to claim 8.

15. An organic light emitting element, comprising the compound according to claim 8.

16. The organic light-emitting element according to claim 15, characterized in that it emits light by delayed fluorescence.

17. A device selected from the group consisting of an electrophotographic photoreceptor, a photoelectric converter, a sensor, a dye laser, a solar cell device and an organic light emitting element, wherein the device comprises the organic light-emitting element of claim 15.

18. A compound of formula

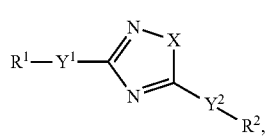

wherein
X is O, S or N—Y$^4$—R$^4$,
Y$^1$ and Y$^2$ and Y$^4$ are independently of each other a direct bond, C$_1$-C$_{25}$-alkylene, or C$_6$-C$_{10}$-arylene, which is unsubstituted or substituted by one or more groups R$^3$;

R$^1$ and R$^2$ are independently of each other deuterium, F, Cl, a C$_1$-C$_{25}$alkyl group, a C$_1$-C$_{25}$alkoxy group, a C$_6$-C$_{14}$aryloxy group, which is unsubstituted or substituted by one or more groups R$^3$, a C$_6$-C$_{14}$aryl group, which is unsubstituted or substituted by one or more groups R$^3$, or a group of formula (Xa) or (Xd);

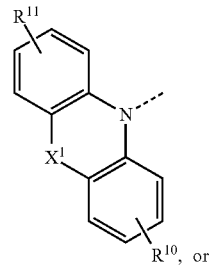

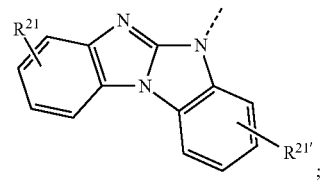

R$^3$ is deuterium, F, Cl, a C$_1$-C$_{25}$alkyl group, a C$_1$-C$_{25}$alkoxy group, a C$_6$-C$_{14}$aryloxy group, or a C$_6$-C$_{14}$aryl group;
R$^4$ is a C$_1$-C$_{25}$alkyl group, a C$_6$-C$_{10}$aryl group, which is unsubstituted or substituted by one or more groups R$^3$, or a group of formula (Xa) or (Xd);
X$^1$ is O, S, N(R$^{15}$), C(=O), C(R$^{16}$)(R$^{17}$), B(R$^{18}$), or Si(R$^{19}$)(R$^{20}$);
R$^{10}$, R$^{11}$, R$^{21}$ and R$^{21'}$ are independently of each other hydrogen, deuterium, F, Cl, a C$_1$-C$_{25}$alkyl group, a C$_1$-C$_{25}$alkoxy group, a C$_6$-C$_{14}$aryloxy group, which is unsubstituted or substituted by one or more groups R$^3$, or a C$_6$-C$_{14}$aryl group, which is unsubstituted or substituted by one or more groups R$^3$;
R$^{15}$, R$^{16}$, R$^{17}$, R$^{18}$, R$^{19}$ and R$^{20}$ are independently of each other a C$_1$-C$_{25}$alkyl group, or a C$_6$-C$_{14}$aryl group, which is unsubstituted or substituted by one or more groups R$^3$;
wherein at least one group of formula (Xd) is present in the compound of formula (I).

19. A light-emitting layer comprising the compound according to claim 18.

20. An organic light emitting element, comprising the compound according to claim 18.

21. The organic light-emitting element according to claim 20, characterized in that it emits light by delayed fluorescence.

22. A device selected from the group consisting of an electrophotographic photoreceptor, a photoelectric converter, a sensor, a dye laser, a solar cell device and an organic light emitting element, wherein the device comprises the organic light-emitting element of claim 20.

23. A device selected from the group consisting of an electrophotographic photoreceptor, a photoelectric converter, a sensor, a dye laser, a solar cell device and an organic light emitting element, wherein the device comprises the organic light-emitting element of claim 7.

* * * * *